(12) United States Patent
Kumar et al.

(10) Patent No.: US 9,981,973 B2
(45) Date of Patent: *May 29, 2018

(54) TRICYCLIC COMPOUNDS AS INHIBITORS OF IMMUNOSUPPRESSION MEDIATED BY TRYPTOPHAN METABOLIZATION

(71) Applicant: NewLink Genetics Corporation, Ames, IA (US)

(72) Inventors: Sanjeev Kumar, Ames, IA (US); Jesse Waldo, Huxley, IA (US); Firoz Jaipuri, Ames, IA (US); Mario Mautino, Ankeny, IA (US)

(73) Assignee: NEWLINK GENETICS CORPORATION, Ames, IA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/434,414

(22) Filed: Feb. 16, 2017

(65) Prior Publication Data

US 2017/0260188 A1    Sep. 14, 2017

Related U.S. Application Data

(63) Continuation of application No. 14/774,450, filed as application No. PCT/US2014/022680 on Mar. 10, 2014, now Pat. No. 9,617,272.

(60) Provisional application No. 61/784,089, filed on Mar. 14, 2013.

(51) Int. Cl.
*C07D 235/02* (2006.01)
*C07D 487/04* (2006.01)

(52) U.S. Cl.
CPC ......... *C07D 487/04* (2013.01); *C07D 235/02* (2013.01)

(58) Field of Classification Search
None
See application file for complete search history.

(56) References Cited

U.S. PATENT DOCUMENTS

2007/0142305 A1    6/2007    Ho et al.

FOREIGN PATENT DOCUMENTS

WO    WO 2012/142237    10/2012

OTHER PUBLICATIONS

Lemke et al., "Heterocyclic Tricycles as Potential CNS Agents I: 4-Aminoalkylindeno[1,2-c]pyrazoles," Journal of Pharmaceutical Sciences, vol. 67, No. 10, Oct. 1, 1978, pp. 1377-1381.
Meininger et al., "Purification and kinetic characterisation of human indoleamine 2,3-dioxygenases 1 and 2 (IDO1 and IDO2) and discovery of selective IDO1 inhibitors," Biochimica et Biophysica Acta, vol. 23, No. 7, Jul. 1, 2011, pp. 1947-1954.

*Primary Examiner* — Alicia L Otton
(74) *Attorney, Agent, or Firm* — McDonnell Boehnen Hulbert & Berghoff LLP

(57) ABSTRACT

Presently provided are inhibitors of IDO and TDO and pharmaceutical compositions thereof, useful for modulating an activity of indoleamine 2,3-dioxygenase and tryptophan 2,3 dioxygenase; treating immunosuppression; treating a medical conditions that benefit from the inhibition of tryptophan degradation; enhancing the effectiveness of an anti-cancer treatment comprising administering an anti-cancer agent; treating tumor-specific immunosuppression associated with cancer; and treating immunosuppression associated with an infectious disease.

38 Claims, 4 Drawing Sheets

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
ggagcatgct aatggcacac gctatggaaa ac                           32

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
gagagatcta ccttccttca aaagggattt c                            31

TRICYCLIC COMPOUNDS AS INHIBITORS OF IMMUNOSUPPRESSION MEDIATED BY TRYPTOPHAN METABOLIZATION

CROSS-REFERENCE TO RELATED APPLICATIONS

This application is a continuation of U.S. application Ser. No. 14/774,450 filed Sep. 10, 2015, which claims priority to International Patent Application No. PCT/US2014/022680 filed on 10 Mar. 2014, which claims the benefit of the filing date of U.S. Provisional Application Ser. No. 61/784,089 filed 14 Mar. 2013, the entirety of each of the foregoing applications is hereby incorporated by reference into the present specification.

BACKGROUND OF THE INVENTION

Field of the Invention

The present disclosure relates to compounds and methods for inhibition of indoleamine 2,3-dioxygenase (IDO) and tryptophan 2,3-dioxygenase (TDO); further the disclosure relates to method of treatment of diseases and disorders mediated by tryptophan deficiency.

Summary of the Related Art

Tryptophan (Trp) is an essential amino acid required for the biosynthesis of proteins, niacin and the neurotransmitter 5-hydroxytryptamine (serotonin). The enzymes indoleamine 2,3-dioxygenase 1 (also known as INDO1 or IDO1), indoleamine-2,3-dioxygenase 2 (INDOL1 or IDO2) and tryptophan-2,3-dioxygenase (TDO) catalyze the first and rate limiting step in the degradation of L-tryptophan to N-formyl-kynurenine. Although these enzymes catalyze the same reaction, compartmentalization of IDO and TDO is thought to mediate their different biological roles. IDO1 is normally expressed in cells of the gastrointestinal and pulmonary epithelia, epididymus, placenta, pDCs in draining lymph nodes and tumor cells. IDO2 is expressed mainly in brain and placenta, but certain splice variants are also detected in liver, small intestine, spleen, placenta, thymus lung, brain, kidney and colon. TDO is expressed mainly in liver, and controls the flux of dietary Trp to the serotonin and kynurenine pathways.

Alignment between IDO1 and IDO2 amino acid sequences reveal highly conserved features that mediate heme and substrate binding. Even though the amino acid sequence identity between IDO1 and IDO2 or IDO1 and TDO are not particularly high, significant residues determined to be important for catalytic activity by IDO and TDO mutagenesis and by crystallographic analysis are highly conserved between IDO1, IDO2 and TDO, suggesting a structural and functional analogy in the mechanism of tryoghan dioxygenation. Despite these structural similarities at the active site, IDO1 and TDO have different substrate specificity with TDO being almost exclusively specific for L-Trp and L-Trp derivatives substituted inte 5- and 6-positions of the indole group, while IDO1 can accept and oxygenate a wider variety of substrates such as D-Trp, tryptamine, serotonin and 1-methyl-L-Trp.

In human cells, IFN-γ stimulation induces activation of IDO1, which leads to a depletion of Trp, thereby arresting the growth of Trp-dependent intracellular pathogens such as *Toxoplasma gondii* and *Chlamydia trachomatis*. IDO1 activity also has an antiproliferative effect on many tumor cells, and IDO1 induction has been observed in vivo during rejection of allogeneic tumors, indicating a possible role for this enzyme in the tumor rejection process.

It has been observed that HeLa cells co-cultured with peripheral blood lymphocytes (PBLs) acquire an immunoinhibitory phenotype through up-regulation of the IDO pathway. A reduction in PBL proliferation upon treatment with interleukin-2 (IL-2) was believed to result from IDO released by the tumor cells in response to IFN-γ secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO inhibition can enhance the levels of virus-specific T cells and, concomitantly, reduce the number of virally infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, Nature Med., 11:312-9).

A similar situation has been observed with TDO. It has been shown that a significant proportion of primary human tumors express elevated levels of TDO or TDO plus IDO (Pilotte et al. 2012, P.N.A.S). Moreover, pharmacological inhibition of TDO activity with TDO inhibitors, leads to immune-mediated rejection of tumors overexpressing TDO, which means that TDO, just as seen in IDO1, can mediate tumor-promoting immunosuppressive effects.

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, Science 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest., 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8).

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; WO 2009/073620; WO 2009/132238; WO 2011/056652 and WO 2012/142237. In particular, the compounds of WO 202/142237 encompass a series of trycyclic imidazoisoindoles with potent IDO inhibitory activity.

SUMMARY OF THE INVENTION

In light of the experimental data indicating a role for IDO and/or TDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO1, IDO2 and/or TDO activity are desirable. Specific or dual inhibitors of IDO1, IDO2 and TDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO1, IDO2 and TDO modulators.

In this invention, we describe novel structures related to imidazoisoindoles, with different electronic and heme binding properties, that can specifically inhibit IDO1, IDO2 or TDO, or that can exert combined inhibition of tryptophan degradation mediated by any of these enzymes.

In one aspect, the invention comprises compounds according to the formula (I) and its tautomers,

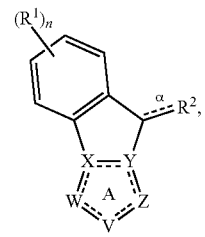

wherein
$R^1$, $R^2$, and n are each defined herein;
bond α is a simple or double bond
ring A is an aromatic ring wherein
i) V and X are N, W and Z are CH and Y is C; or
ii) V, Y and Z are N, W is CH and X is C; or
iii) V, W and Y are N, X is C and Z is CH; or
iv) V and W are N or NH, X and Y are C and Z is CH;

In a most preferred embodiment, the invention comprises compounds of Formula (I) where V and X are nitrogen (N), W and Z are CH and Y is carbon (C), to yield compounds of Formula (II),

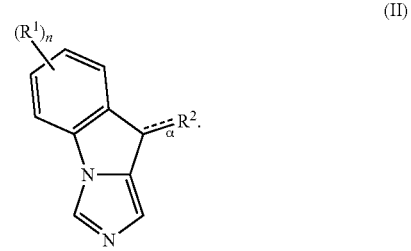

In another preferred embodiment, the invention comprises compounds of Formula (I) where V, Y and Z nitrogen (N), W is CH and X is carbon (C), to yield compounds of Formula (III),

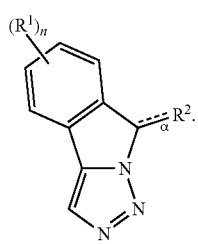

(III)

In another embodiment, the invention comprises compounds of Formula (I) where V, W and Y are nitrogen (N), X is carbon (C) and Z is CH, to yield compounds of Formula (IV),

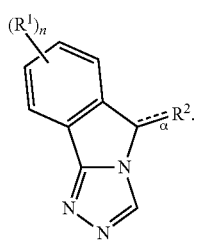

(IV)

In another embodiment, the invention comprises compounds of Formula (I) where V and W are nitrogen (N) or NH, respectively or reciprocally, X and Y are carbon (C), and Z is CH, to yield tautomeric compounds of Formula (V),

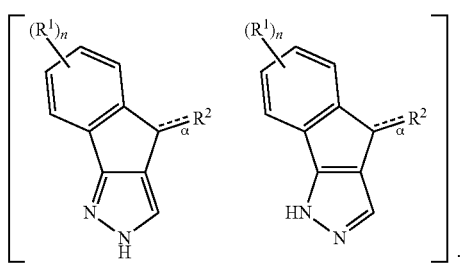

(V)

In another preferred embodiment, the invention comprises compounds of formulas II, III, IV and V where bond alpha (α) is a single bond.

In another preferred embodiment, the invention comprises compounds of formulas II, III, IV and V where bond alpha (α) is a double bond.

In another aspect pharmaceutical compositions are provided comprising a pharmaceutically acceptable excipient, diluent, or carrier, and a compound according to formula (I), (II), (III), (IV) or (V).

In another aspect methods are provided for (a) modulating an activity of IDO1, IDO2 or TDO comprising contacting an IDO1, IDO2 or TDO with a modulation effective amount of a compound according to formula (I), or a pharmaceutical composition comprising a compound according to formula (I); (b) treating IDO1, IDO2 or TDO mediated immunosuppression in a subject in need thereof, comprising administering an effective inhibiting amount of a compound according to formula (I), or a pharmaceutical composition comprising a compound according to formula (I); (c) treating a medical condition that benefits from the inhibition of tryptophan degradation mediated by IDO1, IDO2 or comprising administering an effective amount of a compound of formula (I), or a pharmaceutical composition comprising a compound according to formula (I); (d) enhancing the effectiveness of an anti-cancer treatment comprising administering an anti-cancer agent and a compound according to formula (I), or a pharmaceutical composition comprising a compound according to formula (I); (e) treating tumor-specific immunosuppression associated with cancer comprising administering an effective amount of a compound according to formula (I), or a pharmaceutical composition comprising a compound according to formula (I); and (f) treating immunosuppression associated with an infectious disease, e.g., HIV-1 infection, comprising administering an effective amount of a compound according to formula (I), or a pharmaceutical composition comprising a compound according to formula (I).

DETAILED DESCRIPTION OF THE INVENTION

Figure 1:
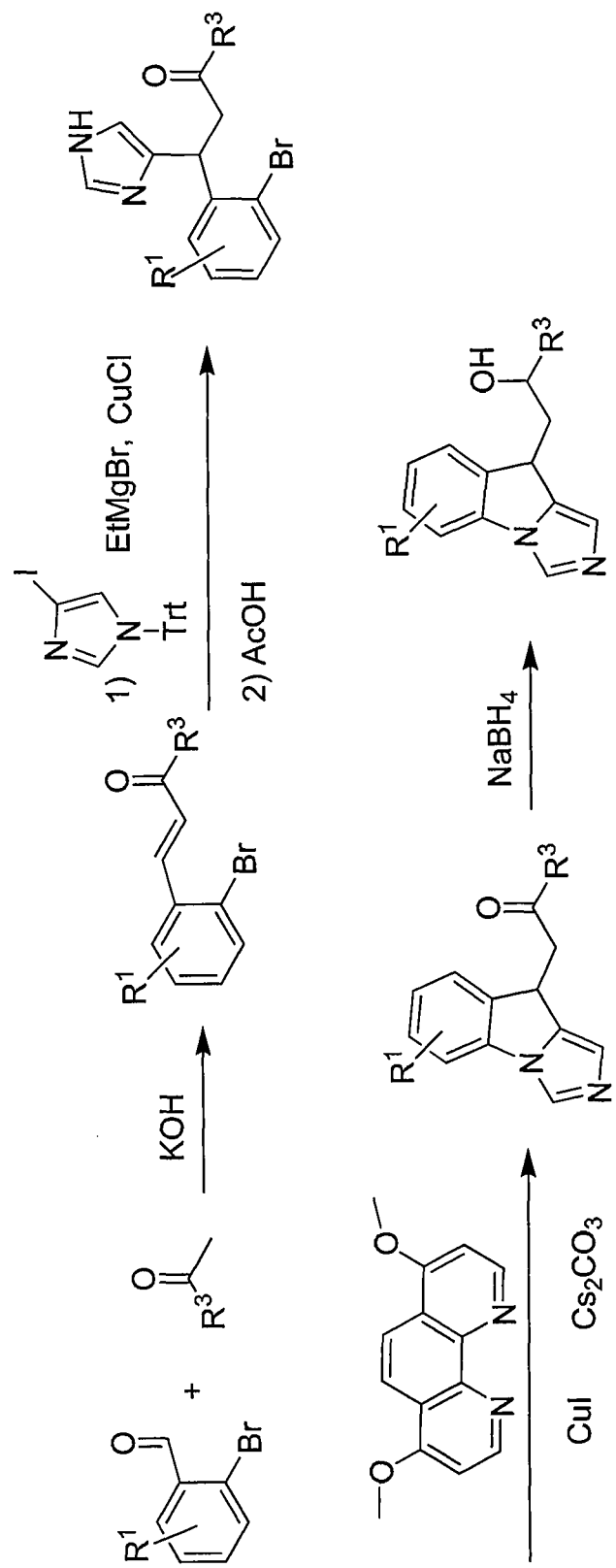
FIG. 1 describes the general scheme of synthesis of compounds of Formula I, when V and X are N, W and Z are CH and Y is C, and bond α is a single bond.
Figure 2:
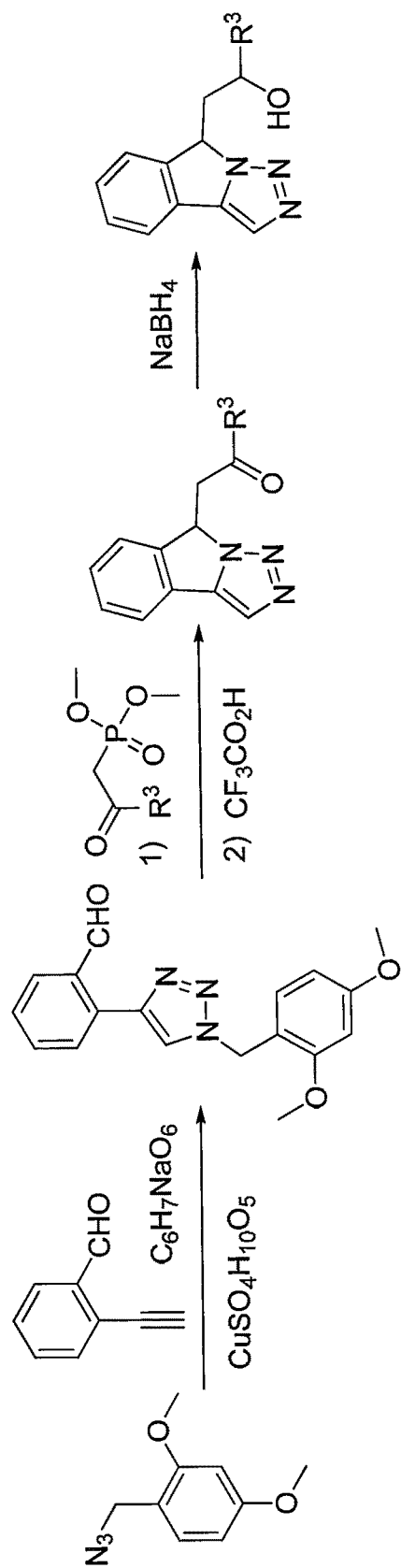
FIG. 2 describes the general scheme of synthesis of compounds of Formula I, when V, Y and Z are N, X is C, W is CH and bond α is a single bond.
Figure 3:
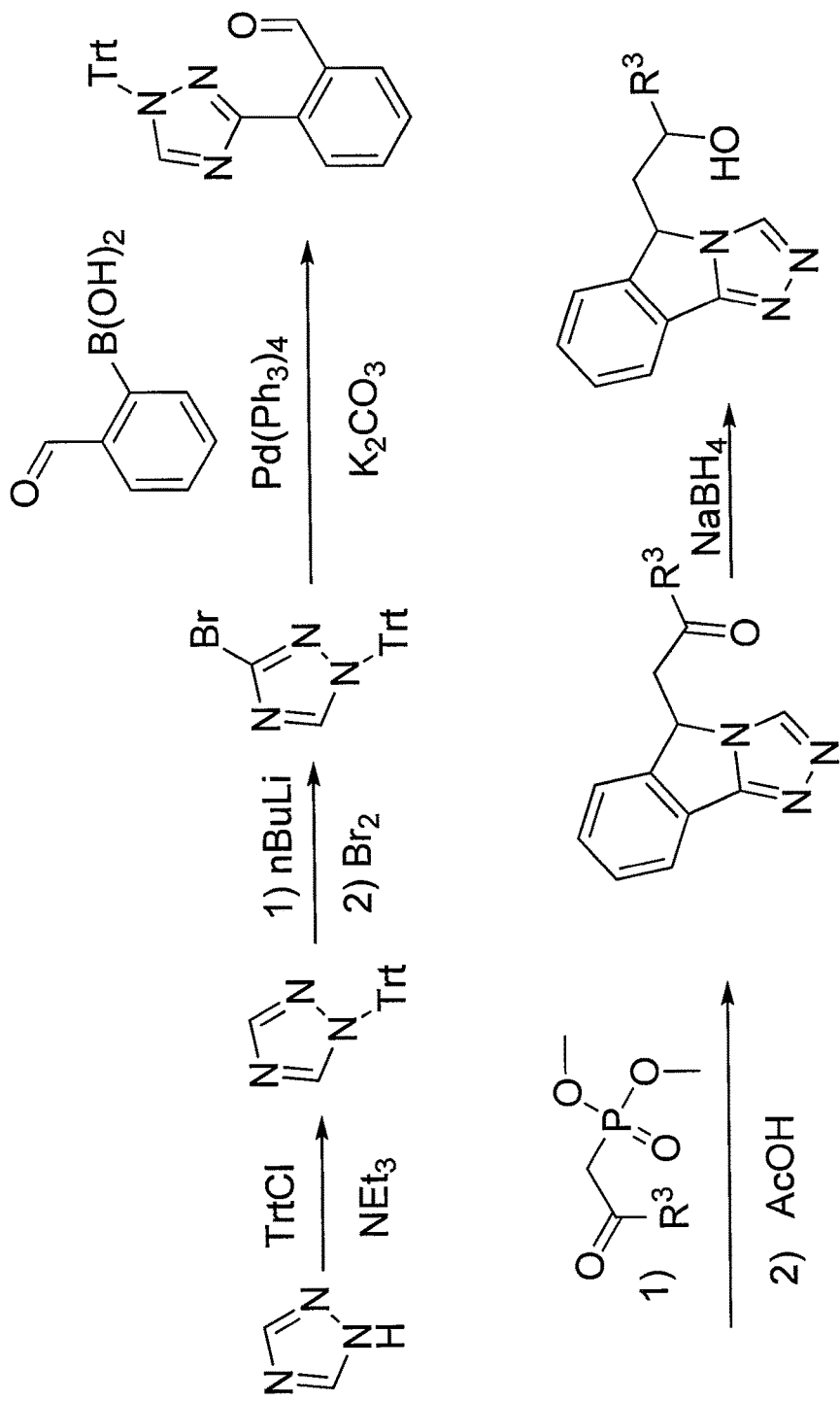
FIG. 3 describes the general scheme of synthesis of compounds of Formula I when V, W and Y are nitrogen (N), X is carbon (C), Z is CH and bond α is a single bond.
Figure 4:
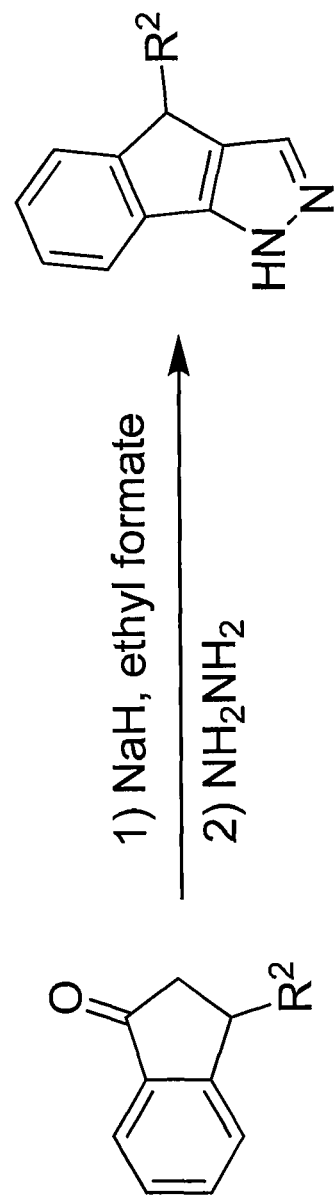
FIG. 4 describes the general scheme of synthesis of compounds of Formula I when V and W are N or NH, X and Y is C, Z is CH and bond α is a single bond.

In one aspect, the invention provides compounds of formula (I),

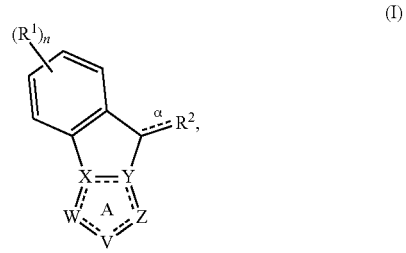

(I)

its tautomers or a pharmaceutically acceptable salt thereof, wherein
n is 0, 1, 2, 3, or 4;
bond α is a simple or double bond
ring A is an aromatic ring wherein
i) V and X are N, W and Z are CH and Y is C; or
ii) V, Y and Z are N, W is CH and X is C; or
iii) V, W and Y are N, X is C and Z is CH; or
iv) V and W are N or NH, X and Y are C and Z is CH;
each $R^1$ is independently halogen, cyano, nitro, $C_{1-4}$alkyl, $C_{1-4}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

R² is —C₁₋₄alkyl-Rᴬ or —C₂₋₄alkenyl-R³ when bond α is a single bond; and

R² is =C(H)Rᴬ when bond α is a double bond;

wherein

Rᴬ is —CN, —C(O)R³, —C(O)OR³, —C(O)N(R³)(Rᶜ), —C(ORᴮ)(R³)(Rᶜ), —C(NHRᴮ)(R³)(Rᶜ), or —C(=N—ORᶜ)R³, wherein Rᴮ is hydrogen, C₁₋₆alkyl, C₁₋₆haloalkyl, —C₁₋₆alkyl-Rᴮ¹, —C(O)R³, or —S(O)₂R³, —C(O)(CH₂)₁₋₄COOR, —C(O)CH(NH₂)(Rᴰ), —S(O)₂OR³, —S(O)₂N(R³)₂, —CH₂—OP(O)₂(OR)₂, or —P(O)(OR³)₂, wherein Rᴮ¹ is cyano, nitro, C₁₋₆alkyl, C₁₋₆haloalkyl, —OR, —N(R)₂, —SR, —C(O)OR, —C(O)N(R)₂, —C(O)R, —S(O)R, —S(O)OR, —S(O)N(R)₂, —S(O)₂R, —S(O)₂OR, —S(O)₂N(R)₂, —OC(O)R, —OC(O)OR, —OC(O)N(R)₂, —N(R)C(O)R, —N(R)C(O)OR, or —N(R)C(O)N(R)₂;

Rᴰ is hydrogen, methyl, —CH(CH₃)₂, —CH₂CH(CH₃)₂, —CH(CH₃)(CH₂CH₃), benzyl, 4-hydroxybenzyl, —CH₂(3-indolyl), —CH₂SH, —CH₂CH₂SCH₃, —CH₂OH, —CH(CH₃)OH, —(CH₂)₄—NH₂, —(CH₂)₃—N(H)C(=NH)NH₂, —CH₂(4-imidazolyl), —CH₂COOH, —CH₂CH₂COOH, —CH₂CONH₂, —CH₂CH₂CONH₂;

each R³ is independently hydrogen, C₁₋₆alkyl, C₁₋₆haloalkyl, aryl, heteroaryl, C₃₋₈cycloalkyl, C₃₋₈cycloalkenyl, 3-10 membered heterocyclyl, arylC₁₋₆alkyl-, heteroarylC₁₋₆ alkyl-, C₃₋₈cycloalkylC₁₋₆alkyl-, C₃₋₈cycloalkenylC₁₋₆alkyl-, or (3-10 membered heterocyclyl)C₁₋₆alkyl-, wherein the alkyl, C₃₋₈cycloalkyl, C₃₋₈cycloalkenyl, 3-10 membered heterocyclyl, C₃₋₈cycloalkylC₁₋₆alkyl-, C₃₋₈cycloalkenylC₁₋₆alkyl-, and (3-10 membered heterocyclyl)C₁₋₆alkyl- are each optionally and independently substituted by one =R³² group and each optionally substituted and independently by one, two, three, or four R³¹ groups;

the aryl, heteroaryl, arylC₁₋₆alkyl-, and heteroaryl C₁₋₆alkyl- groups, are each optionally substituted by one, two, three, or four R³¹ groups;

wherein each R³¹ is independently halogen, cyano, nitro, C₁₋₆alkyl, —C₁₋₆alkyl-R³³, C₁₋₆haloalkyl, —OR, —N(R)₂, —SR, —C(O)OR, —C(O)N(R)₂, —C(O)R, —S(O)R, —S(O)OR, —S(O)N(R)₂, —S(O)₂R, —S(O)₂OR, —S(O)₂N(R)₂, —OC(O)R, —OC(O)OR, —OC(O)N(R)₂, —N(R)C(O)R, —N(R)C(O)OR, —N(R)C(O)N(R)₂, wherein R³³ is cyano, —OR, —N(R)₂, —SR, —C(O)OR, —C(O)N(R)₂, —C(O)R, —S(O)R, —S(O)OR, —S(O)N(R)₂, —S(O)₂R, —S(O)₂OR, —S(O)₂N(R)₂, —OC(O)R, —OC(O)OR, —OC(O)N(R)₂, —N(R)C(O)R, —N(R)C(O)OR, or —N(R)C(O)N(R)₂;

R³² is =O, =S, =N(R), =N(OR), =C(R³⁴)₂, =(spiro-C₃₋₈cycloalkyl), or =(spiro-(3-10 membered heterocyclyl)), wherein each R³⁴ is independently hydrogen, halogen, C₁₋₆alkyl, C₁₋₆haloalkyl, C₃₋₈cycloalkyl, or 3-10 membered heterocyclyl;

or both R³⁴ taken together with the atom to which they are both attached form a monocyclic C₃₋₈cycloalkyl or monocyclic 3-8 membered heterocyclyl;

Rᶜ is hydrogen or C₁₋₆alkyl;

and each R is independently hydrogen or R¹⁰, wherein

R¹⁰ is C₁₋₆alkyl, C₁₋₆haloalkyl, aryl, heteroaryl, C₃₋₈cycloalkyl, C₃₋₈cycloalkenyl, 3-10 membered heterocyclyl, arylC₁₋₆alkyl, heteroarylC₁₋₆alkyl-, C₃₋₈cycloalkylC₁₋₆alkyl-, C₃₋₈cycloalkenylC₁₋₆alkyl-, or (3-10 membered heterocyclyl)C₁₋₆alkyl-, each R¹⁰ optionally substituted by one, two, three, or four groups that are each independently halogen, cyano, nitro, C₁₋₆alkyl, C₁₋₆haloalkyl, —OR¹¹, —N(R¹¹)₂, —SR¹¹, —C(O)OR¹¹, —C(O)N(R¹)₂, —C(O)R¹¹, —S(O)R¹¹, —S(O)OR¹¹, —S(O)N(R¹¹)₂, —S(O)₂R¹¹, —S(O)₂OR¹¹, —S(O)₂N(R¹¹)₂, —OC(O)R¹¹, —OC(O)OR¹¹, —OC(O)N(R¹¹)₂, —N(R¹¹)C(O)R¹¹, —N(R¹¹)C(O)OR¹¹, —N(R¹¹)C(O)N(R¹¹)₂, wherein each R¹¹ is independently hydrogen or C₁₋₆alkyl.

The invention further comprises subgenera of formula (I) in which the substituents are selected as any and all combinations of one or more of structural formula (I), n, R¹, R², R³, Rᴬ, Rᴮ, and Rᶜ, as defined herein, including without limitation, the following:

Structural Formula I is One of Formulae (IIa)-(Vc):

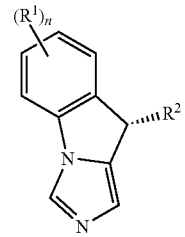

(IIa)

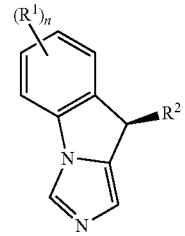

(IIb)

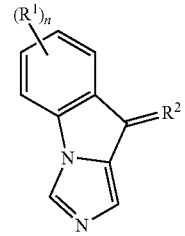

(IIv)

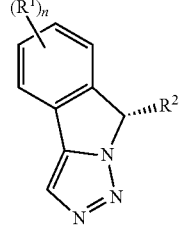

(IIIa)

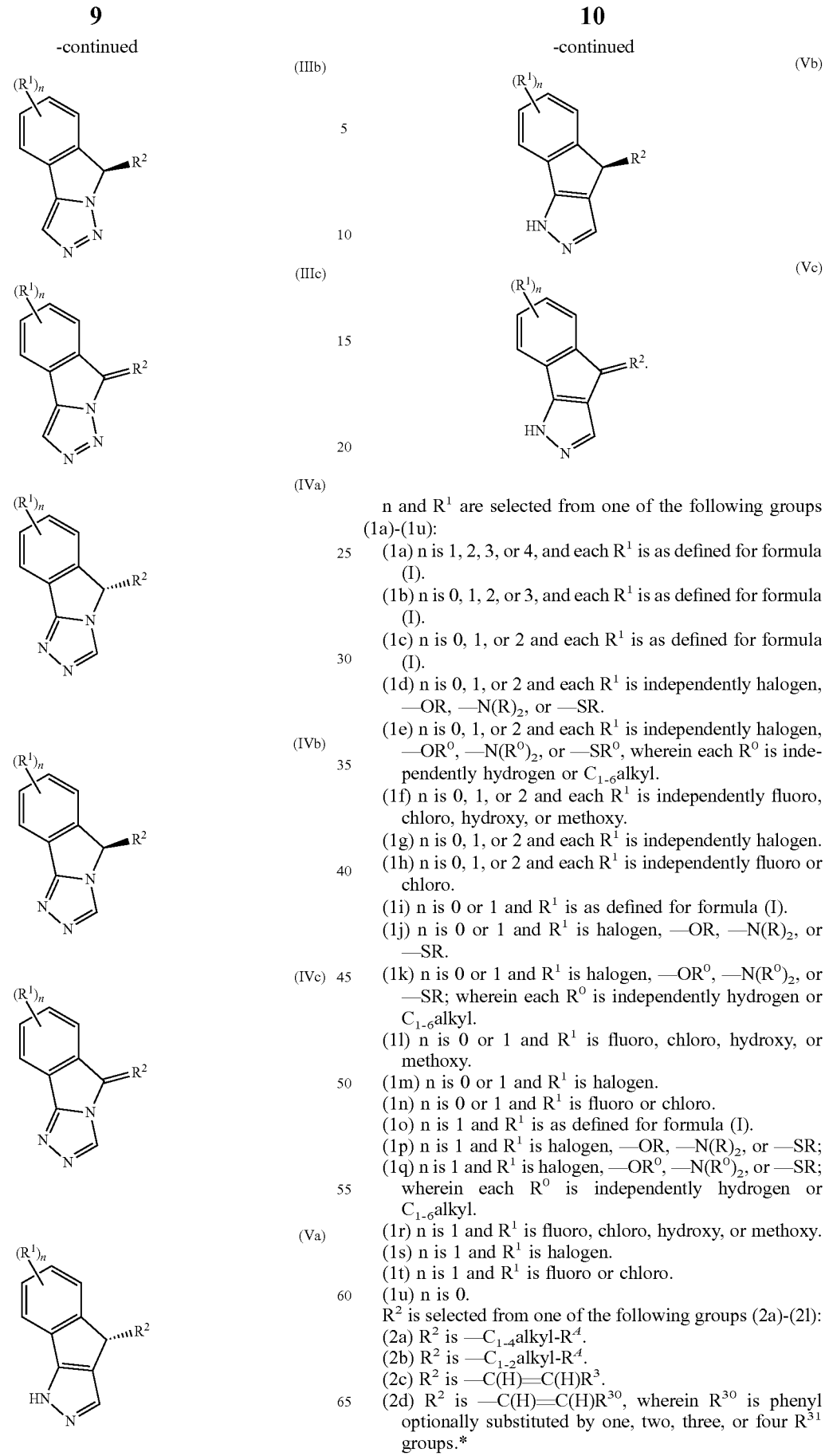

n and R¹ are selected from one of the following groups (1a)-(1u):
(1a) n is 1, 2, 3, or 4, and each R¹ is as defined for formula (I).
(1b) n is 0, 1, 2, or 3, and each R¹ is as defined for formula (I).
(1c) n is 0, 1, or 2 and each R¹ is as defined for formula (I).
(1d) n is 0, 1, or 2 and each R¹ is independently halogen, —OR, —N(R)$_2$, or —SR.
(1e) n is 0, 1, or 2 and each R¹ is independently halogen, —OR⁰, —N(R⁰)$_2$, or —SR⁰, wherein each R⁰ is independently hydrogen or C$_{1-6}$alkyl.
(1f) n is 0, 1, or 2 and each R¹ is independently fluoro, chloro, hydroxy, or methoxy.
(1g) n is 0, 1, or 2 and each R¹ is independently halogen.
(1h) n is 0, 1, or 2 and each R¹ is independently fluoro or chloro.
(1i) n is 0 or 1 and R¹ is as defined for formula (I).
(1j) n is 0 or 1 and R¹ is halogen, —OR, —N(R)$_2$, or —SR.
(1k) n is 0 or 1 and R¹ is halogen, —OR⁰, —N(R⁰)$_2$, or —SR; wherein each R⁰ is independently hydrogen or C$_{1-6}$alkyl.
(1l) n is 0 or 1 and R¹ is fluoro, chloro, hydroxy, or methoxy.
(1m) n is 0 or 1 and R¹ is halogen.
(1n) n is 0 or 1 and R¹ is fluoro or chloro.
(1o) n is 1 and R¹ is as defined for formula (I).
(1p) n is 1 and R¹ is halogen, —OR, —N(R)$_2$, or —SR;
(1q) n is 1 and R¹ is halogen, —OR⁰, —N(R⁰)$_2$, or —SR; wherein each R⁰ is independently hydrogen or C$_{1-6}$alkyl.
(1r) n is 1 and R¹ is fluoro, chloro, hydroxy, or methoxy.
(1s) n is 1 and R¹ is halogen.
(1t) n is 1 and R¹ is fluoro or chloro.
(1u) n is 0.

R² is selected from one of the following groups (2a)-(2l):
(2a) R² is —C$_{1-4}$alkyl-R$^A$.
(2b) R² is —C$_{1-2}$alkyl-R$^A$.
(2c) R² is —C(H)=C(H)R³.
(2d) R² is —C(H)=C(H)R³⁰, wherein R³⁰ is phenyl optionally substituted by one, two, three, or four R³¹ groups.*

(2e) $R^2$ is —C(H)=C(H)$R^{30}$, wherein $R^{30}$ is phenyl optionally substituted by one or two $R^{31}$ groups.
(2f) $R^2$ is —CH$_2$—$R^4$, —CH$_2$CH$_2$—$R^4$, —C(H)(CH$_3$)CH$_2$—$R^4$, or —C(H)=C(H)$R^3$.
(2g) $R^2$ is —CH$_2$—$R^4$, —CH$_2$CH$_2$—$R^4$, or —C(H)(CH$_3$)CH$_2$—$R^4$.
(2h) $R^2$ is —CH$_2$—$R^4$, —CH$_2$CH$_2$—$R^4$, or —C(H)=C(H)$R^3$.
(2i) $R^2$ is —CH$_2$—$R^4$.
(2j) $R^2$ is —CH$_2$CH$_2$—$R^4$.
(2k) $R^2$ is —C(H)(CH$_3$)CH$_2$—$R^4$.
(2l) $R^2$ is —CH$_2$—$R^4$, —CH$_2$CH$_2$—$R^4$, or —C(H)=C(H)$R^3$.
(2m) $R^2$ is =CH—$R^4$, =CHCH$_2$—$R^4$, or =C(H)C(H)$R^3$.

$R^4$ is selected from one of the following groups (3a)-(3n):
(3a) $R^4$ is —CN, —C(O)O$R^3$, or —C(O)N($R^3$)($R^C$).
(3b) $R^4$ is —C(O)$R^3$ or —C(O$R^B$)($R^3$)($R^C$).
(3c) $R^4$ is —C(NH$R^B$)($R^3$)($R^C$), or —C(=N—O$R^C$)$R^3$.
(3d) $R^4$ is —C(NH$R^B$)($R^3$)($R^C$), wherein $R^B$ is hydrogen, $C_{1-6}$alkyl, or —C(O)$C_{1-6}$alkyl.
(3e) $R^4$ is —C(NH$_2$)($R^3$)($R^C$).
(3f) $R^4$ is —C(O)O$R^3$.
(3g) $R^4$ is —C(O)N($R^3$)($R^C$).
(3h) $R^4$ is —C(O)$R^3$.
(3i) $R^4$ is —C(O$R^B$)($R^3$)($R^C$).
(3j) $R^4$ is —C(OH)($R^3$)($R^C$).
(3k) $R^4$ is —CH(OH)($R^3$).
(3l) $R^4$ is —CN, —C(O)$R^3$, —C(O)O$R^3$, —C(O)N($R^3$)($R^C$), —C(O$R^B$)($R^3$)($R^C$), —C(NH$R^B$)($R^3$)($R^C$), or —C(=N—O$R^C$)$R^3$.
(3m) $R^4$ is —C(O)$R^3$ or —C(O$R^B$)($R^3$)($R^C$), wherein $R^B$ is hydrogen and $R^C$ is hydrogen or $C_{1-6}$alkyl.
(3n) $R^4$ is —C(O$R^B$)($R^3$)($R^C$), wherein $R^B$ is hydrogen and $R^C$ is hydrogen or $C_{1-6}$alkyl.

$R^B$ is selected from one of the following groups (4a)-(4k):
(4a) $R^B$ is hydrogen, $C_{1-4}$alkyl, $C_{1-4}$haloalkyl, —$C_{1-4}$alkyl-$R^{B1}$, —C(O)(CH$_2$)$_{1-4}$COO$R^{B2}$, —C(O)C(NH$_2$)$R^D$, —P(O$_3$)($R^{B2}$)$_2$, —CH$_2$—OP(O)$_2$(OR)$_2$, wherein $R^D$ is the side chain of natural alpha amino acids, —C(O)$R^3$, or —S(O)$_2$$R^3$, wherein $R^{B1}$ is cyano, nitro, $C_{1-6}$alkyl, $C_{1-6}$haloalkyl, —O$R^{B2}$, —N($R^{B2}$)$_2$, —S$R^{B2}$, —C(O)O$R^{B2}$, —C(O)N($R^{B2}$)$_2$, —C(O)$R^{B2}$, —S(O)$R^{B2}$, —S(O)O$R^{B2}$, —S(O)N($R^{B2}$)$_2$, —S(O)$_2$$R^{B2}$, —S(O)$_2$O$R^{B2}$, —S(O)$_2$N($R^B$)$_2$, —OC(O)$R^{B2}$, —OC(O)O$R^{B2}$, —OC(O)N($R^{B2}$)$_2$, N($R^{B2}$)C(O)$R^{B2}$, —N($R^{B2}$)C(O)O$R^{B2}$, or —N($R^{B2}$)C(O)N($R^{B2}$)$_2$, wherein each $R^{B2}$ is independently hydrogen or $C_{1-4}$alkyl.
(4b) $R^B$ is hydrogen, $C_{1-4}$alkyl, $C_{1-4}$haloalkyl, —$C_{1-4}$alkyl-$R^{B1}$, —C(O)$R^{B2}$, or —S(O)$_2$$R^{B2}$, wherein $R^{B1}$ is —C(O)O$R^{B3}$, —C(O)N($R^{B3}$)$_2$, —S(O)$_2$O$R^{B3}$, or —S(O)$_2$N($R^3$)$_2$, $R^{B2}$ is $C_{1-6}$ alkyl; and $R^{B3}$ is hydrogen or $C_{1-6}$ alkyl.
(4c) $R^B$ is hydrogen, $C_{1-4}$alkyl, or $C_{1-4}$haloalkyl.
(4d) $R^B$ is hydrogen or $C_{1-4}$alkyl;
(4e) $R^B$ is hydrogen.
(4f) $R^B$ is $C_{1-4}$alkyl.
(4g) $R^B$ is hydrogen, —C(O)$R^{B2}$, —C(O)(CH$_2$)$_{1-4}$CO-O$R^{B2}$, —C(O)C(NH$_2$)$R^D$, —P(O)(O$R^{B2}$)$_2$, —CH$_2$—OP(O)$_2$(OR)$_2$, —S(O)$_2$$R^{B2}$, —C(O)N($R^{B2}$)$_2$, —S(O)$_2$O$R^{B2}$, —S(O)$_2$N($R^3$)$_2$, wherein and $R^{B2}$ is hydrogen or $C_{1-4}$ alkyl.

$R^C$ is selected from one of the following groups (5a)-(5g):
(5a) $R^C$ is hydrogen or $C_{1-4}$alkyl.
(5b) $R^C$ is hydrogen or $C_{1-2}$alkyl.
(5c) $R^C$ is hydrogen or methyl.
(5d) $R^C$ is hydrogen.
(5e) $R^C$ is $C_{1-6}$alkyl.
(5f) $R^C$ is $C_{1-4}$alkyl.
(5g) $R^C$ is methyl.

$R^3$ is selected from one of the following groups (6a)-(6z):
(6a) $R^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl-, are each optionally substituted by one =$R^{32}$ group and one or two $R^{31}$ groups; and the aryl and heteroaryl groups, are each optionally substituted by one or two $R^{31}$ groups.
(6b) $R^3$ is aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{3-8}$cycloalkyl, $C_{3-8}$cycloalkenyl, 3-10 membered heterocyclyl, and $C_{3-8}$cycloalkyl$C_{1-6}$ alkyl-, are each optionally and independently substituted by one =$R^{32}$ group and each optionally and independently substituted by one or two $R^{31}$ groups; and the aryl and heteroaryl groups, are each optionally substituted by one or two $R^{31}$ groups.
(6c) $R^3$ is phenyl, a five or six membered heteroaryl, monocyclic $C_{5-8}$cycloalkyl, monocyclic $C_{5-8}$cycloalkenyl, a five or six membered monocyclic heterocyclyl, or (monocyclic $C_{5-8}$cycloalkyl)$C_{1-6}$ alkyl-, wherein the $C_{5-8}$cycloalkyl, $C_{5-8}$cycloalkenyl, 5-6 membered heterocyclyl, and $C_{5-8}$cycloalkyl$C_{1-6}$ alkyl-, are each optionally and independently substituted by one =$R^{32}$ group and each optionally and independently substituted by one or two $R^{31}$ groups; and the phenyl and heteroaryl groups, are each optionally substituted by one or two $R^{31}$ groups.
(6d) $R^3$ is phenyl or a five or six membered heteroaryl, each optionally substituted by one or two $R^{31}$ groups.
(6e) $R^3$ is monocyclic $C_{5-8}$cycloalkyl, monocyclic $C_{5-8}$cycloalkenyl, a five or six membered monocyclic heterocyclyl, or (monocyclic $C_{5-8}$cycloalkyl)$C_{1-6}$alkyl-, each optionally substituted by one =$R^{32}$ group and one or two $R^{31}$ groups.
(6f) $R^3$ is

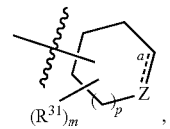

wherein bond a is a single bond or a double bond; m is 0, 1, or 2; p is 0 or 1; and wherein when bond a is a single bond, then Z is —C($R^{36}$)$_2$—, —C(=$R^{32}$)—, —N($R^{35}$)—, or —O—, wherein each $R^{36}$ is independently hydrogen or $R^{31}$; and $R^{35}$ is hydrogen, $C_{1-6}$alkyl, —C(O)R, —S(O)$_2$R, —C(O)OR, —C(O)N(R)$_2$, —S(O)$_2$OR, or —S(O)$_2$N(R)$_2$;

and when bond α is a double bond, then Z is —C($R^{36}$)= or —N=.

(6g) $R^3$ is

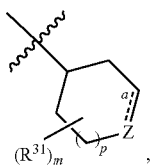

wherein bond a is a single bond or a double bond; m is 0, 1, or 2; p is 0 or 1; and wherein when bond a is a single bond, then Z is —C($R^{36}$)$_2$—, —C(=$R^{32}$)—, —N($R^{35}$)—, or —O—, wherein each $R^{36}$ is independently hydrogen or $R^{31}$; and $R^{35}$ is hydrogen, $C_{1-6}$alkyl, —C(O)R, —S(O)$_2$R, —C(O)OR, —C(O)N(R)$_2$, —S(O)$_2$OR, or —S(O)$_2$N(R)$_2$;

and when bond α is a double bond, then Z is —C($R^{36}$)= or —N=.

(6h) As group (6g), wherein when bond α is a single bond, then Z is —C($R^{36}$)$_2$— or —C(=$R^{32}$)—; and when bond a is a double bond, then Z is —C($R^{36}$)= or —N=.

(6i) As group (6g), wherein m is 0; when bond a is a single bond, then Z is —C($R^{36}$)$_2$— or —C(=$R^{32}$)—; and when bond a is a double bond, then Z is —C($R^{36}$)= or —N=.

(6j) As group (6g), wherein bond a is a single bond; and Z is —C($R^{36}$)$_2$— or —C(=$R^{32}$)—.

(6k) As group (6g), wherein bond a is a single bond; and Z is —C($R^{36}$)$_2$—.

(6l) As group (6g), wherein bond a is a single bond; and Z is —C(=$R^{32}$)—.

(6m) As group (6g), wherein m is 0; bond a is a single bond; and Z is —C($R^{36}$)$_2$— or —C(=$R^{32}$)—.

(6n) As group (6g), wherein m is 0; bond a is a single bond; and Z is —C($R^{36}$)$_2$—

(6o) As group (6g), wherein m is 0; bond a is a single bond; and Z is —C(=$R^{32}$)—.

(6p) As group (6g), wherein bond a is a single bond; and Z is —C($R^{36}$)$_2$— or —C(=$R^{32}$)—, wherein each $R^{36}$ is independently hydrogen, halogen, $C_{1-6}$alkyl, —$C_{1-6}$alkyl-OH, $C_{1-6}$haloalkyl, or —OH, wherein $R^{32}$ is =O, =C($R^{34}$)$_2$, =(spiro-$C_{3-8}$cycloalkyl), or =(spiro-(3-8 membered heterocyclyl)), wherein each $R^{34}$ is independently hydrogen, halogen, $C_{1-6}$alkyl, $C_{1-6}$haloalkyl, $C_{3-8}$cycloalkyl, or 3-8 membered heterocyclyl.

(6q) As group (6g), wherein m is 0; bond a is a single bond; and Z is —C($R^{36}$)$_2$— or —C(=$R^{32}$)—, wherein each $R^{36}$ is independently hydrogen, halogen, $C_{1-6}$alkyl, —$C_{1-6}$alkyl-OH, $C_{1-6}$haloalkyl, or —OH, wherein $R^{32}$ is =O, =C($R^{34}$)$_2$, =(spiro-$C_{3-8}$cycloalkyl), or =(spiro-(3-8 membered heterocyclyl)), wherein each $R^{34}$ is independently hydrogen, halogen, $C_{1-6}$alkyl, $C_{1-6}$haloalkyl, $C_{3-8}$cycloalkyl, or 3-8 membered heterocyclyl.

(6r) As group (6g), wherein bond a is a single bond; and Z is —N($R^{35}$)— or —O—.

(6s) $R^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{1-6}$alkyl, $C_{3-8}$cycloalkyl, $C_{3-8}$cycloalkenyl, 3-10 membered heterocyclyl, and $C_{3-8}$cycloalkyl $C_{1-6}$alkyl, are each optionally substituted by one =$R^{32}$ group and one or two $R^{31}$ groups;

the aryl and heteroaryl groups, are each optionally substituted by one or two $R^{31}$ groups; wherein each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR; and $R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl.

(6t) $R^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{1-6}$alkyl, $C_{3-8}$cycloalkyl, $C_{3-8}$cycloalkenyl, 3-10 membered heterocyclyl, and $C_{3-8}$cycloalkyl $C_{1-6}$alkyl-, are each optionally and independently substituted by one =$R^{32}$ group and each optionally and independently substituted by one or two $R^{31}$ groups; the aryl and heteroaryl groups, are each optionally substituted by one or two $R^{31}$ groups; wherein each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR;

and $R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl.

(6u) $R^3$ is aryl, heteroaryl, $C_{3-8}$cycloalkyl, $C_{3-8}$cycloalkenyl, or 3-10 membered heterocyclyl, wherein the $C_{3-8}$cycloalkyl, $C_{3-8}$cycloalkenyl, and 3-10 membered heterocyclyl are each optionally substituted by one =$R^{32}$ group and one, two, three, or four $R^{31}$ groups; and the aryl and heteroaryl are each optionally substituted by one, two, three, or four $R^{31}$ groups.

(6v) $R^3$ is phenyl, cyclopentyl, cyclohexyl, cyclohexenyl, furanyl, tetrahydropyranyl, piperidinyl, imidazolyl, thiazolyl, each optionally substituted by one, two, three, or four $R^{31}$ groups, and wherein the cyclopentyl, cyclohexyl, cyclohexenyl, and piperidinyl groups are each optionally substituted by one =$R^{32}$ group.

(6w) $R^3$ is phenyl, cyclopentyl, cyclohexyl, cyclohex-1-en-1-yl, cyclohex-3-en-1-yl, furan-2-yl, furan-3-yl, tetrahydropyran-3-yl, tetrahydropyran-4-yl, piperidin-3-yl, piperidin-4-yl, imidazol-2-yl, imidazol-4-yl, thiazol-2-yl, thiazol-4-yl, thiazol-5-yl, each optionally substituted by one or two $R^{31}$ groups, and wherein the cyclopentyl, cyclohexyl, cyclohexenyl, and piperidinyl groups are each optionally substituted by one =$R^{32}$ group.

(6x) Any one of groups (6a)-(6w), wherein each R is independently hydrogen, $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl-, heteroaryl $C_{1-6}$alkyl-, $C_{3-8}$ cycloalkyl$C_{1-6}$alkyl-, $C_{3-8}$cycloalkenyl$C_{1-6}$alkyl-, or (3-10 membered heterocyclyl) $C_{1-6}$alkyl-.

(6y) Any one of groups (6a)-(6w), wherein each R is independently hydrogen, $C_{1-6}$alkyl, $C_{1-6}$haloalkyl, phenyl, 5- or 6-membered heteroaryl, $C_{3-8}$cycloalkyl, $C_{3-8}$cycloalkenyl, 3-8 membered heterocyclyl, benzyl, (5- or 6-membered heteroaryl)$C_{1-6}$alkyl-, $C_{3-8}$cycloalkyl$C_{1-6}$alkyl-, $C_{3-8}$cycloalkenyl$C_{1-6}$alkyl-, or (3-8 membered heterocyclyl) $C_{1-6}$alkyl-.

(6z) Any one of groups (6a)-(6w), wherein each R is independently hydrogen or $C_{1-6}$alkyl.

In another embodiment, the invention provides the compound according to formula (VI),

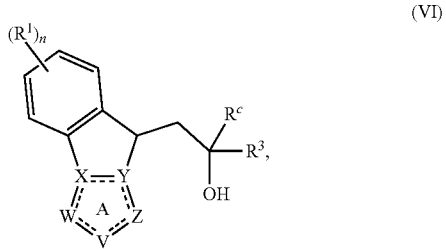

(VI)

or a pharmaceutically acceptable salt thereof, wherein n is 0 or 1;

ring A is an aromatic ring wherein
i) V and X are N, W and Z are CH and Y is C; or
ii) V, Y and Z are N, W is CH and X is C; or
iii) V, W and Y are N, X is C and Z is CH; or
iv) V and W are N or NH, X and Y are C and Z is CH;

each $R^1$ is independently halogen, —OR, —N(R)$_2$, or —SR;

$R^C$ is hydrogen or $C_{1-2}$alkyl; and each $R^3$ is independently hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{1-6}$alkyl, $C_{3-8}$cycloalkyl, $C_{3-8}$cycloalkenyl, 3-10 membered heterocyclyl, and $C_{3-8}$cycloalkyl $C_{1-6}$alkyl-, are each optionally and independently substituted by one $=R^{32}$ group and each optionally and independently substituted by one or two $R^{31}$ groups;

the aryl and heteroaryl groups, are each optionally substituted by one or two $R^{31}$ groups; wherein each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR;

$R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl; and each R is independently hydrogen or $R^{10}$, wherein $R^{10}$ is $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$alkyl-, each $R^{10}$ optionally substituted by one, two, three, or four groups that are each independently halogen, cyano, nitro, $C_{1-6}$alkyl, $C_{1-6}$haloalkyl, —$OR^{11}$, —$N(R^{11})_2$, —$SR^{11}$, —$C(O)OR^{11}$, —$C(O)N(R^{11})_2$, —$C(O)R^{11}$, —$S(O)R^{11}$, —$S(O)OR^{11}$, —$S(O)N(R^{11})_2$, —$S(O)_2R^{11}$, —$S(O)_2OR^{11}$, —$S(O)_2N(R^{11})_2$, —$OC(O)R^{11}$, —$OC(O)OR^{11}$, —$OC(O)N(R^{11})_2$, —$N(R^{11})C(O)R^{11}$, —$N(R^{11})C(O)OR^{11}$, —$N(R^{11})C(O)N(R^{11})_2$, wherein each $R^{11}$ is independently hydrogen or $C_{1-6}$alkyl.

In one embodiment, the compounds of formula (VI) further include those compounds where, $R^3$ is additionally (heteroaryl)-(3-10 membered heterocyclyl)-;

$R^{31}$ is additionally —C(O)N(OH)R, —C(N=$R^{11}$)R, or —C(N=$R^{11}$)N($R^{11}$)R;

$R^{34}$ is additionally cyano or —$C_{1-6}$alkyl-OR; and/or $R^{10}$ is additionally optionally substituted by —$N(R^{11})S(O)_2R^{11}$ or —C(O)-(3-10 membered heterocyclyl);

such compounds are referred to as compounds of formula (VI').

The invention further comprises subgenera of formula (VI) or (VI') in which the substituents are selected as any and all combinations of one or more of structural formula (VI), n, $R^1$, $R^3$, and $R^C$ as defined herein, including without limitation, the following:

Structural Formula VI is One of Formulae (VIa)-(VId):

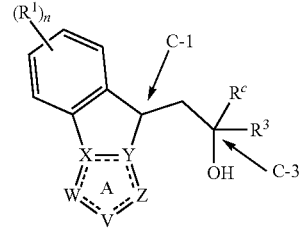

(VIa): wherein the stereoisomeric configuration of carbon-1 (C-1) and carbon-3 (C-3) of formula (VI) are respectively (R, R).

(VIb): wherein the stereoisomeric configuration of carbon-1 and carbon-3 are of formula (VI) respectively (R, S).

(VIc): wherein the stereoisomeric configuration of carbon-1 and carbon-3 are of formula (VI) respectively (S, R).

(VId): wherein the stereoisomeric configuration of carbon-1 and carbon-3 are of formula (VI) respectively (S, S).

Structural Formula VI is One of Formulae (VIe)-(VIh):

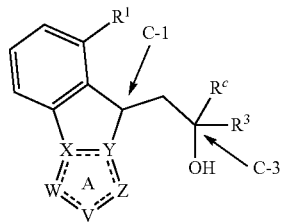

(VIe): wherein the stereoisomeric configuration of carbon-1 (C-1) and carbon-3 (C-3) of formula (VI) are respectively (R, R).

(VIf): wherein the stereoisomeric configuration of carbon-1 and carbon-3 are of formula (VI) respectively (R, S).

(VIg): wherein the stereoisomeric configuration of carbon-1 and carbon-3 are of formula (VI) respectively (S, R).

(VIh): wherein the stereoisomeric configuration of carbon-1 and carbon-3 are of formula (VI) respectively (S, S).

Structural Formula VI is One Wherein n and $R^1$ are Selected from One of the Following Groups (7a)-(7e):
- (7a) n is 0 or 1 and $R^1$ is halogen, —$OR^O$,
- (7b) n is 0 or 1 and $R^1$ is fluoro, chloro, hydroxy, or methoxy.
- (7c) n is 0 or 1 and $R^1$ is halogen.
- (7d) n is 0 or 1 and $R^1$ is fluoro or chloro.
- (7e) n is 0

Structural Formula VI is One Wherein $R^C$ is Selected from One of the Following Groups (8a)-(8g):
- (8a) $R^C$ is hydrogen or $C_{1-4}$alkyl.
- (8b) $R^C$ is hydrogen or $C_{1-2}$alkyl.
- (8c) $R^C$ is hydrogen or methyl.
- (8d) $R^C$ is hydrogen.
- (8e) $R^C$ is $C_{1-6}$alkyl.
- (8f) $R^C$ is $C_{1-4}$alkyl.
- (8g) $R^C$ is methyl.

Structural Formula VI is One Wherein $R^3$ is Selected from One of the Following Groups (9a)-(9x):
- (9a) $R^3$ is aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{3-8}$cycloalkyl, $C_{3-8}$cycloalkenyl, 3-10 membered heterocyclyl, and $C_{3-8}$cycloalkyl$C_{1-6}$ alkyl-, are each optionally and independently substituted by one =$R^{32}$ group and each optionally and independently substituted by one or two $R^{31}$ groups; and the aryl and heteroaryl groups, are each optionally substituted by one or two $R^{31}$ groups.
- (9b) $R^3$ is phenyl, a five or six membered heteroaryl, monocyclic $C_{5-8}$cycloalkyl, monocyclic $C_{5-8}$cycloalkenyl, a five or six membered monocyclic heterocyclyl, or (monocyclic $C_{5-8}$cycloalkyl)$C_{1-6}$ alkyl-, wherein the $C_{5-8}$cycloalkyl, $C_{5-8}$cycloalkenyl, 5-6 membered heterocyclyl, and $C_{5-8}$cycloalkyl$C_{1-6}$ alkyl-, are each optionally and independently substituted by one =$R^{32}$ group and each optionally and independently substituted by one or two $R^{31}$ groups; and the phenyl and heteroaryl groups, are each optionally substituted by one or two $R^{31}$ groups.
- (9c) $R^3$ is phenyl or a five or six membered heteroaryl, each optionally substituted by one or two $R^{31}$ groups.
- (9d) $R^3$ is monocyclic $C_{5-8}$cycloalkyl, monocyclic $C_{5-8}$cycloalkenyl, a five or six membered monocyclic heterocyclyl, or (monocyclic $C_{5-8}$cycloalkyl)$C_{1-6}$alkyl-, each optionally substituted by one =$R^{32}$ group and one or two $R^{31}$ groups.
- (9e) $R^3$ is

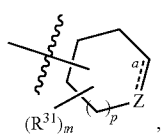

wherein bond a is a single bond or a double bond; m is 0, 1, or 2; p is 0 or 1; and wherein
when bond a is a single bond, then Z is —$C(R^{36})_2$—, —$C(=R^{32})$—, —$N(R^{35})$—, or —O—, wherein each $R^{36}$ is independently hydrogen or $R^{31}$; and
$R^{35}$ is hydrogen, $C_{1-6}$alkyl, —C(O)R, —S(O)$_2$R, —C(O)OR, —C(O)N(R)$_2$, —S(O)$_2$OR, or —S(O)$_2$N(R)$_2$;
and when bond a is a double bond, then Z is —$C(R^{36})$= or —N=.

- (9f) $R^3$ is

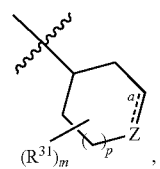

wherein bond a is a single bond or a double bond; m is 0, 1, or 2;
p is 0 or 1; and wherein
when bond a is a single bond, then Z is —$C(R^{36})_2$—, —$C(=R^{32})$—, —$N(R^{35})$—, or —O—, wherein each $R^{36}$ is independently hydrogen or $R^{31}$; and
$R^{35}$ is hydrogen, $C_{1-6}$alkyl, —C(O)R, —S(O)$_2$R, —C(O)OR, —C(O)N(R)$_2$, —S(O)$_2$OR, or —S(O)$_2$N(R)$_2$;
and when bond a is a double bond, then Z is —$C(R^{36})$= or —N=.

- (9g) As group (9f), wherein when bond a is a single bond, then Z is —$C(R^{36})_2$— or —$C(=R^{32})$—; and when bond a is a double bond, then Z is —$C(R^{36})$= or —N=.
- (9h) As group (9f), wherein m is 0; when bond a is a single bond, then Z is —$C(R^{36})_2$— or —$C(=R^{32})$—; and when bond a is a double bond, then Z is —$C(R^{36})$= or —N=.
- (9i) As group (9f), wherein bond a is a single bond; and Z is —$C(R^{36})_2$— or —$C(=R^{32})$—.
- (9j) As group (9f), wherein bond a is a single bond; and Z is —$C(R^{36})_2$—.
- (9k) As group (9f), wherein bond a is a single bond; and Z is —$C(=R^{32})$—.
- (9l) As group (9f), wherein m is 0; bond a is a single bond; and Z is —$C(R^{36})_2$— or —$C(=R^{32})$—.
- (9m) As group (9f), wherein m is 0; bond a is a single bond; and Z is —$C(R^{36})_2$—
- (9n) As group (9f), wherein m is 0; bond a is a single bond; and Z is —$C(=R^{32})$—.
- (9o) As group (9f), wherein bond a is a single bond; and Z is —$C(R^{36})_2$— or —$C(=R^{32})$—, wherein each $R^{36}$ is independently hydrogen, halogen, $C_{1-6}$alkyl, —$C_{1-6}$alkyl-OH, $C_{1-6}$haloalkyl, or —OH, wherein $R^{32}$ is =O, =$C(R^{34})_2$, =(spiro-$C_{3-8}$cycloalkyl), or =(spiro-(3-8 membered heterocyclyl)), wherein each $R^{34}$ is independently hydrogen, halogen, $C_{1-6}$alkyl, $C_{1-6}$haloalkyl, $C_{3-8}$cycloalkyl, or 3-8 membered heterocyclyl.
- (9p) As group (9f), wherein m is 0; bond a is a single bond; and Z is —$C(R^{36})_2$— or —$C(=R^{32})$—, wherein each $R^{36}$ is independently hydrogen, halogen, $C_{1-6}$alkyl, —C120300456alkyl-OH, $C_{1-6}$haloalkyl, or —OH, wherein $R^{32}$ is =O, =$C(R^{34})_2$, =(spiro-$C_{3-8}$cycloalkyl), or =(spiro-(3-8 membered heterocyclyl)), wherein each $R^{34}$ is independently hydrogen, halogen, $C_{1-6}$alkyl, $C_{1-6}$haloalkyl, $C_{3-8}$cycloalkyl, or 3-8 membered heterocyclyl.
- (9q) As group (9f), wherein bond a is a single bond; and Z is —$N(R^{35})$— or —O—.
- (9r) $R^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl, wherein the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$ alkyl, are each optionally substituted by one =$R^{32}$ group and one or two $R^{31}$ groups;

the aryl and heteroaryl groups, are each optionally substituted by one or two $R^{31}$ groups; wherein each $R^{31}$ is independently halogen, cyano, nitro, $C_{1-6}$alkyl, —$C_{1-6}$alkyl-$R^{33}$, C120300456haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR; and $R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl.

(9s) $R^3$ is aryl, heteroaryl, $C_{3-8}$cycloalkyl, $C_{3-8}$cycloalkenyl, or 3-10 membered heterocyclyl, wherein the $C_{3-8}$cycloalkyl, $C_{3-8}$cycloalkenyl, and 3-10 membered heterocyclyl are each optionally substituted by one =$R^{32}$ group and one, two, three, or four $R^{31}$ groups; and the aryl and heteroaryl are each optionally substituted by one, two, three, or four $R^{31}$ groups.

(9t) $R^3$ is phenyl, cyclopentyl, cyclohexyl, cyclohexenyl, furanyl, tetrahydropyranyl, piperidinyl, imidazolyl, thiazolyl, each optionally substituted by one, two, three, or four $R^{31}$ groups, and wherein the cyclopentyl, cyclohexyl, cyclohexenyl, and piperidinyl groups are each optionally substituted by one =$R^{32}$ group.

(9u) $R^3$ is phenyl, cyclopentyl, cyclohexyl, cyclohex-1-en-1-yl, cyclohex-3-en-1-yl, furan-2-yl, furan-3-yl, tetrahydropyran-3-yl, tetrahydropyran-4-yl, piperidin-3-yl, piperidin-4-yl, imidazol-2-yl, imidazol-4-yl, thiazol-2-yl, thiazol-4-yl, thiazol-5-yl, each optionally substituted by one or two $R^{31}$ groups, and wherein the cyclopentyl, cyclohexyl, cyclohexenyl, and piperidinyl groups are each optionally substituted by one =$R^{32}$ group.

(9v) Any one of groups (9a)-(9u), wherein each R is independently hydrogen, $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$ cycloalkyl$C_{1-6}$alkyl-, $C_{3-8}$cycloalkenyl$C_{1-6}$alkyl-, or (3-10 membered heterocyclyl)$C_{1-6}$alkyl-.

(9w) Any one of groups (9a)-(9u), wherein each R is independently hydrogen, $C_{1-6}$alkyl, $C_{1-6}$haloalkyl, phenyl, 5- or 6-membered heteroaryl, $C_{3-8}$cycloalkyl, $C_{3-8}$cycloalkenyl, 3-8 membered heterocyclyl, benzyl, (5- or 6-membered heteroaryl)$C_{1-6}$alkyl-, $C_{3-8}$ cycloalkyl$C_{1-6}$alkyl-, $C_{3-8}$cycloalkenyl$C_{1-6}$alkyl-, or (3-8 membered heterocyclyl)$C_{1-6}$alkyl-.

(9x) Any one of groups (9a)-(9u), wherein each R is independently hydrogen or $C_{1-6}$alkyl.

In another embodiment, the invention provides the compound according to formula (VII),

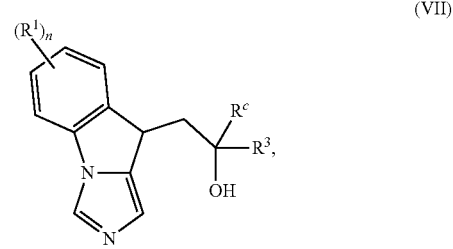

(VII)

or a pharmaceutically acceptable salt thereof, wherein n is 0 or 1;

each $R^1$ is independently halogen, —OR, —N(R)$_2$, or —SR;

$R^C$ is hydrogen or $C_{1-2}$alkyl; and each $R^3$ is independently hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl-, are each optionally and independently substituted by one =$R^{32}$ group and each optionally and independently substituted by one or two $R^{31}$ groups;

the aryl and heteroaryl groups, are each optionally substituted by one or two $R^{31}$ groups; wherein each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O) R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR;

$R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl; and each R is independently hydrogen or $R^{10}$, wherein $R^{10}$ is $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$ cycloalkyl$C_{1-6}$alkyl-, $C_{3-8}$cycloalkenyl$C_{1-6}$alkyl-, or (3-10 membered heterocyclyl)$C_{1-6}$alkyl-, each $R^{10}$ optionally substituted by one, two, three, or four groups that are each independently halogen, cyano, nitro, $C_{1-6}$alkyl, $C_{1-6}$haloalkyl, —OR$^{11}$, —N($R^{11}$)$_2$, —SR$^{11}$, —C(O)OR$^{11}$, —C(O)N($R^{11}$)$_2$, —C(O)R$^{11}$, —S(O)R$^{11}$, —S(O)OR$^{11}$, —S(O)N($R^{11}$)$_2$, —S(O)$_2$R$^{11}$, —S(O)$_2$OR$^{11}$, —S(O)$_2$N($R^{11}$)$_2$, —OC(O)R$^{11}$, —OC (O)OR$^{11}$, —OC(O)N($R^{11}$)$_2$, —N($R^{11}$)C(O)R$^{11}$, —N($R^{11}$)C(O)OR$^{11}$, —N($R^{11}$)C(O)N($R^{11}$)$_2$, wherein each $R^{11}$ is independently hydrogen or $C_{1-6}$alkyl.

The invention further comprises subgenera of formula (VII) in which the substituents are selected as any and all combinations of one or more of structural formula (VII), n, $R^1$, $R^3$, and $R^C$ as defined herein, including without limitation, the following:

Structural Formula VII is One of Formulae (VIIa)-(VIId):

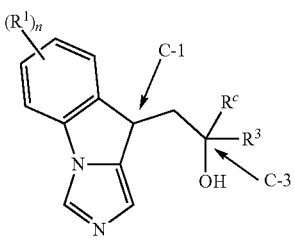

(VIIa): wherein the stereoisomeric configuration of carbon-1 (C-1) and carbon-3 (C-3) of formula (VII) are respectively (R, R).

(VIIb): wherein the stereoisomeric configuration of carbon-1 and carbon-3 are of formula (VII) respectively (R, S).

(VIIc): wherein the stereoisomeric configuration of carbon-1 and carbon-3 are of formula (VII) respectively (S, R).

(VIId): wherein the stereoisomeric configuration of carbon-1 and carbon-3 are of formula (VII) respectively (S, S).

Structural Formula VII is one wherein n and $R^1$ are selected from one of the previous groups (7a)-(7d):

Structural Formula VII is one wherein $R^C$ is selected from one of the previous groups (8a)-(8c):

Structural Formula VII is one wherein $R^3$ is selected from one of the previous groups (9a)-(9x):

In another embodiment, the invention provides the compound according to formula (VIII),

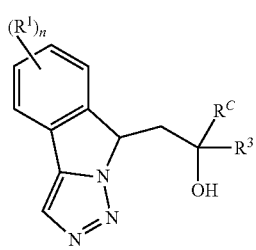

(VIII)

or a pharmaceutically acceptable salt thereof, wherein
n is 0 or 1;
each $R^1$ is independently halogen, —OR, —N(R)$_2$, or —SR;
$R^C$ is hydrogen or $C_{1-2}$alkyl; and
each $R^3$ is independently hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein
the $C_{1-6}$alkyl, $C_{3-8}$cycloalkyl, $C_{3-8}$cycloalkenyl, 3-10 membered heterocyclyl, and $C_{3-8}$cycloalkyl $C_{1-6}$alkyl-, are each optionally and independently substituted by one =$R^{32}$ group and each optionally and independently substituted by one or two $R^{31}$ groups;
the aryl and heteroaryl groups, are each optionally substituted by one or two $R^{31}$ groups; wherein
each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)R, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R,
—N(R)C(O)OR, —N(R)C(O)N(R)$_2$, wherein $R^{33}$ is —OR, —N(R)$_2$, or —SR;
$R^{32}$ is oxo, =C(R$^{34}$)$_2$, =(spiro-C$_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl; and
each R is independently hydrogen or $R^{10}$, wherein
$R^{10}$ is $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$alkyl-, each $R^{10}$ optionally substituted by one, two, three, or four groups that are each independently halogen, cyano, nitro, $C_{1-6}$alkyl, $C_{1-6}$haloalkyl, —OR$^{11}$, —N(R$^{11}$)$_2$, —SR$^{11}$, —C(O)OR$^{11}$, —C(O)N(R$^{11}$)$_2$, —C(O)R$^{11}$, —S(O)R$^{11}$, —S(O)OR$^{11}$, —S(O)N(R$^{11}$)$_2$, —S(O)$_2$R$^{11}$, —S(O)$_2$OR$^{11}$, —S(O)$_2$N(R$^{11}$)$_2$, —OC(O)R$^{11}$, —OC(O)OR$^{11}$, —OC(O)N(R$^{11}$)$_2$, —N(R$^{11}$)C(O)R$^{11}$, —N(R$^{11}$)C(O)OR$^{11}$, —N(R$^{11}$)C(O)N(R$^{11}$)$_2$, wherein each $R^{11}$ is independently hydrogen or $C_{1-6}$alkyl.

The invention further comprises subgenera of formula (VIII) in which the substituents are selected as any and all combinations of one or more of structural formula (VIII), n, $R^1$, $R^3$, and $R^C$ as defined herein, including without limitation, the following:

Structural Formula VIII is One of Formulae (VIIIa)-(VIIId):

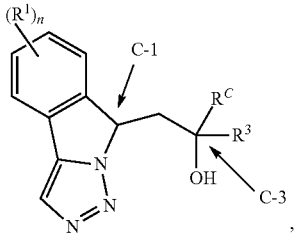

(VIIIa): wherein the stereoisomeric configuration of carbon-1 (C-1) and carbon-3 (C-3) of formula (VIII) are respectively (R, R).

(VIIIb): wherein the stereoisomeric configuration of carbon-1 and carbon-3 are of formula (VIII) respectively (R, S).

(VIIIc): wherein the stereoisomeric configuration of carbon-1 and carbon-3 are of formula (VIII) respectively (S, R).

(VIIId): wherein the stereoisomeric configuration of carbon-1 and carbon-3 are of formula (VIII) respectively (S, S).

Structural Formula VIII is one wherein n and $R^1$ are selected from one of the previous groups (7a)-(7d).

Structural Formula VIII is one wherein $R^C$ is selected from one of the previous groups (8a)-(8c).

Structural Formula VIII is one wherein $R^3$ is selected from one of the previous groups (9a)-(9x).

In another embodiment, the invention provides the compound according to formula (IX),

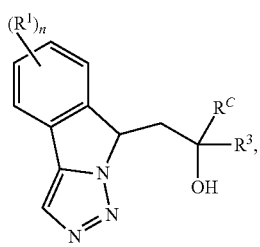

(IX)

or a pharmaceutically acceptable salt thereof, wherein
n is 0 or 1;
each $R^1$ is independently halogen, —OR, —N(R)$_2$, or —SR;
$R^C$ is hydrogen or $C_{1-2}$alkyl; and
each $R^3$ is independently hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein
    the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl-, are each optionally and independently substituted by one =$R^{32}$ group and each optionally and independently substituted by one or two $R^{31}$ groups;
    the aryl and heteroaryl groups, are each optionally substituted by one or two $R^{31}$ groups; wherein
        each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR;
        $R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl; and
each R is independently hydrogen or $R^{10}$, wherein
    $R^{10}$ is $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$alkyl-, each $R^{10}$ optionally substituted by one, two, three, or four groups that are each independently halogen, cyano, nitro, $C_{1-6}$alkyl, $C_{1-6}$haloalkyl, —OR$^{11}$, —N($R^{11}$)$_2$, —SR$^{11}$, —C(O)OR$^{11}$, —C(O)N($R^{11}$)$_2$, —C(O)R$^{11}$, —S(O)R$^{11}$, —S(O)OR$^{11}$, —S(O)N($R^{11}$)$_2$, —S(O)$_2$R$^{11}$, —S(O)$_2$OR$^{11}$, —S(O)$_2$N($R^{11}$)$_2$, —OC(O)R$^{11}$, —OC(O)OR$^{11}$, —OC(O)N($R^{11}$)$_2$, —N($R^{11}$)C(O)R$^{11}$, —N($R^{11}$)C(O)OR$^{11}$, —N($R^{11}$)C(O)N($R^{11}$)$_2$, wherein each $R^{11}$ is independently hydrogen or $C_{1-6}$alkyl.

The invention further comprises subgenera of formula (IX) in which the substituents are selected as any and all combinations of one or more of structural formula (IX), n, $R^1$, $R^3$, and $R^C$ as defined herein, including without limitation, the following:

Structural Formula IX is One of Formulae (IXa)-(IXd):

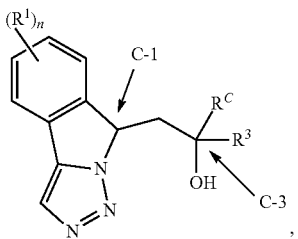

(IXa): wherein the stereoisomeric configuration of carbon-1 (C-1) and carbon-3 (C-3) of formula (IX) are respectively (R, R).
(IXb): wherein the stereoisomeric configuration of carbon-1 and carbon-3 are of formula (IX) respectively (R, S).
(IXc): wherein the stereoisomeric configuration of carbon-1 and carbon-3 are of formula (IX) respectively (S, R).
(IXd): wherein the stereoisomeric configuration of carbon-1 and carbon-3 are of formula (IX) respectively (S, S).
Structural Formula IX is one wherein n and $R^1$ are selected from one of the previous groups (7a)-(7d).
Structural Formula IX is one wherein $R^C$ is selected from one of the previous groups (8a)-(8c).
Structural Formula IX is one wherein $R^3$ is selected from one of the previous groups (9a)-(9x).

In another embodiment, the invention provides the compound according to formula (X) and its tautomer,

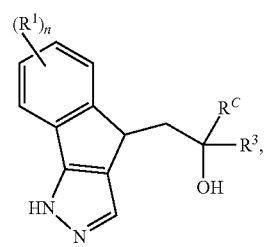

(X)

or a pharmaceutically acceptable salt thereof, wherein
n is 0 or 1;
each $R^1$ is independently halogen, —OR, —N(R)$_2$, or —SR;
$R^C$ is hydrogen or $C_{1-2}$alkyl; and
each $R^3$ is independently hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein
    the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl-, are each optionally and independently substituted by one =$R^{32}$ group and each optionally and independently substituted by one or two $R^{31}$ groups;
    the aryl and heteroaryl groups, are each optionally substituted by one or two $R^{31}$ groups; wherein
        each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$,
            wherein $R^{33}$ is —OR, —N(R)$_2$, or —SR; $R^{32}$ is oxo, =C($R^{34}$)$_2$, =(spiro-$C_{3-8}$cycloalkyl), or =(spiro-(3-

10 membered heterocyclyl)), wherein each $R^{34}$ is independently hydrogen, halogen, $C_{1-6}$alkyl, or $C_{3-8}$cycloalkyl; and each R is independently hydrogen or $R^{10}$, wherein
$R^{10}$ is $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$alkyl-, each $R^{10}$ optionally substituted by one, two, three, or four groups that are each independently halogen, cyano, nitro, $C_{1-6}$alkyl, $C_{1-6}$haloalkyl, —$OR^{11}$, —$N(R^{11})_2$, —$SR^{11}$, —$C(O)OR^{11}$, —$C(O)N(R^{11})_2$, —$C(O)R^{11}$, —$S(O)R^{11}$, —$S(O)OR^{11}$, —$S(O)N(R^{11})_2$, —$S(O)_2R^{11}$, —$S(O)_2OR^{11}$, —$S(O)_2N(R^{11})_2$, —$OC(O)R^{11}$, —$OC(O)OR^{11}$, —$OC(O)N(R^{11})_2$, —$N(R^{11})C(O)R^{11}$, —$N(R^{11})C(O)OR^{11}$, —$N(R^{11})C(O)N(R^{11})_2$, wherein each $R^{11}$ is independently hydrogen or $C_{1-6}$alkyl.

The invention further comprises subgenera of formula (X) in which the substituents are selected as any and all combinations of one or more of structural formula (X), n, $R^1$, $R^3$, and $R^C$ as defined herein, including without limitation, the following:

Structural Formula X is One of Formulae (Xa)-(Xd):

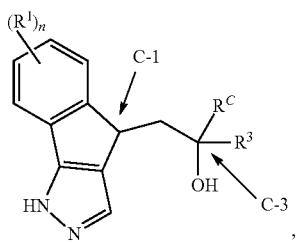

(Xa): wherein the stereoisomeric configuration of carbon-1 (C-1) and carbon-3 (C-3) of formula (X) are respectively (R, R).

(Xb): wherein the stereoisomeric configuration of carbon-1 and carbon-3 are of formula (X) respectively (R, S).

(Xc): wherein the stereoisomeric configuration of carbon-1 and carbon-3 are of formula (X) respectively (S, R).

(Xd): wherein the stereoisomeric configuration of carbon-1 and carbon-3 are of formula (X) respectively (S, S).

Structural Formula X is one wherein n and $R^1$ are selected from one of the previous groups (7a)-(7d).

Structural Formula X is one wherein $R^C$ is selected from one of the previous groups (8a)-(8c).

Structural Formula X is one wherein $R^3$ is selected from one of the previous groups (9a)-(9x).

In another aspect, the present disclosure provides compounds and pharmaceutical compositions comprising the compounds according to any one of the preceding aspects of the invention or any embodiment thereof, together with a pharmaceutically acceptable excipient, diluent, or carrier.

In another aspect, the invention provides methods for treating indoleamine 2,3-dioxygenase (IDO) or tryptophan 2,3-dioxygenase (TDO) mediated immunosuppression in a subject in need thereof, comprising administering an effective indoleamine 2,3-dioxygenase inhibiting amount of a compound or a pharmaceutical composition according to any of the preceding aspects of the invention or any embodiment thereof.

In one embodiment, the immunosuppression is associated with an infectious disease, or cancer.

In another embodiment, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In another embodiment, the immunosuppression is immunosuppression associated with HIV-1 infection.

In another embodiment, the immunosuppression is associated with a cancer.

In an embodiment, the immunosuppression is tumor-specific immunosuppression associated with cancer.

In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the invention provides the use of compounds described by any one of the preceding aspects (and any embodiment thereof), as defined above, for the preparation of a medicament for the treatment of medical conditions that benefit from the inhibition of enzymatic activity of indoleamine-2,3-dioxygenase or tryptophan-2,3-dioxygenase. Medical conditions contemplated in this aspect include all the conditions described herein.

In another aspect, the invention provides a use of compounds described by any one of the preceding aspects (and any embodiment thereof), as defined above, for the preparation of a medicament to stimulate T cell proliferation or to reverse an immunologic state of anergy or immunosuppression.

In one embodiment, the anergy or immunosuppression is caused by expression of the enzyme indoleamine-2,3-dioxygenase.

In one embodiment, the anergy or immunosuppression is caused by expression of the enzyme tryptophan-2,3-dioxygenase.

In another aspect, the invention provides the use of compounds described by any one of the preceding aspects (and any embodiment thereof), as defined above, for the preparation of a medicament for the treatment of immunosuppression associated with cancer, infectious diseases, or viral infections.

In one embodiment, the invention provides the use of compounds described in to any one of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

In another embodiment, the invention provides the use of compounds described in any of the preceding aspects (and any embodiment thereof), as defined above, and embodiments thereof as defined above, for the preparation of a medicament for the treatment of infectious diseases where the infectious disease is a viral infection. Preferably, the viral infection is selected from the group consisting of: influenza, hepatitis C virus (HCV), human papilloma virus (HPV), cytomegalovirus (CMV), Epstein-Barr virus (EBV), varicella zoster virus, poliovirus, coxsackie virus, and human immunodeficiency virus (HIV). More preferably, the viral infection is human immunodeficiency virus (HIV).

Definitions

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "-alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The term "nitro" as used herein, means a —NO₂ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "spiro" as used herein refers to a cyclic moiety formed by the substituted atom and two available substitutable positions on that same atom. For example, moiety such as

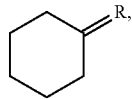

where R is a spiro-cycloalkyl= group includes compounds such as

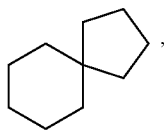

where the spiro-cyclopentyl group is the R group attached to the parent cyclohexyl ring by two single bonds. Similarly, where R is a spiro-heterocyclyl group, such compounds include

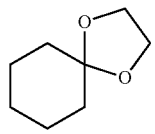

where the spiro-1,3-dioxolanyl ring is the R group attached to the parent cyclohexyl ring by two single bonds.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound includes the administration of a compound described herein to an individual or patient, such as a human, having IDO, as well as, for example, introducing a compound into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., IDO modulation or tryptophan degradation inhibition).

Manifestation of amelioration of a disease condition with underlying IDO-mediated immunosuppression may require the concomitant or sequential administration of additional therapeutic agents, such as antineoplastic agents in the case of cancer, or antiretroviral agents in the case of viral diseases. For example, administration of IDO inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme indoleamine-2,3-dioxygenase (IDO). The term "modulate" is meant to refer to an ability to decrease activity of an enzyme or receptor. Accordingly, compounds described herein can be used in methods of modulating IDO by contacting the enzyme with any one or more of the compounds or compositions described herein. In some embodiments, the compounds described herein can act as inhibitors of IDO. In further embodiments, the compounds described herein can be used to modulate activity of IDO in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing IDO such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods for treating immunosuppression associated with an infectious disease, e.g., HIV-1 infection, in a patient by administering to the patient an effective amount of a compound or composition recited herein.

For example, IDO-mediated immunosuppression associated with viral infection, is associated with a viral infection selected from the group consisting of: influenza, hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

Further provided are methods of treating diseases associated with activity or expression, including abnormal activity and/or overexpression, of IDO in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity.

Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds and pharmaceutical compositions described herein for treatment of IDO-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Therapeutic agents that constitute the standard of care for a particular cancer type or infectious disease are expected to benefit when combined with IDO inhibitors of the present invention. For example, for the case of tumors, is it preferable that the tumor is sensitive to the cytotoxic effects of the chemotherapeutic agent in order to stimulate the release of antigens that will eventually mediate an immune response that will be enhanced by addition of IDO inhibitors to the combination treatment. A person of skill in the art will know how to select such chemotherapeutic agent based on the clinical characteristics and known sensitivity of each tumor to different antineoplastic agents.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimid-inedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT- 378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxyco-formycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4,4-1BB and PD-1, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60F-254). The developed TLC plates were visualized by short wave UV light (254 nm) or immersion in potassium permanganate solution followed by heating on a hot plate. Flash chromatography was performed with Selecto Scientific silica gel, 32-63 μm particle sizes. All reactions were performed in flame or oven-dried glassware under a nitrogen atmosphere. All reactions were stirred magnetically at ambient temperature unless otherwise indicated. 1H NMR spectra were obtained with a Bruker DRX400, Varian VXR400 or VXR300. 1H NMR spectra were reported in parts per million (δ) relative to TMS (0.0), DMSO-d6 (2.50) or CD3OD (4.80) as an internal reference. All 1H NMR spectra were taken in CDCl3 unless otherwise indicated. The phosphonates were prepared according to the literature procedure: (U.S. Pat. No. 5,807,892 A1, 1998; Patent: US2012/033245; Patent: US2008/306084 A1, 2008). 1-(azidomethyl)-2,4-dimethoxybenzene was synthesized according to ChemMedChem, 2011, vol. 6, #5, 840-847.

Example 1 General Procedure for the Synthesis of Substituted 3-(2-Bromophenyl)prop-2-en-1-ones by Aldol Condensation

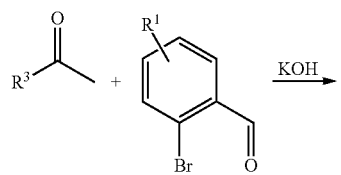

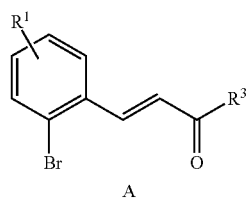

To a mixture of appropriate the benzaldehyde (32.43 mmol) and acetyl derivative (32.43 mmol) in ethanol (100 mL) at rt, powdered potassium hydroxide (4.86 mmol) is added and the mixture is stirred overnight. The solvent is distilled off and the crude is diluted with water (40 mL) and tert-butylmethyl ether (100 mL). The organic layer is separated and the aqueous layer is extracted with tert-butylmethyl ether (2×100 mL). The combined organic extract is dried over sodium sulfate and concentrated under reduced pressure to afford the crude. Chromatographic purification affords the following compounds.

| # | Compound | Name |
|---|----------|------|
| 1 | | (E)-3-(2-bromophenyl)-1-cyclohexylprop-2-en-1-one |
| 2 | | (E)-3-(2-bromophenyl)-1-(1-(2-phenylacetyl)piperidin-4-yl)prop-2-en-1-one |
| 3 | | (E)-3-(2-bromophenyl)-1-(1-(2-(4-(trifluoromethyl)phenyl)acetyl)piperidin-4-yl)prop-2-en-1-one |
| 4 | | (E)-3-(2-bromophenyl)-1-(1-(2-(tetrahydro-2H-pyran-4-yl)acetyl)piperidin-4-yl)propyl-2-en-1-one |
| 5 | | (E)-3-(2-bromophenyl)-1-(4-methylenecyclohexyl)prop-2-en-1-one |

-continued

| # | Compound | Name |
|---|---|---|
| 6 | | (E)-1-(4-((benzyloxy)methyl)cyclohexyl)-3-(2-bromophenyl)prop-2-en-1-one |
| 7 | | (E)-3-(2-bromophenyl)-1-(cyclohex-3-en-1-yl)prop-2-en-1-one |
| 8 | | (E)-3-(2-bromophenyl)-1-cyclopentylprop-2-en-1-one |
| 9 | | (E)-3-(2-bromophenyl)-1-(pyridin-4-yl)prop-2-en-1-one |
| 10 | | (E)-3-(2-bromophenyl)-1-(1,4-dioxaspiro[4.5]decan-8-yl)prop-2-en-1-one |
| 11 | | (E)-3-(2-bromophenyl)-1-(thiazol-5-yl)prop-2-en-1-one |
| 12 | | (E)-3-(2-bromophenyl)-1-(2,4-dimethylfuran-3-yl)prop-2-en-1-one |
| 13 | | (E)-3-(2-bromophenyl)-1-(3-chlorophenyl)prop-2-en-1-one |

Example 2 General Procedure for the Michael Addition of (1-Trityl-1H-imidazol-4-yl)magnesium bromide to Substituted 3-(2-bromophenyl)prop-2-en-1-ones

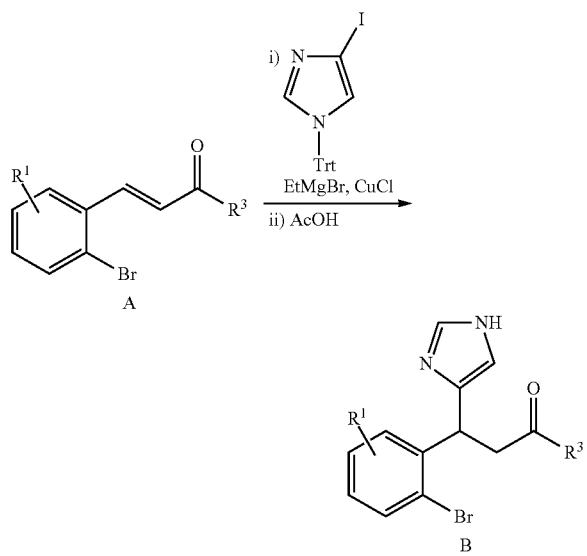

To a solution of 4-iodotritylimidazole (19.10 mmol) in tetrahydrofuran (100 mL) at rt EtMgBr (19.10 mmol, 21.22 mL, 0.9 M solution in THF) is added dropwise and the solution stirred at rt for 2 h. The solution is cooled to −15° C. and added to a cooled (−15° C.) solution of the appropriate 3-(2-bromoaryl)prop-2-en-1-one (19.10 mmol) and CuCl (3.82 mmol) in THF (80 mL) via cannula. The reaction is allowed to warm to rt and stirred overnight. The solvent is removed under reduced pressure and the crude is partitioned between saturated $NH_4Cl$ (80 mL) solution and dichloromethane (100 mL). The solution is stirred for 10 minutes the layers are separated and the aqueous layer is extracted with dichloromethane (2×100 mL). The combined organic extracts are washed with water (2×50 mL), dried over $Na_2SO_4$ and concentrated to afford a white solid. The crude product is diluted with acetic acid (10 mL) and heated at 90° C. in methanol (50 mL) for 2 h. After cooling to rt the solvent is removed under reduced pressure and the crude is basified with sat $NaHCO_3$ solution and diluted with water (30 mL) and $CH_2Cl_2$ (50 mL). The organic layer is separated and the product is extracted with $CH_2Cl_2$ (3×50 mL). The combined organic extracts are washed with brine (30 mL×1), dried over $Na_2SO_4$ and concentrated to afford a crude residue. The crude residue is subjected to purification by column chromatography and converted to its HCl salt. The solvent is removed and the solid is crystallized from a mixture of methanol and ethyl acetate to afford the following compounds. The product is basified with $NaHCO_3$ for the next step

| # | Compound | Name | Yield |
|---|---|---|---|
| 14 | | 3-(2-bromophenyl)-1-cyclohexyl-3-(1H-imidazol-4-yl)propan-1-one hydrochloride | 16% |

1H NMR: 1.26-1.71 (m, 5H), 1.60-1.75 (m, 5H), 2.31-2.4 (m, 1H), 3.03 (dd, 1H, J = 17.3, 5.1 Hz), 3.37 (dd, 1H, J = 17.3, 9.2 Hz), 5.03 (dd, 1H, J = 9.1, 5.1 Hz), 6.67 (s, 1H), 7.03 (m, 1H), 7.14-7.37 (m, 2H), 7.46-7.52 (m, 2H)

| # | Compound | Name |
|---|---|---|
| 15 | | 3-(2-bromophenyl)-3-(1H-imidazol-4-yl)-1-(1-(2-phenylacetyl)piperidin-4-yl)propan-1-one |

| # | Compound | Name |
|---|---|---|
| 16 | | 3-(2-bromophenyl)-3-(1H-imidazol-4-yl)-1-(1-(2-(tetrahydro-2H-pyran-4-yl)acetyl)piperidin-4-yl)propan-1-one |
| 17 | | 3-(2-bromophenyl)-3-(1H-imidazol-4-yl)-1-(1-(2-(4-(trifluoromethyl)phenyl)acetyl)piperidin-4-yl)propan-1-one |
| 18 | | 3-(2-bromophenyl)-3-(1H-imidazol-4-yl)-1-(4-methylenecyclohexyl)propan-1-one |
| 19 | | 1-(4-((benzyloxy)methyl)cyclohexyl)-3-(2-bromophenyl)-3-(1H-imidazol-4-yl)propan-1-one |
| 20 | | 3-(2-bromophenyl)-1-(cyclohex-3-en-1-yl)-3-(1H-imidazol-4-yl)propan-1-one |

| # | Compound | Name |
|---|----------|------|
| 21 | | 3-(2-bromophenyl)-1-cyclopentyl-3-(1H-imidazol-4-yl)propan-1-one |
| 22 | | 3-(2-bromophenyl)-3-(1H-imidazol-4-yl)-1-(pyridin-4-yl)propan-1-one |
| 23 | | 3-(2-bromophenyl)-3-(1H-imidazol-4-yl)-1-(1,4-dioxaspiro[4.5]decan-8-yl)propan-1-one |
| 24 | | 3-(2-bromophenyl)-3-(1H-imidazol-4-yl)-1-(thiazol-5-yl)propan-1-one |
| 25 | | 3-(2-bromophenyl)-1-(2,4-dimethylfuran-3-yl)-3-(1H-imidazol-4-yl)propan-1-one |
| 26 | | 3-(2-bromophenyl)-1-(3-chlorophenyl)-3-(1H-imidazol-4-yl)propan-1-one |

Example 3 General Procedure for the Synthesis of 1-(9H-Imidazo[1,5-a]indol-9-yl) ethanones

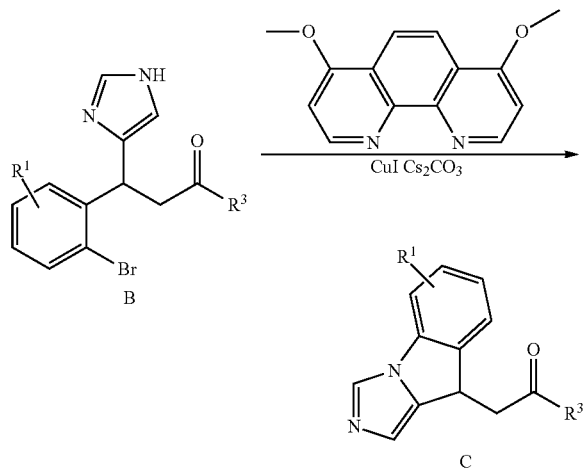

A mixture of intermediate B (1.29 mmol), Cs₂CO₃ (2.59 mmol), 4,7-dimethoxy-1,10-phenanthroline (0.26 mmol) and CuI (0.129 mmol) in a glass vial fitted with a septum is evacuated and backfilled with argon. The mixture is diluted with dry 1,4-dioxane (10 mL) and the resulting mixture is again evacuated and backfilled with argon. The mixture is stirred overnight at 100° C. After cooling to rt, the solvent is removed under reduced pressure and the crude is diluted with 1% NH₄OH (30 mL) solution and dichloromethane (25 mL). The organic layer is separated and the aqueous layer is extracted with CH₂Cl₂ (3×30 mL). The combined organic extracts are washed with brine (30 mL), dried over Na₂SO₄ and concentrated to afford crude. The crude is purified by column chromatography to afford the following compounds.

| # | Compound | Name | Yield |
|---|----------|------|-------|
| 27 | | 1-cyclohexyl-2-(9H-imidazo[1,5-a]indol-9-yl)ethan-1-one | 81% |

$^1$H NMR :_ 1.16-1.48 (m, 5H), 1.66-1.82 (m, 5H), 2.32-2.39 (m, 1H), 2.83 (dd, 1H, J = 18.0, 8.9 Hz), 3.05 (dd, 1H, J = 18.0, 5.7 Hz), 4.55 (dd, 1H, J = 8.9, 5.8 Hz), 6.89 (s, 1H),
7.20 (t, 1H, J = 7.5 Hz), 7.31-7.46 (m, 3H), 7.91 (s, 1H)

| # | Compound | Name |
|---|----------|------|
| 28 | | 1-(4-(2-(9H-imidazo[1,5-a]indol-9-yl)acetyl)piperidin-1-yl)-2-phenylethan-1-one |
| 29 | | 1-(4-(2-(9H-imidazo[1,5-a]indol-9-yl)acetyl)piperidin-1-yl)-2-(tetrahydro-2H-pyran-4-yl)ethan-1-one |

-continued

| # | Compound | Name |
|---|---|---|
| 30 | | 1-(4-(2-(9H-imidazo[1,5-a]indol-9-yl)acetyl)piperidin-1-yl)-2-(4-(trifluoromethyl)phenyl)ethan-1-one |
| 31 | | 2-(9H-imidazo[1,5-a]indol-9-yl)-1-(4-methylenecyclohexyl)ethan-1-one |
| 32 | | 1-(4-((benzyloxy)methyl)cyclohexyl)-2-(9H-imidazo[1,5-a]indol-9-yl)ethan-1-one |
| 33 | | 1-(cyclohex-3-en-1-yl)-2-(9H-imidazo[1,5-a]indol-9-yl)ethan-1-one |
| 34 | | 1-cyclopentyl-2-(9H-imidazo[1,5-a]indol-9-yl)ethan-1-one |
| 35 | | 2-(9H-imidazo[1,5-a]indol-9-yl)-1-(pyridin-4-yl)ethan-1-one |
| 36 | | 2-(9H-imidazo[1,5-a]indol-9-yl)-1-(1,4-dioxaspiro[4.5]decan-8-yl)ethan-1-one |

| # | Compound | Name |
|---|---|---|
| 37 | | 2-(9H-imidazo[1,5-a]indol-9-yl)-1-(thiazol-5-yl)ethan-1-one |
| 38 | | 1-(2,4-dimethylfuran-3-yl)-2-(9H-imidazo[1,5-a]indol-9-yl)ethan-1-one |
| 39 | | 1-(3-chlorophenyl)-2-(9H-imidazo[1,5-a]indol-9-yl)ethan-1-one |

Example 4 Synthesis of 3-bromo-1trytil-1H-1,2,4-triazole

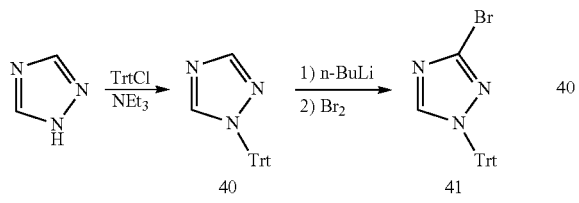

Triethylamine (5.49 g, 54.30 mmol) is added to a solution of 1,2,4-triazole (3.0 g, 43.44 mmol) in DMF (50 mL) at rt. After stirring for 5 minutes, trityl chloride (12.11 g, 43.44 mmol) is added as a solid and the mixture is stirred overnight. The solvent is distilled off under reduced pressure and the crude is partitioned between dichloromethane (50 mL) and water (50 mL). The organic layer is separated and the aqueous layer is extracted with dichloromethane (3×50 mL). The combined organic layers are washed with water (3×40 mL). The organic layer is dried over Na₂SO₄ and concentrated under reduced pressure to afford the product 1-trytil-1H-1,2,4-triazole (12.6 g, 93%). n-BuLi (4.5 mL, 11.24 mmol; 2.5 M solution in hexanes) is added to a solution of 1-trityl-1H-1,2,4-triazole (3.5 g, 11.24 mmol) in THF (120 mL) at −78° C. and the solution is stirred for 45 min. Bromine (1.76 g, 11.02 mmol) is added dropwise over a period of 5 minutes and the solution is stirred for 2 h allowed to warm to −20° C. and quenched by adding saturated NH₄Cl solution (30 mL). The reaction mixture is diluted with water (60 mL) and dichloromethane (40 mL). The organic layer is separated and the aqueous layer is extracted with CH₂Cl₂ (4×50 mL). The combined organic extract was dried over Na₂SO₄ and the solvent evaporated under reduced pressure to afford crude which is used as such for the next step (4.2 g, 95%). 7.09-7.16 (m, 6H), 7.27-7.40 (m, 9H), 7.86 (s, 1H).

Example 5 Synthesis of 2-(1-trytil-1H-1,2,4-triazol-3yl)benzaldehyde

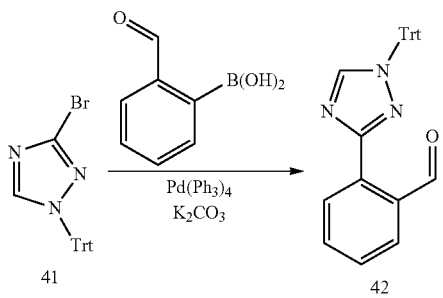

A mixture of 3-bromo-1-trityl-1H-1,2,4-triazole (1.50 g, 3.84 mmol), the appropriate (2-formylphenyl)boronic acid (4.61 mmol), Pd(PPh₃)₄ (222 mg, 0.19 mmol) and K₃CO₃ (1.17 g, 8.46 mmol) in 1,4-dioxane/water (50 mL: 7.5 mL) is evacuated with vacuum and backfilled with argon three times followed by purging with argon for 5 minutes. The reaction mixture is heated at 95° C. for 18 h under an atmosphere of argon. After cooling to rt, the suspension is concentrated under reduced pressure. The crude is partitioned between water (40 mL) and dichloromethane (40 mL). The organic layer is separated and the aqueous layer is extracted with dichloromethane (3×40 mL). The combined organic layers are washed with water (2×30 mL), brine and dried over Na$_2$SO$_4$. The solvent is distilled off under reduced pressure and the crude is purified by flash column chromatography to afford the desired compound (62% yield). $^1$H NMR: 7.09-7.11 (m, 6H), 7.25-7.29 (m, 9H), 7.43 (t, H, J=7.6 Hz), 7.56 (t, 1H, J=7.6 Hz), 7.90 (d, 1H, J=7.8 Hz), 8.02 (s, 1H), 8.02 (d, J=8.6 Hz), 10.44 (s, 1H).

Example 6 General Procedure for the Synthesis of 2-(5H-[1,2,4]Triazolo[3,4-a]isoindol-5-yl)ethanones by Horner-Wadsworth-Emmons Reaction Followed by Cyclization

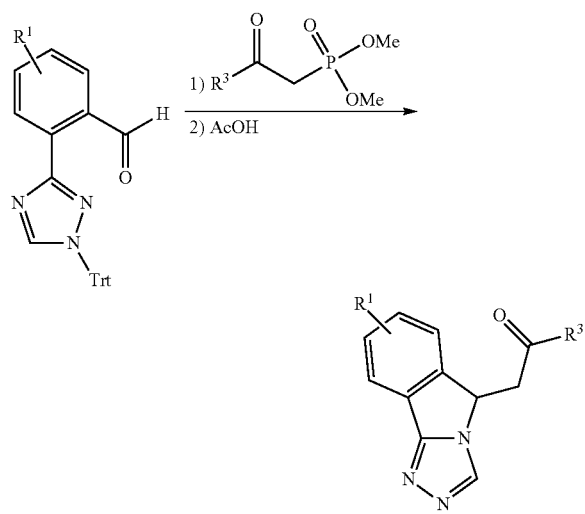

The appropriate phosphonate reagent (1.44 mmol) as a solution in THF (2 mL) is added to a suspension of NaH (34.6 mg, 1.44 mmol) in THF (10 mL) at 0° C. and the mixture is stirred for 45 min. The appropriate benzaldehyde derivative (1.44 mmol) is added as a solution in THF (3 mL) dropwise via a syringe over a period of 3-4 minutes. The reaction is allowed to warm to RT and stirred overnight. The solvent is removed under reduced pressure and the crude is diluted with saturated NH$_4$Cl (10 mL) and water (10 mL). The aqueous layer is extracted with CH$_2$Cl$_2$ (2×20 mL) and the combined organic fractions are washed with brine (15 mL), dried over Na$_2$SO$_4$ and concentrated under reduced pressure to afford the crude product. AcOH (1 mL) and MeOH (3 mL) is added and the solution is stirred at 90° C. overnight. After cooling to rt, the solvent is distilled off and the crude is stirred in a mixture of saturated K$_2$CO$_3$ (5 mL) and CH$_2$Cl$_2$ (5 mL). The organic layer is separated and the aqueous layer is extracted with CH$_2$Cl$_2$ (2×25 mL). The combined organic layers are washed with water, brine and dried (Na$_2$SO$_4$) and the solvent evaporated under reduced pressure. The crude residue is purified by flash column chromatography on silica gel to afford the following compounds.

| # | Compound | Name | Yield |
|---|---|---|---|
| 43 | | 2-(5H-[1,2,4]triazolo[3,4-a]isoindol-5-yl)-1-cyclohexylethan-1-one | 12% |

$^1$H NMR: 1.18-1.48 (m, 6H), 1.68-2.04 (m, 6H), 2.38-2.41 (m, 1H), 2.82 (dd, 1H, J = 18.8, 10.4 Hz), 3.30 (dd, 1H, J = 18.6, 2.6 Hz), 5.57 (dd, 1H, J = 12.8, 2.4 Hz), 7.40-7.54 (m, 3H), 8.0 (d, 1H, J = 7.6 Hz), 8.30 (s, 1H)

| # | Compound | Name |
|---|---|---|
| 44 | | 1-(4-(2-(5H-[1,2,4]triazolo[3,4-a]isoindol-5-yl)acetyl)piperidin-1-yl)-2-phenylethan-1-one |
| 45 | | 1-(4-(2-(5H-[1,2,4]triazolo[3,4-a]isoindol-5-yl)acetyl)piperidin-1-yl)-2-(tetrahydro-2H-pyran-4-yl)ethan-1-one |
| 46 | | 2-(5H-[1,2,4]triazolo[3,4-a]isoindol-5-yl)-1-(4-methylenecyclohexyl)ethan-1-one |

| # | Compound | Name |
|---|---|---|
| 47 | | 2-(5H-[1,2,4]triazolo[3,4-a]isoindol-5-yl)-1-(4-((benzyloxy)methyl)cyclohexyl)ethan-1-one |
| 48 | | 2-(5H-[1,2,4]triazolo[3,4-a]isoindol-5-yl)-1-(cyclohex-3-en-1-yl)ethan-1-one |
| 49 | | 2-(5H-[1,2,4]triazolo[3,4-a]isoindol-5-yl)-1-cyclopentylethan-1-one |
| 50 | | 2-(5H-[1,2,4]triazolo[3,4-a]isoindol-5-yl)-1-(pyridin-4-yl)ethan-1-one |
| 51 | | 2-(5H-[1,2,4]triazolo[3,4-a]isoindol-5-yl)-1-(3-chlorophenyl)ethan-1-one |

Example 7 Synthesis of 2-(1-(2,4-dimethoxybenzyl)-1H-1,2,3-triazol-4-yl)benzaldehyde

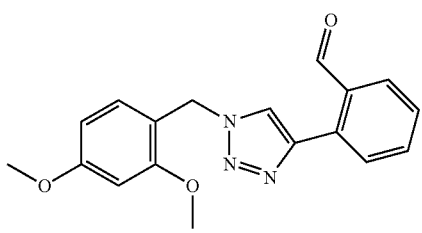

52

1-(Azidomethyl)-2,4-dimethoxybenzene (3.0 g, 15.53 mmol) and 2-ethynylbenzaldehyde (2.43 g, 18.63 mmol) are dissolved in DMSO (15 mL) and added to t-butyl alcohol (80 mL) in a 250 mL flask. Sodium ascorbate (3.08 g, 15.53 mmol) dissolved in 20 mL water is added, followed by copper (II) sulfate pentahydrate (373 mg, 1.55 mmol) dissolved in 5 mL water. The resulting mixture is stirred at room temperature for 24 h. The reaction is then quenched by adding saturated NH$_4$Cl (20 mL). The aqueous solution is extracted with EtOAc (3×50 mL). The combined organic layers are washed with brine, and dried with anhydrous MgSO$_4$. The solvent is removed under reduced pressure and the crude residue was purified by column chromatography. $^1$H NMR: 3.81 (s, 3H), 3.95 (s, 3H), 5.54 (s, 2H), 6.48-6.51 (m, 2H), 7.25-7.27 (m, 1H), 7.47 (td, J=7.4, 1.3 Hz, 1H), 7.60-7.64 (m, 2H), 7.77 (s, 1H), 7.99 (dd, 1H, J=7.8, 1.3 Hz), 10.36 (s, 1H).

Example 8 General Procedure for the Synthesis of 2-(8H-[1,2,3]Triazolo[5,1-a]isoindol-8-yl)ethanones by Horner-Wadsworth-Emmons Reaction Followed by Cyclization

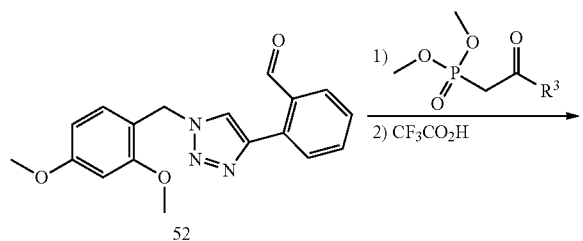

A solution of the appropriate phosphonate reagent (0.93 mmol) in THF (6 mL) is added dropwise to a suspension of NaH (23.4 mg, 0.93 mmol) in THF (3 mL) at 0° C. and the mixture is stirred for 45 min. The appropriate substituted benzaldehyde (0.927 mmol) is added as a solution in THF (6 mL) dropwise. The reaction is allowed to warm to rt and stirred overnight. The solvent was distilled off and the crude is diluted with saturated $NH_4Cl$ (10 mL) and water (10 mL). The aqueous layer is extracted with $CH_2Cl_2$ (3×40 mL), the combined organic fractions are dried over $Na_2SO_4$ and concentrated under reduced pressure to afford the crude product. The crude is stirred in trifluoroacetic acid (10 mL) at 65° C. for 6 h. The reaction mixture is concentrated and the crude is taken in $CH_2Cl_2$ (35 mL) and diluted with saturated $Na_2CO_3$ (20 mL), the organic layer is separated and the aqueous layer is extracted with $CH_2Cl_2$ (2×30 mL). The combined organic extract is dried over $Na_2SO_4$ and concentrated under reduced pressure to afford the crude. The crude residue is purified by flash column chromatography on silica gel to afford the following compounds.

| # | Compound | Name | Yield |
|---|----------|------|-------|
| 53 | | 2-(8H-[1,2,3]triazolo[5,1-a]isoindol-8-yl)-1-cyclohexylethan-1-one | 95% |

$^1$H NMR: 1.06-1.45 (m, 5H), 1.56-1.65 (m, 1H), 1.67-1.91 (m, 4H), 2.34 (tt, J = 11.4, 3.5 Hz, 1H), 2.93 (dd, J = 18.0, 8.7 Hz, 1H), 3.52 (dd, J = 18.0, 4.3 Hz, 1H), 5.89 (ddt, J = 8.7, 4.4, 0.8 Hz, 1H), 7.25-7.34 (m, 1H), 7.38 (tdd, J = 7.5, 1.2, 0.6 Hz, 2H), 7.56 (dt, J = 7.0, 1.1 Hz, 1H), 7.75 (s, 1H)

| # | Compound | Name | Yield |
|---|----------|------|-------|
| 54 | | 2-(8H-[1,2,3]triazolo[5,1-a]isoindol-8-yl)-1-(4,4-difluorocyclohexyl)ethan-1-one | 95% |

$^1$H NMR: 1.65-1.88 (m, 4H), 1.89-2.02 (m, 2H), 2.06-2.25 (m, 2H), 2.43-2.55 (m, 1H), 3.05 (dd, J = 17.9, 8.0 Hz, 1H), 3.55 (dd, J = 17.9, 4.9 Hz, 1H), 5.94 (dd, J = 8.0, 5.0 Hz, 1H), 7.33-7.41 (m, 1H), 7.41-7.50 (m, 2H), 7.63 (d, J = 7.5 Hz, 1H), 7.81 (s, 1H).

| # | Compound | Name |
|---|----------|------|
| 55 | | 1-(4-(2-(8H-[1,2,3]triazolo[5,1-a]isoindol-8-yl)acetyl)piperidin-1-yl)-2-phenylethan-1-one |

-continued

| # | Compound | Name |
|---|----------|------|
| 56 | 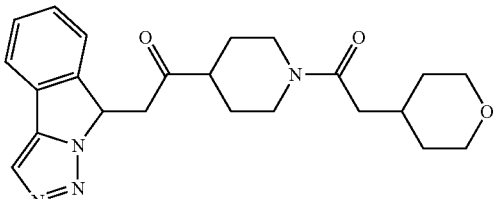 | 1-(4-(2-(8H-[1,2,3]triazolo[5,1-a]isoindol-8-yl)acetyl)piperidin-1-yl)-2-(tetrahydro-2H-pyran-4-yl)ethan-1-one |
| 57 | 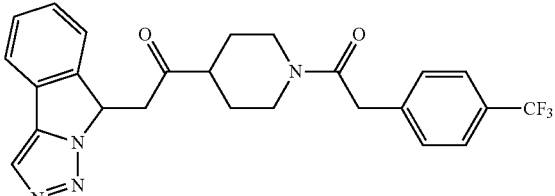 | 1-(4-(2-(8H-[1,2,3]triazolo[5,1-a]isoindol-8-yl)acetyl)piperidin-1-yl)-2-(4-(trifluoromethyl)phenyl)ethan-1-one |
| 58 | 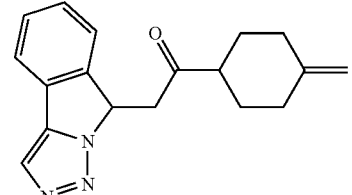 | 2-(8H-[1,2,3]triazolo[5,1-a]isoindol-8-yl)-1-(4-methylenecyclohexyl)ethan-1-one |
| 59 | 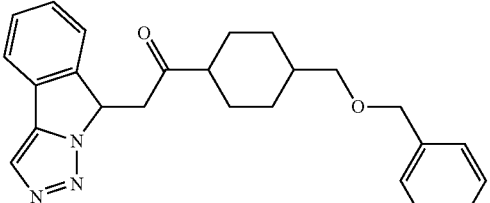 | 2-(8H-[1,2,3]triazolo[5,1-a]isoindol-8-yl)-1-(4-((benzyloxy)methyl)cyclohexyl)ethan-1-one |
| 60 | 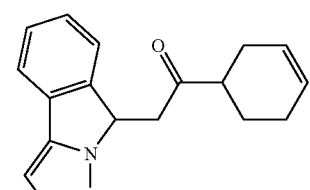 | 2-(8H-[1,2,3]triazolo[5,1-a]isoindol-8-yl)-1-(cyclohex-3-en-1-yl)ethan-1-one |
| 61 | 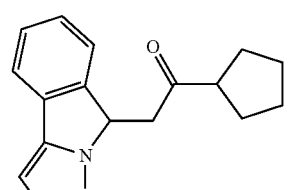 | 2-(8H-[1,2,3]triazolo[5,1-a]isoindol-8-yl)-1-cyclopentylethan-1-one |
| 62 | 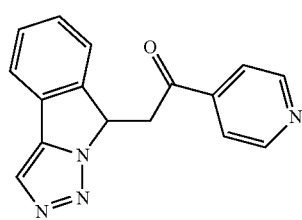 [SMILES: O=C(CC1c2ccccc2-c2cnnn21)c1ccncc1] | 2-(8H-[1,2,3]triazolo[5,1-a]isoindol-8-yl)-1-(pyridin-4-yl)ethan-1-one |

| # | Compound | Name |
|---|---|---|
| 63 | | 2-(8H-[1,2,3]triazolo[5,1-a]isoindol-8-yl)-1-(3-chlorophenyl)ethan-1-one |
| 64 | | 1-(4-(2-(8H-[1,2,3]triazolo[5,1-a]isoindol-8-yl)acetyl)piperidin-1-yl)-2-phenylethan-1-one |

Example 9 Synthesis of 4-(2-(8H-[1,2,3]triazolo[5,1-a]isoindol-8-yl)acetyl)-N-(p-tolyl)piperidine-1-carboxamide

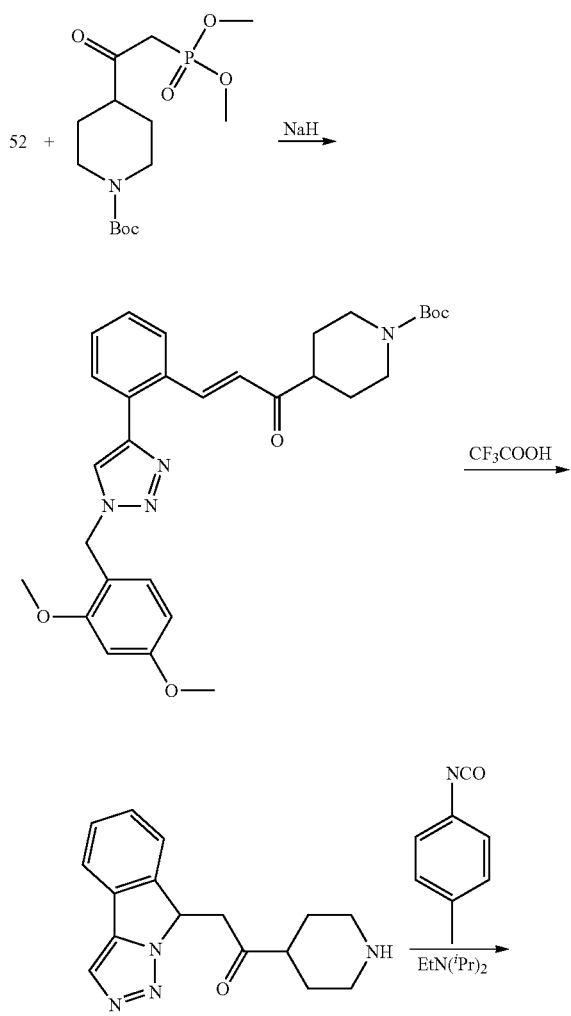

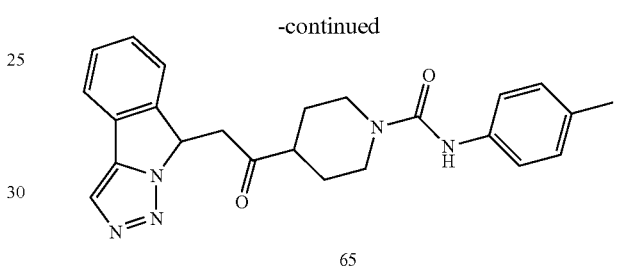

65

A solution of tert-butyl 4-(2-(dimethoxyphosphoryl)acetyl)piperidine-1-carboxylate (1.37 g, 4.08 mmol) in THF (12 mL) is added dropwise to a suspension of NaH (93.8 mg, 3.71 mmol) in THF (20 mL) at 0° C. and the mixture is stirred for 40 min. 2-(1-(2,4-dimethoxybenzyl)-1H-1,2,3-triazol-4-yl)benzaldehyde (1.20 g, 3.71 mmol) is added as a solution in THF (12 mL) dropwise over a period of 15 min. The reaction is allowed to warm to RT and stirred overnight. The solvent is distilled off under reduced pressure and the crude is diluted with saturated $NH_4Cl$ (20 mL) and water (10 mL). The aqueous layer is extracted with EtOAc (3×50 mL) and the combined organic fractions are dried over $Na_2SO_4$, filtered and concentrated under reduced pressure to afford the crude product. The crude product is stirred in trifluoroacetic acid (15 mL) at 65° C. for 6 h. The reaction mixture is concentrated and the residue is dissolved in dichloromethane (20 mL) and poured into a separatory funnel containing saturated $NaHCO_3$ (10 mL). The aqueous layer is extracted with 5% $CF_3CF_2OH/CH_2Cl_2$ (2×20 mL). The combined organic layers are dried and concentrated. The crude is purified by flash column chromatography to afford the desired piperidine analog which contained some impurities. The impure piperidine is used in the next step without further purification. To a vial containing crude 2-(8H-[1,2,3]triazolo[5,1-a]isoindol-8-yl)-1-(piperidin-4-yl)ethanone (100 mg, 0.35 mmol) in dichloromethane (4 mL), DIPEA (0.25 mL, 1.42 mmol) and 4-methylphenylisocyanate (50 µL, 0.35 mmol) are added. The reaction mixture is stirred at rt for 30 min and concentrated. The crude product is dissolved in EtOAc (30 mL) and washed with water (3×10 mL) and brine. The organic layer is dried over $Na_2SO_4$ and concentrated. The crude is purified by flash column chromatography to afford the desired product (65) as yellow solid (113 mg, 77%). ¹H NMR: 1.61-1.75 (m, 2H), 1.82-1.96 (m, 2H), 2.27 (s, 3H), 2.57-2.61 (m, 1H), 2.87-2.98 (m, 2H), 3.06 (dd, 1H, J=7.6, 18.0 Hz), 3.51 (dd, 1H, J=5.2, 18.0 Hz), 4.04-4.09 (m, 2H), 5.93-5.96 (m, 1H), 6.63 (s, 1H), 7.06 (d, 2H, J=6.4 Hz), 7.22 (d, 1H, J=6.0 Hz), 7.35-7.40 (m, 2H), 7.43-7.47 (m, 2H), 7.64 (d, 1H, J=7.6 Hz), 7.82 (s, 1H).

Example 10 General Procedure for the Reduction of Ketones

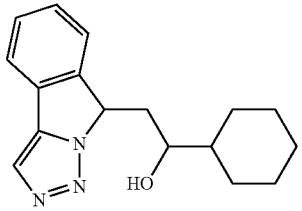 [SMILES: OC(CC1c2ccccc2-c2cnnn21)C1CCCCC1]

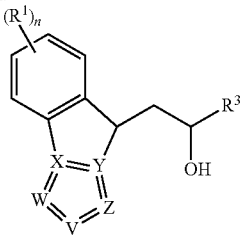

NaBH₄ (0.75 mmol) is added to a solution of the appropriate ketone (53-65) (0.25 mmol) in MeOH (2 mL) at 0° C., and the solution is stirred for 1 h. The solvent is removed under reduced pressure and 2M HCl (2 mL) is added to the crude. The solution is allowed to stir for 10 min and made basic by saturated K₂CO₃ solution. The aqueous layer is extracted with CH₂Cl₂ (3×5 mL). The combined organic layers are washed with brine, dried (MgSO4) and concentrated under reduced pressure to afford the crude residue. The crude is purified by column chromatography to afford the following compounds.

| # | Compound | Name | Yield |
|---|----------|------|-------|
| 66 | | 2-(8H-[1,2,3]triazolo[5,1-a]isoindol-8-yl)-1-cyclohexylethan-1-ol | 67% |

¹H NMR: Mixture of isomers: 0.96-1.31 (m, 5H) 1.39-1.44 (m, 1H), 1.58-1.98 (m, 5H), 2.20-2.39 (m, 1H), 2.48 (br s, 1H), 3.82-3.84 and 4.22-4.27 (m, 1H), 5.60 and 5.75 (t and dd, 1H, J = 6.7 Hz and J = 11.0, 3.3 Hz), 7.35-7.55 (m, 3H), 7.64 (d, 1H, J = 7.0 Hz), 7.81 and 7.82 (two s, 1H)

| 67 | | 4-(2-(8H-[1,2,3]triazolo[5,1-a]isoindol-8-yl)-1-hydroxyethyl)-N-(p-tolyl)piperidine-1-carboxamide | 70% |

¹H NMR: Mixture of isomers: 1.32-1.40 (m, 2H), 1.58-1.77 (m, 3H), 1.85 and 1.94 (two d, J = 13.0 Hz, 1H), 2.04 (br s, 1H), 2.23 (s, 3H), 2.31-2.38 (m, 1H), 2.70-2.87 (m, 2H), 4.10-4.14 (m, 2H), 4.31-4.35 (m, 1H), 5.59 (t, J = 6.6 Hz, 0.5H), 5.72 (dd, J = 11.4, 3.5 Hz, 0.5H), 6.71 and 6.79 (two s, 1H), 6.95-7.05 (m, 2H), 7.20 (dd, J = 8.4, 1.6 Hz, 2H), 7.34-7.49 (m, 3H), 7.52 and 7.63 (two d, J = 7.4 Hz, 1H), 7.81 (s, 1H).

| 68 | | 2-(8H-[1,2,3]triazolo[5,1-a]isoindol-8-yl)-1-(4,4-difluorocyclohexyl)ethan-1-ol | 91% |

¹H NMR: Mixture of isomers: 1.33-1.58 (m, 3H) 1.59-1.83 (m, 3H), 1.90-2.03 (m, 1H), 2.06-2.15 (m, 2H), 2.23-2.53 (m, 1H), 3.58-3.70 (m, 1H), 3.95-4.01 and 4.36-4.43 (two m, 1H), 5.63 and 5.77 (t and dd, 1H, J = 6.7 Hz and J = 11.1, 3.2 Hz), 7.36-7.53 (m, 3H), 7.56 and 7.65 (two d, 1H, J = 7.6 Hz), 7.83 and 7.84 (two s, 1H).

-continued

| # | Compound | Name | Yield |
|---|---|---|---|
| 69 | 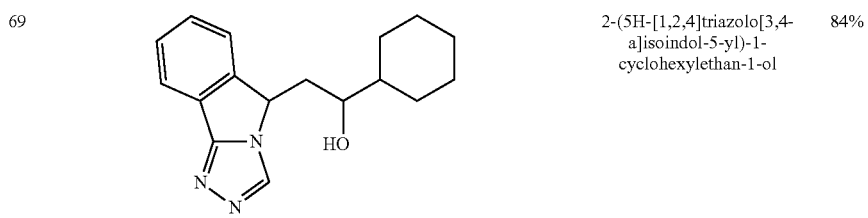 | 2-(5H-[1,2,4]triazolo[3,4-a]isoindol-5-yl)-1-cyclohexylethan-1-ol | 84% |

$^1$H NMR: Mixture of isomers: 0.95-1.31 (m, 5H) 1.39-1.44 (m, 1H), 1.66-1.77 (m, 5H), 2.05-2.13 and 2.33-2.38 (two m, 2H), 3.70-3.71 and 3.84-3.89 (two m, 1H), 5.32 and 5.54 (t and d, 1H, J = 6.4 Hz and J = 10.8, 3.2 Hz), 7.44-7.53 (m, 3H), 7.95-7.99 (m, 1H), 8.57 and 8.60 (two s, 1H)

| # | Compound | Name | Yield |
|---|---|---|---|
| 70 | 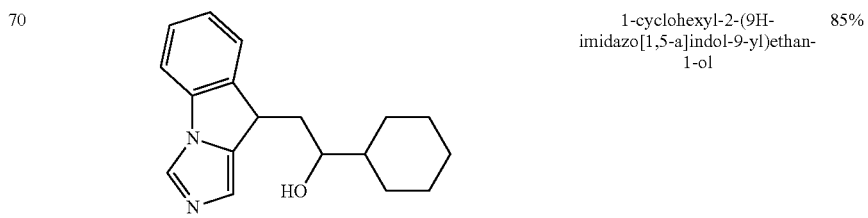 | 1-cyclohexyl-2-(9H-imidazo[1,5-a]indol-9-yl)ethan-1-ol | 85% |

$^1$H NMR: Mixture of isomers: 1.0-1.26 (m, 5H), 1.37-1.38 (m, 1H), 1.67-1.86 (m, 4H), 1.95-2.15 (m, 3H), 3.72-3.75 (m, 1H), 4.26 and 4.39 (t and dd, 1H, J = 6.2 Hz and, J = 11.5, 3.9 Hz), 7.0 (d, 1H, J = 6.2 Hz), 7.22 (td, 1H, J = 7.6, 3.5 Hz), 7.35 (td, 1H, J = 7.5, 2.9 Hz), 7.40 and 7.42 (two s, 1H), 7.43 and 7.50 (two d, 1H, J = 7.6 Hz), 7.93 and 7.94 (two s, 1H)

| # | Compound | Name |
|---|---|---|
| 71 | 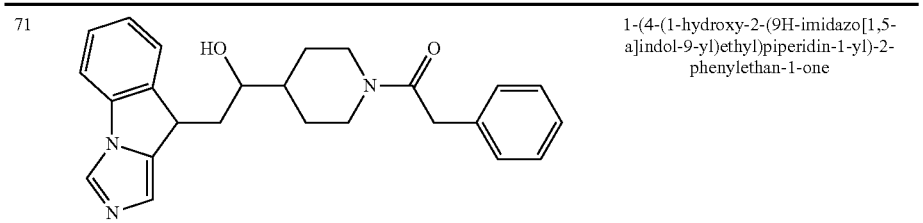 | 1-(4-(1-hydroxy-2-(9H-imidazo[1,5-a]indol-9-yl)ethyl)piperidin-1-yl)-2-phenylethan-1-one |
| 72 | 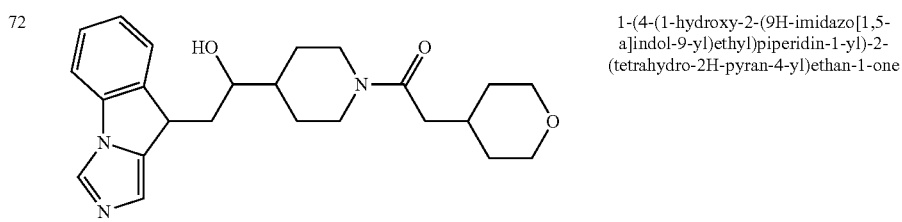 | 1-(4-(1-hydroxy-2-(9H-imidazo[1,5-a]indol-9-yl)ethyl)piperidin-1-yl)-2-(tetrahydro-2H-pyran-4-yl)ethan-1-one |
| 73 | 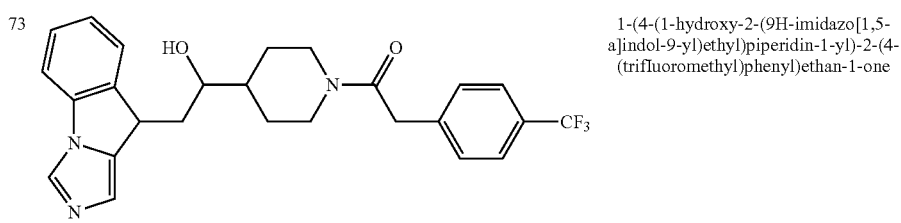 | 1-(4-(1-hydroxy-2-(9H-imidazo[1,5-a]indol-9-yl)ethyl)piperidin-1-yl)-2-(4-(trifluoromethyl)phenyl)ethan-1-one |

| # | Compound | Name |
|---|---|---|
| 74 | | 2-(9H-imidazo[1,5-a]indol-9-yl)-1-(4-methylenecyclohexyl)ethan-1-ol |
| 75 | | 1-(4-((benzyloxy)methyl)cyclohexyl)-2-(9H-imidazo[1,5-a]indol-9-yl)ethan-1-ol |
| 76 | | 1-(cyclohex-3-en-1-yl)-2-(9H-imidazo[1,5-a]indol-9-yl)ethan-1-ol |
| 77 | | 1-cyclopentyl-2-(9H-imidazo[1,5-a]indol-9-yl)ethan-1-ol |
| 78 | | 2-(9H-imidazo[1,5-a]indol-9-yl)-1-(pyridin-4-yl)ethan-1-ol |
| 79 | | 2-(9H-imidazo[1,5-a]indol-9-yl)-1-(1,4-dioxaspiro[4.5]decan-8-yl)ethan-1-ol |
| 80 | | 2-(9H-imidazo[1,5-a]indol-9-yl)-1-(thiazol-5-yl)ethan-1-ol |

| # | Compound | Name |
|---|----------|------|
| 81 | | 1-(2,4-dimethylfuran-3-yl)-2-(9H-imidazo[1,5-a]indol-9-yl)ethan-1-ol |
| 82 | | 1-(3-chlorophenyl)-2-(9H-imidazo[1,5-a]indol-9-yl)ethan-1-ol |
| 83 | | 1-(4-(2-(8H-[1,2,3]triazolo[5,1-a]isoindol-8-yl)-1-hydroxyethyl)piperidin-1-yl)-2-phenylethan-1-one |
| 84 | | 1-(4-(2-(8H-[1,2,3]triazolo[5,1-a]isoindol-8-yl)-1-hydroxyethyl)piperidin-1-yl)-2-(tetrahydro-2H-pyran-4-yl)ethan-1-one |
| 85 | | 1-(4-(2-(8H-[1,2,3]triazolo[5,1-a]isoindol-8-yl)-1-hydroxyethyl)piperidin-1-yl)-2-(4-(trifluoromethyl)phenyl)ethan-1-one |
| 86 | | 2-(8H-[1,2,3]triazolo[5,1-a]isoindol-8-yl)-1-(4-methylenecyclohexyl)ethan-1-ol |
| 87 | | 2-(8H-[1,2,3]triazolo[5,1-a]isoindol-8-yl)-1-(4-((benzyloxy)methyl)cyclohexyl)ethan-1-ol |

| # | Compound | Name |
|---|---|---|
| 88 | | 2-(8H-[1,2,3]triazolo[5,1-a]isoindol-8-yl)-1-(cyclohex-3-en-1-yl)ethan-1-ol |
| 89 | | 2-(8H-[1,2,3]triazolo[5,1-a]isoindol-8-yl)-1-cyclopentylethan-1-ol |
| 90 | | 2-(8H-[1,2,3]triazolo[5,1-a]isoindol-8-yl)-1-(pyridin-4-yl)ethan-1-ol |
| 91 | | 2-(8H-[1,2,3]triazolo[5,1-a]isoindol-8-yl)-1-(3-chlorophenyl)ethan-1-ol |
| 92 | | 1-(4-(2-(8H-[1,2,3]triazolo[5,1-a]isoindol-8-yl)-1-hydroxyethyl)piperidin-1-yl)-2-phenylethan-1-one |
| 93 | | 1-(4-(2-(5H-[1,2,4]triazolo[3,4-a]isoindol-5-yl)-1-hydroxyethyl)piperidin-1-yl)-2-phenylethan-1-one |
| 94 | | 1-(4-(2-(5H-[1,2,4]triazolo[3,4-a]isoindol-5-yl)-1-hydroxyethyl)piperidin-1-yl)-2-(tetrahydro-2H-pyran-4-yl)ethan-1-one |

-continued

| # | Compound | Name |
|---|---|---|
| 95 | | 2-(5H-[1,2,4]triazolo[3,4-a]isoindol-5-yl)-1-(4-methylenecyclohexyl)ethan-1-ol |
| 96 | | 2-(5H-[1,2,4]triazolo[3,4-a]isoindol-5-yl)-1-(4-((benzyloxy)methyl)cyclohexyl)ethan-1-ol |
| 97 | | 2-(5H-[1,2,4]triazolo[3,4-a]isoindol-5-yl)-1-(cyclohex-3-en-1-yl)ethan-1-ol |
| 98 | | 2-(5H-[1,2,4]triazolo[3,4-a]isoindol-5-yl)-1-cyclopentylethan-1-ol |
| 99 | | 2-(5H-[1,2,4]triazolo[3,4-a]isoindol-5-yl)-1-(pyridin-4-yl)ethan-1-ol |
| 100 | | 2-(5H-[1,2,4]triazolo[3,4-a]isoindol-5-yl)-1-(3-chlorophenyl)ethan-1-ol |

Example 11 Synthesis of 1,4-dihydroindeno[1,2-c]pyrazole

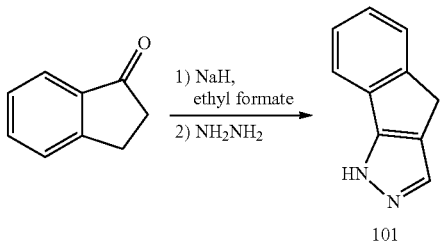 [SMILES: O=C1CCc2ccccc21 ; c1ccc2c(c1)Cc1cn[nH]c1-2]

101

A mixture of indanone (500 mg, 3.78 mmol), ethyl formate (0.61 mL, 7.57 mmol), 95% NaH (290 mg, 11.4 mmol) and benzene (12 mL) is stirred at room temperature overnight. The solvent is removed. Ethanol (20 mL), acetic acid (2.4 mL) and hydrazine monohydrate (2.4 mL) is added slowly to the residue. The mixture is heated to reflux for 3 hours and the solvents were removed. The residue is suspended in water (12 mL), and the solid is collected by filtration, washed with water (12 mL) and $NaHCO_3$ (12 mL), and dried to give the desired product as brown powder (505 mg, 86%). $^1$H NMR 3.63 (s, 2H), 7.29 (d, 1H, J=7.6 Hz), 7.36 (t, 1H, J=7.4 Hz), 7.47 (s, 1H), 7.50 (d, 1H, J=7.2 Hz), 7.77 (d, 1H, J=7.6 Hz).

Example 12 Human IDO Protein Cloning, Expression and Purification

Expression vectors for human indoleamine-2,3-dioxygenase (IDO) protein were prepared by amplification of a 1219 bp fragment of the sequence present in vector phIDO6His cDNA with primers 5'-ggagcatgctaATGGCA-CACGCTATGGAAAAC-3' and 5'-gagagatctACCTTCCT-TCAAAAGGGATTTC-3' and cloning the SphI-BglII 1213 bp fragment into pQE70 (Qiagen), to yield vector pQE70-hIDO. This construct adds 2 extra amino acids and a 6-Histidine tag to the C-terminus of the natural human IDO protein while preserving intact the natural start codon and N-terminus amino acid sequence. The amplified allele of human IDO shows two polymorphisms with respect to the sequence deposited in accession file P14902 of SwissProt database. These polymorphisms result in a P110S and E119G amino acid changes.

Plasmid pQE70-hIDO was transformed into M15(pREP4) cells (Qiagen) and clones were selected in LB-agar plates supplemented with carbenicillin 50 μg/mL and kanamycin 30 g/mL. Protein expression was carried out by growing an overnight culture of the M15pREP4/pQE70-hIDO clone in 100 mL LB supplemented with 100 μg/mL carbenicillin, 50 g/mL kanamycin and 50 μg/mL of L-tryptophan (LBCKT medium). 40 mL of this culture were inoculated into 750 mL of LBCKT for 4 hours at 37° C. This culture was diluted 1:10 into LBCKT medium and cultured for another 2 hours at 37° C. until OD600 was higher than 0.8. At this point the cultures were inoculated with Hemin to 7 μM and L-Tryptophan to 75 μg/mL and incubated at 37° C. for 2 h. Induction of protein expression was carried out by supplementing the cultures with IPTG to 1 mM, PMSF to 200 μM, EDTA to 1 mM and L-tryptophan to 50 μg/mL. Incubation was continued for additional 16 h at 25° C. Cells were collected by centrifugation, and the cell pellets were washed with PBS buffer supplemented with 20 μM PMSF and 1 mM EDTA and stored at −80 OC until protein purification.

The equivalent of 16 L of culture were processed in one batch of purification. Cell pellets were thawed, resuspended in 50 mM potassium phosphate buffer pH 7.0, 20 μM PMSF, 1 mM EDTA, 1 mg/mL lysozyme to 10 mL per liter of bacterial culture and incubated 30 minutes on ice. Cells were then lysed by sonication. Cell lysates were centrifuged 20 min at 20000 g and the supernatant was filtered through 0.45 m filters. The filtered supernatant was loaded onto a 60 mL phosphocellulose column equilibrated with 50 mM potassium phosphate buffer pH 6.5 (KPB) at 1-3 mL/min. The column was washed with 3 volumes of 50 mM KPB, 3 volumes of 100 mM KPB and the protein was eluted with 15 volumes of a linear gradient of 100-500 mM KPB. Fractions were collected and IDO activity assay was performed by measuring kynurenine production. This was carried out by mixing 50 μL of each fraction with 100 μL of reaction mix to yield a final concentration of 50 mM KPB buffer, 20 mM ascorbic acid, 200 g/mL catalase, 2 μM methylene blue and 40 μM L-tryptophan. Fractions demonstrating IDO activity were loaded onto a Ni-NTA purification column (15 mL). This affinity purification column was washed with 10 volumes of 250 mM KPB, 150 mM NaCl, 50 mM imidazole pH 8, and eluted with 10 volumes of buffer containing 250 mM KPB, 150 mM NaCl and a 50 to 250 mM imidazole linear gradient. Collected fractions were assayed by IDO enzymatic assay described above and the positive fractions were pooled and concentrated by ultrafiltration and dialyzed against a buffer containing 250 mM KPB, 50% glycerol. This process yields ~8-10 mg of pure protein (>98%) with a specific activity of 170 μmol/h/mg.

Example 13 Testing of IDO Inhibitory Compounds by Enzymatic IDO Assay

The $IC_{50}$ values for each compound were determined by testing the activity of IDO in a mixture containing 50 mM potassium phosphate buffer at pH 6.5; 70 nM purified human IDO protein, 20 μM L-tryptophan, 20 mM ascorbate, 2 μM methylene blue, 0.1% DMSO. The inhibitors were initially diluted in DMSO at 100 mM and were diluted in potassium phosphate 50 mM, added to the reaction mixture at final concentrations raging from 1 mM to 5 nM and preincubated with the enzyme for 5 min at 25° C. The reaction was started by addition of L-tryptophan to 20 μM and incubated 15 min at 37° C. The reaction was stopped by addition of 0.5 vol of 30% trichloroacetic acid and incubated 30 min at 60° C. to hydrolyze N-formylkynurenine to kynurenine. The reaction was centrifuged at 3400 g for 5 min to remove precipitated protein and the supernatant was reacted with 2% (w/v) of p-dimethylaminobenzaldehyde in acetic acid. The reaction was incubated 10 min at 25° C. and read at 480 nm in a spectrophotometer. Control samples with no IDO inhibitor, or with no IDO enzyme or with the reference inhibitors 1-methyl-tryptophan (200 μM) and menadione (1.2 μM) were used as controls to set the parameters for the non-linear regressions necessary for determination of the $IC_{50}$ for each compound. Nonlinear regressions and determination of the $IC_{50}$ values were performed using the GraphPad Prism 4 software. Compounds with an $IC_{50}$ of less than 50 μM were considered as active inhibitors in this assay.

Example 14 Testing of TDO Inhibitory Compounds by Enzymatic TDO Assay

The $IC_{50}$ values for each compound were determined by testing the activity of TDO in a mixture containing 50 mM potassium phosphate buffer at pH 6.5; 200 nM purified human TDO protein, 20 µM L-tryptophan, 20 mM ascorbate 0.1% DMSO. Differently from the IDO activity assay, no methylene blue is added to the assay. The inhibitors were initially diluted in DMSO at 100 mM and were diluted in potassium phosphate 50 mM, added to the reaction mixture at final concentrations raging from 30 µM to 5 nM and preincubated with the enzyme for 5 min at 25° C. The reaction was started by addition of L-tryptophan to 20 µM and incubated 15 min at 37° C. The reaction was stopped by addition of 0.5 vol of 30% trichloroacetic acid and incubated 30 min at 60° C. to hydrolyze N-formylkynurenine to kynurenine. The reaction was centrifuged at 3400 g for 5 min to remove precipitated protein and the supernatant was reacted with 2% (w/v) of p-dimethylaminobenzaldehyde in acetic acid. The reaction was incubated 10 min at 25° C. and read at 480 nm in a spectrophotometer. Control samples with no TDO inhibitor, or with no TDO enzyme were used as controls to set the parameters for the non-linear regressions necessary for determination of the $IC_{50}$ for each compound. Nonlinear regressions and determination of the $IC_{50}$ values were performed using the GraphPad Prism 4 software. Compounds with an $IC_{50}$ of less than 50 µM were considered as active inhibitors in this assay.

Example 15 Determination of IDO and TDO Inhibitory Activity and Toxicity in Cell Based Assay by Measurement of Kynurenine 293-T-REx™ cells (Invitrogen) constitutively express a tet operator binding repressor protein and are maintained in DMEM, 10% FBS, 1× Penicillin+Streptomycin, 2 mM L-glutamine, 5 µg/mL blasticidin at 37° C. with a 5% $CO_2$ in air atmosphere and typically split prior to confluency. Cells were passed by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium, 10% DMSO), stored in 1.8 mL cyropreservation vials (~2-5×106 cells per vial), in liquid nitrogen vapor storage tanks.

IDO1-expressing 293-T-Rex™ cell lines were generated by stable transfection of plasmid pcDNA-tetO-IDO expressing human IDO1 or murine IDO1 under the control of the doxycycline-inducible CMV-tet promoter. Similarly, TDO2-expressing 293-T-Rex™ cell lines were generated by stable transfection of plasmid pcDNA-tetO-TDO2 expressing human TDO2 or murine TDO2 under the control of the doxycycline-inducible CMV-tet promoter. Transfected cells were selected in DBZ medium (DMEM, 10% FBS, 1× Penicillin+Streptomycin, 2 mM L-glutamine, 5 µg/mL blasticidin and 25 µg/mL Zeocin) at 37° C. with a 5% $CO_2$ in air atmosphere. Individual clones were isolated by limiting dilution cloning from these populations. These clones were assayed for IDO or TDO activity and the clones that showed the highest levels of IDO or TDO activity inducible by doxycycline were used for subsequent cell based assays.

To setup a cell based activity assay, IDO-293-T-Rex or TDO-293T-Rex cells were harvested and resuspended in DBZ media at $10^6$ cells/mL, and split into poly-D-lysine coated 96-well plates at 100,000 cells per well. 100 µL of Neutral medium (DBZ medium, 200 µM L-tryptophan) or Induction media (Neutral medium supplemented with 5 µM doxycycline) are added to the cells and incubated 28 h at 37° C. After the induction period, medium is removed and replaced with Induction or Neutral medium containing different concentrations of each inhibitor (30 µM to 0.5 nM). The cells incubated in Neutral medium serve as negative control of the assay. The cells incubated in Induction medium and without inhibitor serve as the positive control of the assay. The incubation is carried out for 16 h at 37° C. in a cell culture incubator. 200 µL of medium are transferred to U-bottom polypropylene 96-well plates containing 25 µL of 30% TCA, incubated 30 minutes at 60° C. and centrifuged at 3400 g for 5 minutes. 150 µL of the clear supernatant is transferred to a polystyrene 96-well plate containing 50 µL of 4% (w/v) of p-dimethylaminobenzaldehyde in acetic acid, incubated for 10 min. Kynurenine concentration is determined by measuring the absorbance at 480 nm.

To measure the toxicity of each compound after 16 h incubation with cells, cell viability is measured via a WST-1 assay (Roche) according to instructions from the manufacturer. Briefly, after the incubation with each compound, medium is aspirated and replaced with 100 mL of WST-1 reagent, and incubated 30 min at 37° C. Absorbance at 540 nm is correlated with the number of viable cells. Determination of $IC_{50}$ (Kynurenine assay) or $LD_{50}$ (WST-1 assay) is performed via non-linear regression analysis using GraphPad Prism software.

Example 16 Reversal of IDO-Mediated Suppression of T-Cell Proliferation by IDO Inhibitors Human monocytes were collected from peripheral mononuclear cells by leukoapheresis and cultured overnight at $10^6$ cells/well in a 96-well plate in RPMI 1640 medium supplemented with 10% fetal calf serum and 2 mM L-glutamine. Adherent cells were retained and cultured for 7 days with 200 ng/ml IL-4, 100 ng/ml GM-CSF. Cells were matured for 2 days with a cytokine cocktail containing TNF-α, IL-1β, IL-6 and PGE2 for additional 2 days to induce dendritic cell maturation. At the end of maturation, loosely adherent cells were detached by gentle aspiration and plated in V-bottom 96 well plates, at 5000 cells/well. These cells are >80% IDO+ dendritic cells. Human allogeneic T cells ($3\times10^5$) from normal donors were resuspended in RPMI 1640 supplemented with 100-200 U/mL IL-2 and 100 ng/mL anti-CD3 antibody and added to the wells. Serial dilutions of IDO compounds dissolved in phenol red-free RPMI was added to yield a final concentration of IDOi between 500 and 1 µM. After incubation for 2-4 days, T cell proliferation was measured by BrdU incorporation assay after an overnight pulse with BrdU labeling mix (Roche Molecular Biochemicals). At the en of the pulse, the cells were fixed and incubated with 100 µL/well anti-BrdU-POD antibody following the instructions from the manufacturer. Plates were read in a microplate reader.

Alternatively, testing of IDO inhibitors in an in vitro mouse model of IDO-mediated suppression of T cell proliferation is performed by the following procedure. C57bl6 mice are inoculated with $1\times10^6$ B78H1-GMCSF tumor cells in the right flank. After 10-12 days, tumor draining lymph nodes are collected and cells are stained with anti-CD11c and anti-B220 monoclonal antibodies. Cells are sorted by high-speed fluorescence activated cell sorting and the CD11c+/B220+ plasmacytoid dendritic cells are collected and seeded at 2000 cells/well in 96 well V-bottom plates. Splenocytes are collected from BM3 transgenic mice (in CBA background) and collected by nylon wool enrichment. BM3 T cells ($10^5$ cells/well) are added to each well in 200 µL of RPMI, 10% FCS, 50 µM β-mercaptoethanol. Alternatively, T cells are obtained from spleens of OT-I transgenic mice and added to the culture in combination with OVA peptide. IDO inhibitors are added dissolved in RPMI at final concentrations ranging from 1 mM to 10 nM. After 3 days of stimulation, cells are pulsed by 16 h with BrdU or $^3$H-thymidine. Cells are collected, fixed and tested for BrdU incorporation following the instructions from the BrdU labeling kit manufacturer (Roche Diagnostics). If $^3$H-thymidine is used to measure T cell proliferation, cells are harvested and dpm counts are measured in a scintillation counter following procedures widely known in the art. Control CD11c$^+$ cells taken from the contralateral lymph node or CD11c$^+$/B220$^-$ cells (IDO$^-$ population) from the TDLN are used as positive control for proliferation.

Example 17 In Vivo Testing of IDO Inhibitors for Antitumor Activity in Combination with Chemotherapeutic Agents In vivo anti-tumor efficacy can be tested using modified tumor allograft protocols. For instance, it has been described in the literature that IDO inhibition can syngerize with cytotoxic chemotherapy in immune-competent mice. Due to different susceptibilities of different tumor cell lines to chemotherapeutic drugs and to immune mediated rejection, each IDO inhibitor is tested alone and in combination with 2 different chemotherapeutic drugs in 4 different animal tumor models, represented by 4 different mouse tumor cell lines, of different tissue origin (colorectal, bladder, mammary and lung carcinoma), implanted subcutaneously in syngeneic strains of mice. These cell lines have been selected based on their known susceptibility to chemotherapeutic drugs, their partial response to IDO inhibitors as single agents, their presumed pattern of IDO expression according to their tissue of origin, and their ability to elicit an immune reaction.

For every animal tumor model, 2 different chemotherapeutic drugs are tested in separate groups of mice according to the following list: 1] LLC tumor: cyclophosphamide and paclitaxel; 2] EMT6 tumor: cyclophosphamide and paclitaxel; 3] CT26 tumor: cyclophosphamide and doxorubicin; 4] MB49 tumor: cyclophosphamide and gemcitabine; and 5] Pan02 pancreatic cell tumor: gembicitabine and cyclophosphamide.

The following chemotherapeutic drugs are used, at the indicated doses. The maximum tolerated dose for the following chemotherapeutic agents in mice depends on the formulation, concentration, frequency of administration, route of administration and number of doses. The chemotherapeutic drugs administered in conjunction with each IDO inhibitor drug are: 1] Paclitaxel: 20 mg/kg/day i.p, every 4 days, 4 times (q4d×4) (in Cremophor); 2] Doxorubicin: 5 mg/kg, once a week for 3 weeks (q7d×3); 3] Cyclophosphamide (CTX): 100 mg/kg, I.P., every 4 days, 4 times (q4d×4); 4] Gemcitabine: 80 mg/kg every 4 days, 4 times, i.p. (q4d×4).

All animals receive a subcutaneous injection of a tumor forming dose of live tumor cells (~50000-1000000 cells) suspended in 0.1 mL of PBS or saline on day 1. Subcutaneous injection forms a localized tumor that allows monitoring tumor growth over time.

To mimic the effect of IDO inhibitor drugs as therapeutic compositions, administration of IDO inhibitor drugs begins at day 5-8 after tumor inoculation. Dosing, route of administration, dosing frequency varies depending on the toxicity and pharmacokinetics profile of each drug. Duration of the treatment is 2 weeks. Most preferably, drug is administered continuously via oral gavage or dissolution in the drinking water. Alternatively, subcutaneous slow release pellets or osmotic pumps containing 100 mg of each drug are implanted under the skin by surgical procedure. IDO inhibitor drug are administered at the maximum tolerated dose or at a concentration corresponding to the $LD_{50}$.

Example 18: IDO and TDO Inhibitory Activity

| Compound # | Structure | IDO IC50 | TDO IC50 |
|---|---|---|---|
| 70 | 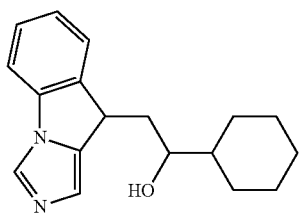 [SMILES: OC(CC1c2ccccc2-n2cncc21)C1CCCCC1] | A | A |
| 27 | 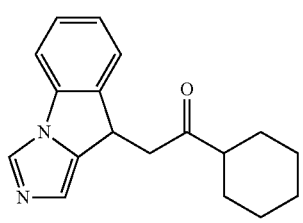 [SMILES: O=C(CC1c2ccccc2-n2cncc21)C1CCCCC1] | B | A |

-continued

| Compound # | Structure | IDO IC50 | TDO IC50 |
|---|---|---|---|
| 101 | 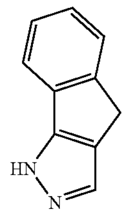 [SMILES: c1ccc2c(c1)Cc1cn[nH]c1-2] | D | B |
| 66 | 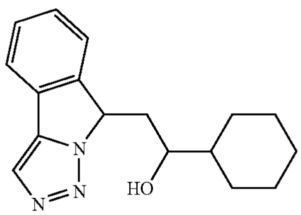 [SMILES: OC(CC1c2ccccc2-c2cnnn21)C1CCCCC1] | C | C |
| 53 | 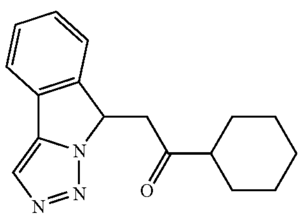 [SMILES: O=C(CC1c2ccccc2-c2cnnn21)C1CCCCC1] | C | C |
| 54 | 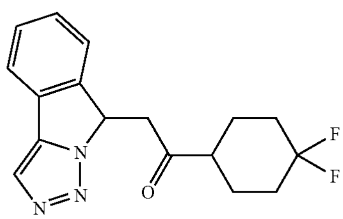 [SMILES: O=C(CC1c2ccccc2-c2cnnn21)C1CCC(F)(F)CC1] | D | D |
| 67 | 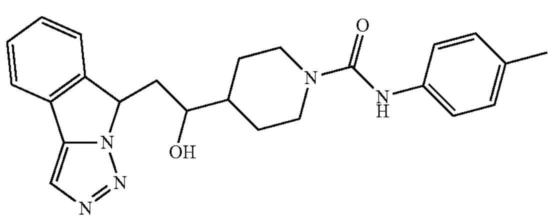 [SMILES: Cc1ccc(NC(=O)N2CCC(C(O)CC3c4ccccc4-c4cnnn43)CC2)cc1] | C | C |
| 68 | 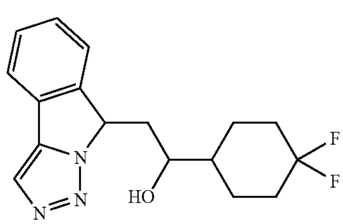 | C | B |
| 69 | 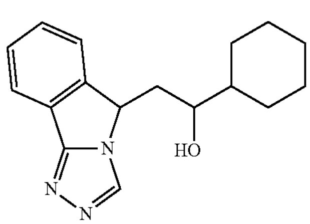 [SMILES: OC(CC1c2ccccc2-c2nncn21)C1CCCCC1] | D | D |

-continued

| Compound # | Structure | IDO IC50 | TDO IC50 |
|---|---|---|---|
| 43 | 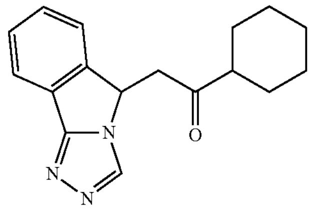 [SMILES: O=C(CC1c2ccccc2-c2nncn21)C1CCCCC1] | D | D |

IC50 ranges: A: <1 µM; B: 1-1 µM; C: 10-10 µM; D: >10 µM

Example 19: Additional Examples of Compounds of Formula (I)

| # | Structure | Name |
|---|---|---|
| 102 | 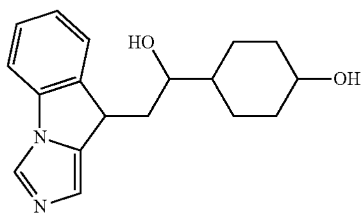 [SMILES: OC1CCC(C(O)CC2c3ccccc3-n3cncc32)CC1] | 4-(1-hydroxy-2-(9H-imidazo[1,5-a]indol-9-yl)ethyl)cyclohexan-1-ol |
| 103 | 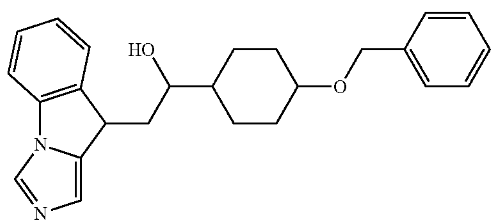 [SMILES: OC(CC1c2ccccc2-n2cncc21)C1CCC(OCc2ccccc2)CC1] | 1-(4-(benzyloxy)cyclohexyl)-2-(9H-imidazo[1,5-a]indol-9-yl)ethan-1-ol |
| 104 | 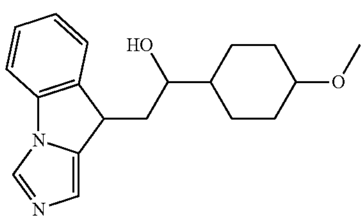 [SMILES: COC1CCC(C(O)CC2c3ccccc3-n3cncc32)CC1] | 2-(9H-imidazo[1,5-a]indol-9-yl)-1-(4-methoxycyclohexyl)ethan-1-ol |
| 105 | 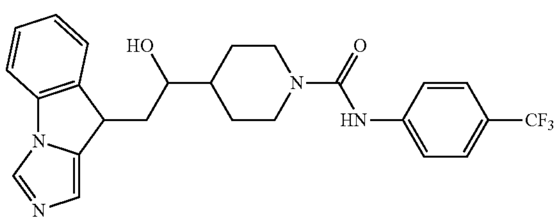 [SMILES: O=C(Nc1ccc(C(F)(F)F)cc1)N1CCC(C(O)CC2c3ccccc3-n3cncc32)CC1] | 4-(1-hydroxy-2-(9H-imidazo[1,5-a]indol-9-yl)ethyl)-N-(4-(trifluoromethyl)phenyl)piperidine-1-carboxamide |
| 106 | 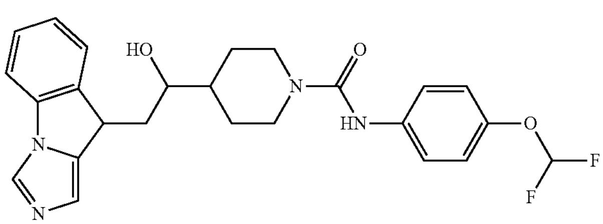 [SMILES: O=C(Nc1ccc(OC(F)F)cc1)N1CCC(C(O)CC2c3ccccc3-n3cncc32)CC1] | N-(4-(difluoromethoxy)phenyl)-4-(1-hydroxy-2-(9H-imidazo[1,5-a]indol-9-yl)ethyl)piperidine-1-carboxamide |

| # | Structure | Name |
|---|---|---|
| 107 | 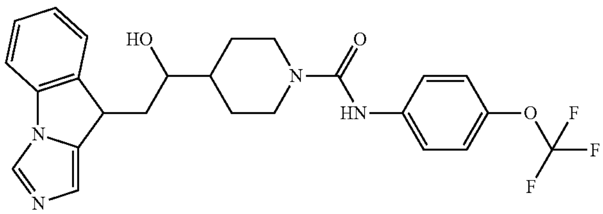 [SMILES: O=C(Nc1ccc(OC(F)(F)F)cc1)N1CCC(C(O)CC2c3ccccc3-n3cncc32)CC1] | 4-(1-hydroxy-2-(9H-imidazo[1,5-a]indol-9-yl)ethyl)-N-(4-(trifluoromethoxy)phenyl)piperidine-1-carboxamide |
| 108 | 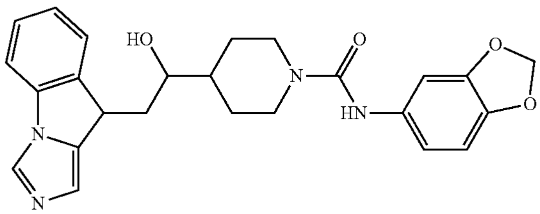 [SMILES: O=C(Nc1ccc2c(c1)OCO2)N1CCC(C(O)CC2c3ccccc3-n3cncc32)CC1] | N-(benzo[d][1,3]dioxol-5-yl)-4-(1-hydroxy-2-(9H-imidazo[1,5-a]indol-9-yl)ethyl)piperidine-1-carboxamide |
| 109 | 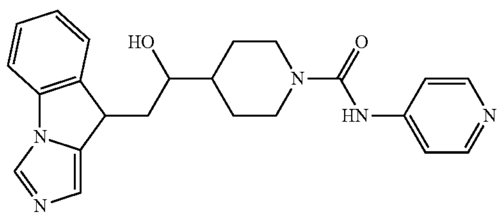 [SMILES: O=C(Nc1ccncc1)N1CCC(C(O)CC2c3ccccc3-n3cncc32)CC1] | 4-(1-hydroxy-2-(9H-imidazo[1,5-a]indol-9-yl)ethyl)-N-(pyridin-4-yl)piperidine-1-carboxamide |
| 110 | 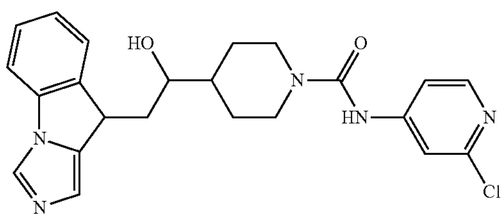 [SMILES: O=C(Nc1ccnc(Cl)c1)N1CCC(C(O)CC2c3ccccc3-n3cncc32)CC1] | N-(2-chloropyridin-4-yl)-4-(1-hydroxy-2-(9H-imidazo[1,5-a]indol-9-yl)ethyl)piperidine-1-carboxamide |
| 111 | 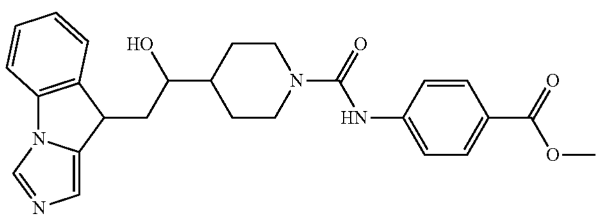 [SMILES: COC(=O)c1ccc(NC(=O)N2CCC(C(O)CC3c4ccccc4-n4cncc43)CC2)cc1] | methyl 4-(4-(1-hydroxy-2-(9H-imidazo[1,5-a]indol-9-yl)ethyl)piperidine-1-carboxamido)benzoate |
| 112 | 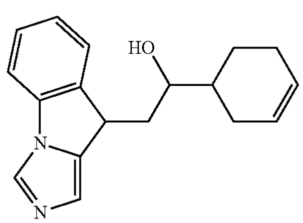 [SMILES: OC(CC1c2ccccc2-n2cncc21)C1CC=CCC1] | 1-(cyclohex-3-en-1-yl)-2-(9H-imidazo[1,5-a]indol-9-yl)ethan-1-ol |
| 113 | 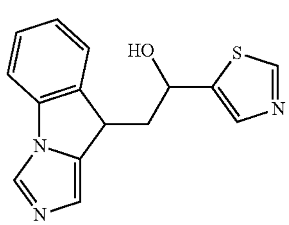 [SMILES: OC(CC1c2ccccc2-n2cncc21)c1cncs1] | 2-(9H-imidazo[1,5-a]indol-9-yl)-1-(thiazol-5-yl)ethan-1-ol |

-continued
| # | Structure | Name |
|---|---|---|
| 114 | 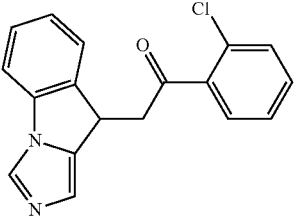 [SMILES: O=C(CC1c2ccccc2-n2cncc21)c1ccccc1Cl] | 1-(2-chlorophenyl)-2-(9H-imidazo[1,5-a]indol-9-yl)ethan-1-one |
| 115 | 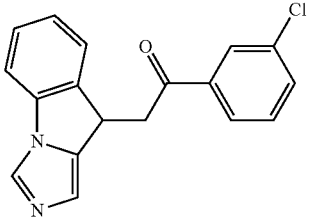 [SMILES: O=C(CC1c2ccccc2-n2cncc21)c1cccc(Cl)c1] | 1-(3-chlorophenyl)-2-(9H-imidazo[1,5-a]indol-9-yl)ethan-1-one |
| 116 | 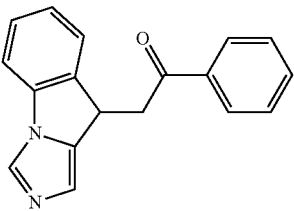 [SMILES: O=C(CC1c2ccccc2-n2cncc21)c1ccccc1] | 2-(9H-imidazo[1,5-a]indol-9-yl)-1-phenylethan-1-one |
| 117 | 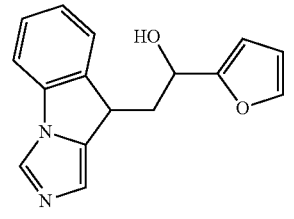 [SMILES: OC(CC1c2ccccc2-n2cncc21)c1ccco1] | 1-(furan-2-yl)-2-(9H-imidazo[1,5-a]indol-9-yl)ethan-1-ol |
| 118 | 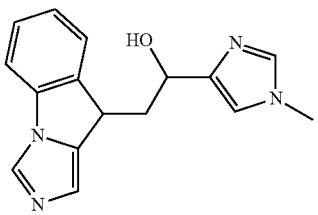 [SMILES: Cn1cnc(C(O)CC2c3ccccc3-n3cncc32)c1] | 2-(9H-imidazo[1,5-a]indol-9-yl)-1-(1-methyl-1H-imidazol-4-yl)ethan-1-ol |
| 119 | 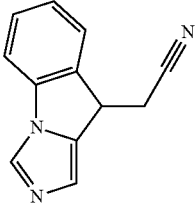 [SMILES: N#CCC1c2ccccc2-n2cncc21] | 2-(9H-imidazo[1,5-a]indol-9-yl)acetonitrile |
| 120 | 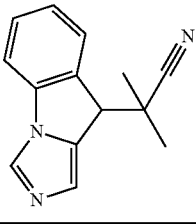 | 2-(9H-imidazo[1,5-a]indol-9-yl)-2-methylpropanenitrile |

We claim:

1. A composition comprising a first compound and a second compound, wherein the first compound is of formula (I), $$\text{(I)}$$

or a tautomer or pharmaceutically acceptable salt thereof, and the second compound is a therapeutic agent and n is 0, 1, 2, 3, or 4;
bond α is a single or double bond
ring A is an aromatic ring wherein
   i) V and X are N, W and Z are CH and Y is C; or
   ii) V, Y and Z are N, W is CH and X is C; or
   iii) V, W and Y are N, X is C and Z is CH; or
   iv) V and W are N or NH, X and Y are C and Z is CH;
each $R^1$ is independently halogen, cyano, nitro, $C_{1-6}$alkyl, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;
$R^2$ is —$C_{1-4}$alkyl-$R^A$ or —$C_{2-4}$alkenyl-$R^3$ when bond α is a single bond; and
$R^2$ is =C(H)$R^A$ when bond α is a double bond;
wherein
   $R^A$ is —CN, —C(O)$R^3$, —C(O)O$R^3$, —C(O)N($R^3$)($R^C$), —C(O$R^B$)($R^3$)($R^C$), —C(NHR$^B$)($R^3$)($R^C$), or —C(=N—O$R^C$)$R^3$, wherein
      $R^B$ is hydrogen, $C_{1-6}$alkyl, $C_{1-6}$haloalkyl, —$C_{1-6}$alkyl-$R^{B1}$, —C(O)$R^3$, —S(O)$_2$R$^3$, —C(O)(CH$_2$)$_{1-4}$COOR, —C(O)CH(NH$_2$)($R^D$), —S(O)$_2$OR$^3$, —S(O)$_2$N($R^3$)$_2$, —CH$_2$—OP(O)$_2$(OR)$_2$, or —P(O)(OR$^3$)$_2$, wherein
      $R^{B1}$ is cyano, nitro, $C_{1-6}$alkyl, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;
      $R^D$ is hydrogen, methyl, —CH(CH$_3$)$_2$, —CH$_2$CH(CH$_3$)$_2$, —CH(CH$_3$)(CH$_2$CH$_3$), benzyl, 4-hydroxybenzyl, —CH$_2$(3-indolyl), —CH$_2$SH, —CH$_2$CH$_2$SCH$_3$, —CH$_2$OH, —CH(CH$_3$)OH, —(CH$_2$)$_4$—NH$_2$, —(CH$_2$)$_3$—N(H)C(=NH)NH$_2$, —CH$_2$(4-imidazolyl), —CH$_2$COOH, —CH$_2$CH$_2$COOH, —CH$_2$CONH$_2$, or —CH$_2$CH$_2$CONH$_2$;
each $R^3$ is independently hydrogen, $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl-, heteroaryl$C_{1-6}$ alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$alkyl-, wherein the alkyl, $C_{3-8}$cycloalkyl, $C_{3-8}$cycloalkenyl, 3-10 membered heterocyclyl, $C_{3-8}$cycloalkyl$C_{1-6}$alkyl-, $C_{3-8}$cycloalkenyl$C_{1-6}$alkyl-, and (3-10 membered heterocyclyl)$C_{1-6}$alkyl- are each optionally and independently substituted by one =$R^{32}$ group and each optionally substituted and independently by one, two, three, or four $R^{31}$ groups;
the aryl, heteroaryl, aryl$C_{1-6}$alkyl-, and heteroaryl$C_{1-6}$alkyl- groups, are each optionally substituted by one, two, three, or four $R^{31}$ groups;
wherein
each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R—, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$, wherein R$^{33}$ is cyano, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

R$^{32}$ is =O, =S, =N(R), =N(OR), =C(R$^{34}$)$_2$, =(spiro-C$_{3-8}$cycloalkyl), or =(spiro-(3-10 membered heterocyclyl)), wherein each R$^{34}$ is independently hydrogen, halogen, C$_{1-6}$alkyl, C$_{1-6}$haloalkyl, C$_{3-8}$cycloalkyl, or 3-10 membered heterocyclyl;

or both R$^{34}$ taken together with the atom to which they are both attached form a monocyclic C$_{3-8}$cycloalkyl or monocyclic 3-8 membered heterocyclyl;

R$^C$ is hydrogen or C$_{1-6}$alkyl;

and each R is independently hydrogen or R$^{10}$, wherein

R$^{10}$ is C$_{1-6}$alkyl, C$_{1-6}$haloalkyl, aryl, heteroaryl, C$_{3-8}$cycloalkyl, C$_{3-8}$cycloalkenyl, 3-10 membered heterocyclyl, arylC$_{1-6}$alkyl, heteroarylC$_{1-6}$alkyl-, C$_{3-8}$cycloalkylC$_{1-6}$alkyl-, C$_{3-8}$cycloalkenylC$_{1-6}$alkyl-, or (3-10 membered heterocyclyl)C$_{1-6}$alkyl-, each R$^{10}$ optionally substituted by one, two, three, or four groups that are each independently halogen, cyano, nitro, C$_{1-6}$alkyl, C$_{1-6}$haloalkyl, —OR$^{11}$, —N(R$^{11}$)$_2$, —SR$^{11}$, —C(O)OR$^{11}$, —C(O)N(R$^{11}$)$_2$, —C(O)R$^{11}$, —S(O)R$^{11}$, —S(O)OR$^{11}$, —S(O)N(R$^{11}$)$_2$, —S(O)$_2$R$^{11}$, —S(O)$_2$OR$^{11}$, —S(O)$_2$N(R$^{11}$)$_2$, —OC(O)R$^{11}$, —OC(O)OR$^{11}$, —OC(O)N(R$^{11}$)$_2$, —N(R$^{11}$)C(O)R$^{11}$, —N(R$^{11}$)C(O)OR$^{11}$, or —N(R$^{11}$)C(O)N(R$^{11}$)$_2$, wherein each R$^{11}$ is independently hydrogen or C$_{1-6}$alkyl, and wherein the second therapeutic agent is a chemotherapeutic or other anti-cancer agent.

2. The composition of claim 1 wherein bond α is a single bond.

3. The composition of claim 1 wherein V and X are N, W and Z are CH and Y is C.

4. The composition of claim 1 wherein V, Y and Z are N, W is CH and X is C.

5. The composition of claim 1 wherein V, W and Y are N, X is C and Z is CH.

6. The composition of claim 1 wherein V and W are N or NH, X and Y are C and Z is CH.

7. The composition of claim 1, wherein R$^2$ is —C$_{1-4}$alkyl-R$^4$.

8. The composition of claim 1, wherein R$^2$ is —CH$_2$—R$^4$, —CH$_2$CH$_2$—R$^4$, —C(H)(CH$_3$)CH$_2$—R$^4$, or —C(H)=C(H)R$^3$.

9. The composition of claim 8, wherein R$^2$ is —CH$_2$—R$^4$.

10. The composition of claim 1, wherein R$^4$ is —C(O)R$^3$ or —C(OR$^B$)(R$^3$)(R$^C$).

11. The composition of claim 1, wherein R$^4$ is —C(NHR$^B$)(R$^3$)(R$^C$), or —C(=N—OR$^C$)R$^3$.

12. The composition of claim 1, wherein R$^4$ is —C(NHR$^B$)(R$^3$)(R$^C$), wherein R$^B$ is hydrogen, C$_{1-6}$alkyl, or —C(O)C$_{1-6}$alkyl.

13. The composition of claim 1, wherein R$^4$ is —C(OR$^B$)(R$^3$)(R$^C$).

14. The composition of claim 1, wherein R$^4$ is —CH(OH)(R$^3$).

15. The composition of claim 1, wherein R$^3$ is hydrogen.

16. The composition of claim 1, wherein R$^3$ is aryl, heteroaryl, C$_{3-8}$cycloalkyl, C$_{3-8}$cycloalkenyl, 3-10 membered heterocyclyl, or C$_{3-8}$cycloalkylC$_{1-6}$alkyl-, wherein the C$_{3-8}$cycloalkyl, C$_{3-8}$cycloalkenyl, 3-10 membered heterocyclyl, and C$_{3-8}$cycloalkylC$_{1-6}$ alkyl-, are each optionally and independently substituted by one =R$^{32}$ group and each optionally and independently substituted by one or two R$^{31}$ groups; and the aryl and heteroaryl groups, are each optionally substituted by one or two R$^{31}$ groups.

17. The composition of claim 1, wherein R$^3$ is phenyl, a five or six membered heteroaryl, monocyclic C$_{5-8}$cycloalkyl, monocyclic C$_{5-8}$cycloalkenyl, a five or six membered monocyclic heterocyclyl, or (monocyclic C$_{5-8}$cycloalkyl)C$_{1-6}$ alkyl-, wherein the C$_{5-8}$cycloalkyl, C$_{5-8}$cycloalkenyl, 5-6 membered heterocyclyl, and C$_{5-8}$cycloalkylC$_{1-6}$ alkyl-, are each optionally and independently substituted by one =R$^{32}$ group and each optionally and independently substituted by one or two R$^{31}$ groups; and the phenyl and heteroaryl groups, are each optionally substituted by one or two R$^{31}$ groups.

18. The composition of claim 1, wherein R$^3$ is phenyl or a five or six membered heteroaryl, each optionally substituted by one or two R$^{31}$ groups.

19. The composition of claim 1, wherein R$^3$ is monocyclic C$_{5-8}$cycloalkyl, monocyclic C$_{5-8}$cycloalkenyl, a five or six membered monocyclic heterocyclyl, or (monocyclic C$_{5-8}$cycloalkyl)C$_{1-6}$alkyl-, each optionally substituted by one =R$^{32}$ group and one or two R$^{31}$ groups.

20. The composition of claim 1, wherein R$^3$ is

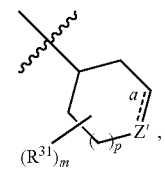

wherein bond a is a single bond or a double bond;

m is 0, 1, or 2;

p is 0 or 1; and when bond "a" is a single bond, then Z' is —C(R$^{36}$)$_2$—, —C(=R$^{32}$)—, —N(R$^{35}$)—, or —O—, wherein R$^{35}$ is hydrogen, C$_{1-6}$alkyl, —C(O)R, —S(O)$_2$R, —C(O)OR, —C(O)N(R)$_2$, —S(O)$_2$OR, or —S(O)$_2$N(R)$_2$; and when bond a is a double bond, then Z' is —C(R$^{36}$)= or —N=;

each R$^{36}$ is independently hydrogen or R$^{31}$.

21. The composition of claim 20, wherein bond a is a single bond; and Z' is —N(R$^{35}$)— or —O—.

22. The composition of claim 1 where in the compound is of the formula,

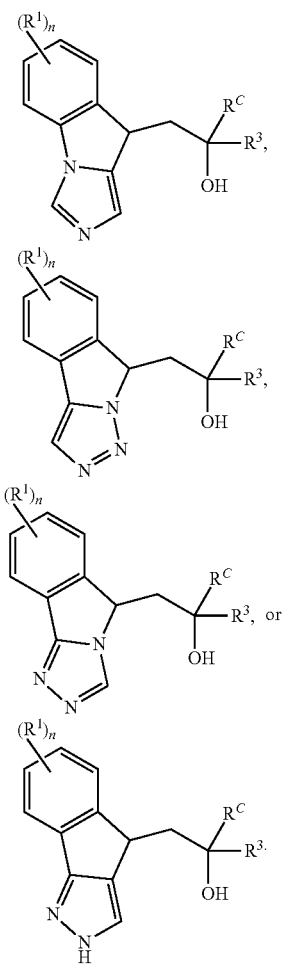

23. The composition of claim 22, wherein
R$^C$ is hydrogen and
R$^3$ is aryl, heteroaryl, C$_{3-8}$cycloalkyl, C$_{3-8}$cycloalkenyl, or 3-10 membered heterocyclyl, wherein
the C$_{3-8}$cycloalkyl, C$_{3-8}$cycloalkenyl, and 3-10 membered heterocyclyl are each optionally substituted by one =R$^{32}$ group and one, two, three, or four R$^{31}$ groups; and
the aryl and heteroaryl are each optionally substituted by one, two, three, or four R$^{31}$ groups.

24. The composition of claim 22, wherein R$^3$ is

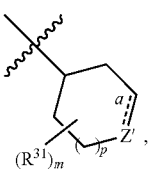

wherein
bond a is a single bond or a double bond;
m is 0, 1, or 2;
p is 0 or 1; and
when bond "a" is a single bond, then Z' is —C(R$^{36}$)$_2$—, —C(=R$^{32}$)—, —N(R$^{35}$)—, or —O—, wherein R$^{35}$ is hydrogen, C$_{1-6}$alkyl, —C(O)R, —S(O)$_2$R, —C(O)OR, —C(O)N(R)$_2$, —S(O)$_2$OR, or —S(O)$_2$N(R)$_2$; and
when bond a is a double bond, then Z' is —C(R$^{36}$)= or —N=;
each R$^{36}$ is independently hydrogen or R$^{31}$.

25. The composition according to claim 1 further comprising a pharmaceutically acceptable diluent, excipient, or carrier.

26. A method for treating cancer in a subject in need thereof, comprising administering an effective amount of a composition according to claim 1 to the subject.

27. The method of claim 26, wherein the wherein the subject is also in need of treatment for immunosuppression associated with cancer or treatment of the cancer.

28. The composition according to claim 1, wherein
R$^2$ is =C(H)R$^A$ when bond α is a double bond;
R$^A$ is —C(O)R$^3$ or —C(OR$^B$)(R$^3$)(R$^C$);
R$^B$ is hydrogen, C$_{1-4}$alkyl, or C$_{1-4}$haloalkyl; and,
R$^C$ is hydrogen or C$_{1-4}$alkyl.

29. The composition according to claim 1, wherein
α is a single bond and R$^2$ is —C$_{1-4}$alkyl-R$^A$ or —C$_{2-4}$alkenyl-R$^3$;
R$^A$ is —C(O)R$^3$, —C(OR$^B$)(R$^3$)(R$^C$), or —C(NHR$^B$)(R$^3$)(R$^C$), or —C(=N—OR$^C$)R$^3$;
R$^B$ is hydrogen, C$_{1-4}$alkyl, or C$_{1-4}$haloalkyl; and,
R$^C$ is hydrogen or C$_{1-4}$alkyl.

30. The composition according to claim 22 wherein
R$^3$ is aryl, heteroaryl, C$_{3-8}$cycloalkyl, C$_{3-8}$cycloalkenyl, or 3-10 membered heterocyclyl, wherein the C$_{3-8}$cycloalkyl, C$_{3-8}$cycloalkenyl, and 3-10 membered heterocyclyl are each optionally substituted by one =R$^{32}$ group and one, two, three, or four R$^{31}$ groups; and
the aryl and heteroaryl are each optionally substituted by one, two, three, or four R$^{31}$ groups.

31. The composition according to claim 22 wherein R$^3$ is phenyl, cyclopentyl, cyclohexyl, cyclohex-1-en-1-yl, cyclohex-3-en-1-yl, furan-2-yl, furan-3-yl, tetrahydropyran-3-yl, tetrahydropyran-4-yl, piperidin-3-yl, piperidin-4-yl, imidazol-2-yl, imidazol-4-yl, thiazol-2-yl, thiazol-4-yl, thiazol-5-yl, each optionally substituted by one or two R$^{31}$ groups, and wherein the cyclopentyl, cyclohexyl, cyclohexenyl, and piperidinyl groups are each optionally substituted by one =R$^{32}$ group.

32. The composition according to claim 22 wherein R$^3$ is

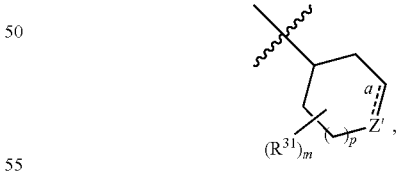

wherein bond a is a single bond or a double bond; m is 0, 1, or 2; p is 0 or 1; and wherein
when bond a is a single bond, then Z' is —C(R$^{36}$)$_2$—, —C(=R$^{32}$)—, —N(R$^{35}$)—, or —O—, wherein each R$^{36}$ is independently hydrogen or R$^{31}$; and
R$^{35}$ is hydrogen, C$_{1-6}$alkyl, —C(O)R, —S(O)$_2$R, —C(O)OR, —C(O)N(R)$_2$, —S(O)$_2$OR, or —S(O)$_2$N(R)$_2$;
and when bond a is a double bond, then Z' is —C(R$^{36}$)= or —N=.

33. The composition according to claim 5 wherein bond a is a single bond; and Z' is —C(R$^{36}$)$_2$.

34. The composition according to claim 1 in which V and X are N, W and Z are CH and Y is C.

35. The composition according to claim 1 wherein the compound of formula (I) is

| | | |
|---|---|---|
| 27 | 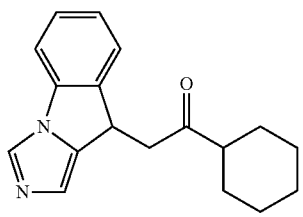 [SMILES: O=C(CC1c2ccccc2-n2cncc21)C1CCCCC1] | 1-cyclohexyl-2-(9H-imidazo[1,5-a]indol-9-yl)ethan-1-one, |
| 28 | 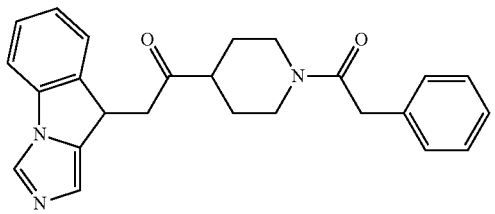 [SMILES: O=C(CC1c2ccccc2-n2cncc21)C1CCN(C(=O)Cc2ccccc2)CC1] | 1-(4-(2-(9H-imidazo[1,5-a]indol-9-yl)acetyl)piperidin-1-yl)-2-phenylethan-1-one, |
| 29 | 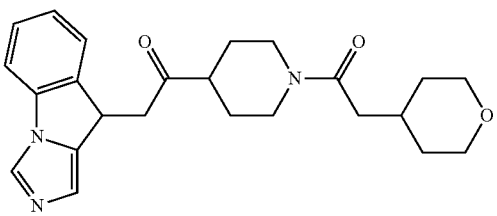 [SMILES: O=C(CC1c2ccccc2-n2cncc21)C1CCN(C(=O)CC2CCOCC2)CC1] | 1-(4-(2-(9H-imidazo[1,5-a]indol-9-yl)acetyl)piperidin-1-yl)-2-(tetrahydro-2H-pyran-4-yl)ethan-1-one, |
| 30 | 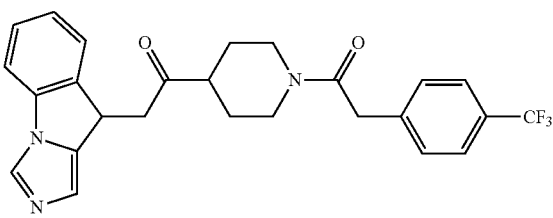 [SMILES: O=C(CC1c2ccccc2-n2cncc21)C1CCN(C(=O)Cc2ccc(C(F)(F)F)cc2)CC1] | 1-(4-(2-(9H-imidazo[1,5-a]indol-9-yl)acetyl)piperidin-1-yl)-2-(4-(trifluoromethyl)phenyl)ethan-1-one, |
| 31 | 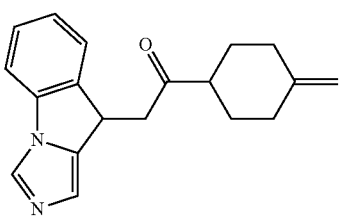 [SMILES: C=C1CCC(C(=O)CC2c3ccccc3-n3cncc32)CC1] | 2-(9H-imidazo[1,5-a]indol-9-yl)-1-(4-methylenecyclohexyl)ethan-1-one, |
| 32 | 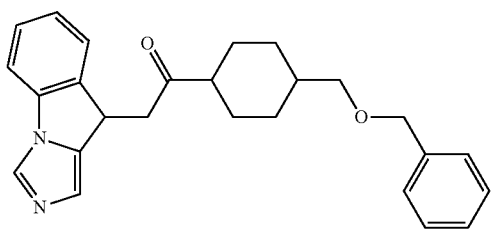 [SMILES: O=C(CC1c2ccccc2-n2cncc21)C1CCC(COCc2ccccc2)CC1] | 1-(4-((benzyloxy)methyl)cyclohexyl)-2-(9H-imidazo[1,5-a]indol-9-yl)ethan-1-one, |
| 33 | 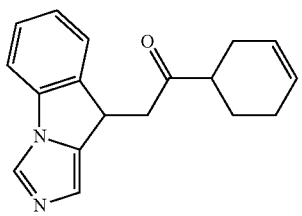 [SMILES: O=C(CC1c2ccccc2-n2cncc21)C1CC=CCC1] | 1-(cyclohex-3-en-1-yl)-2-(9H-imidazo[1,5-a]indol-9-yl)ethan-1-one, |

| | | |
|---|---|---|
| 34 | 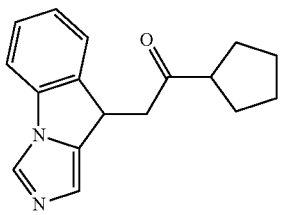 [SMILES: O=C(CC1c2ccccc2-n2cncc21)C1CCCC1] | 1-cyclopentyl-2-(9H-imidazo[1,5-a]indol-9-yl)ethan-1-one, |
| 35 | 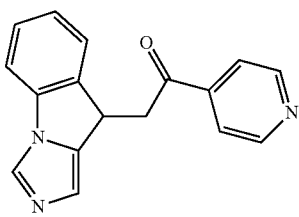 [SMILES: O=C(CC1c2ccccc2-n2cncc21)c1ccncc1] | 2-(9H-imidazo[1,5-a]indol-9-yl)-1-(pyridin-4-yl)ethan-1-one, |
| 36 | 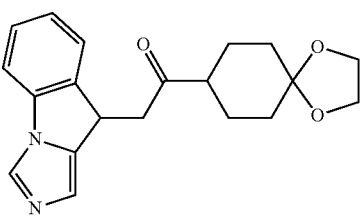 [SMILES: O=C(CC1c2ccccc2-n2cncc21)C1CCC2(CC1)OCCO2] | 2-(9H-imidazo[1,5-a]indol-9-yl)-1-(1,4-dioxaspiro[4.5]decan-8-yl)ethan-1-one, |
| 37 | 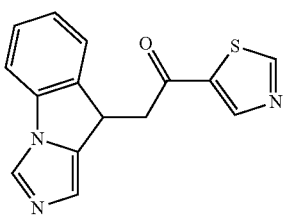 [SMILES: O=C(CC1c2ccccc2-n2cncc21)c1cncs1] | 2-(9H-imidazo[1,5-a]indol-9-yl)-1-(thiazol-5-yl)ethan-1-one, |
| 38 | 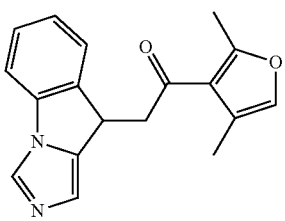 [SMILES: Cc1coc(C)c1C(=O)CC1c2ccccc2-n2cncc21] | 1-(2,4-dimethylfuran-3-yl)-2-(9H-imidazo[1,5-a]indol-9-yl)ethan-1-one, |
| 39 | 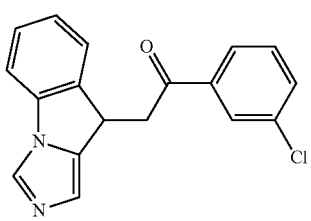 [SMILES: O=C(CC1c2ccccc2-n2cncc21)c1cccc(Cl)c1] | 1-(3-chlorophenyl)-2-(9H-imidazo[1,5-a]indol-9-yl)ethan-1-one, |
| 43 | 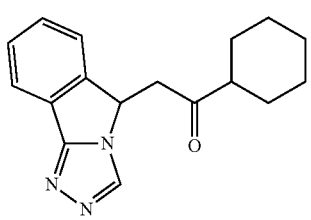 | 2-(5H-[1,2,4]triazolo[3,4-a]isoindol-5-yl)-1-cyclohexylethan-1-one, |

| # | | Name |
|---|---|---|
| 44 | 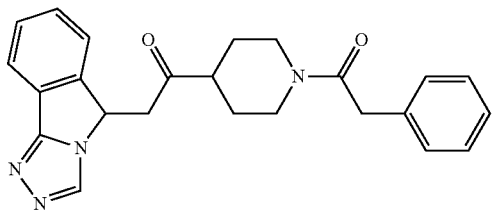 [SMILES: O=C(CC1c2ccccc2-c2nncn21)C1CCN(C(=O)Cc2ccccc2)CC1] | 1-(4-(2-(5H-[1,2,4]triazolo[3,4-a]isoindol-5-yl)acetyl)piperidin-1-yl)-2-phenylethan-1-one, |
| 45 | 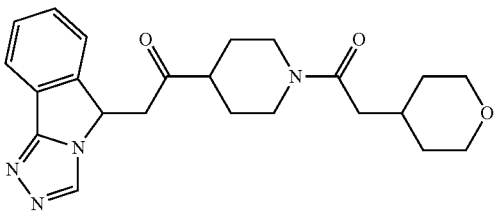 | 1-(4-(2-(5H-[1,2,4]triazolo[3,4-a]isoindol-5-yl)acetyl)piperidin-1-yl)-2-(tetrahydro-2H-pyran-4-yl)ethan-1-one, |
| 46 | 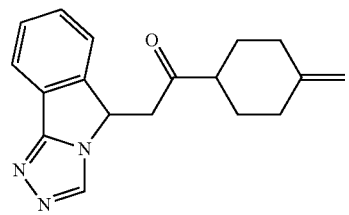 [SMILES: C=C1CCC(C(=O)CC2c3ccccc3-c3nncn32)CC1] | 2-(5H-[1,2,4]triazolo[3,4-a]isoindol-5-yl)-1-(4-methylenecyclohexyl)ethan-1-one, |
| 47 | 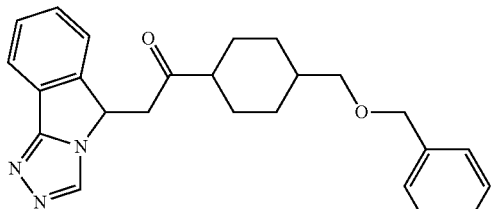 | 2-(5H-[1,2,4]triazolo[3,4-a]isoindol-5-yl)-1-(4-((benzyloxy)methyl)cyclohexyl)ethan-1-one, |
| 48 | 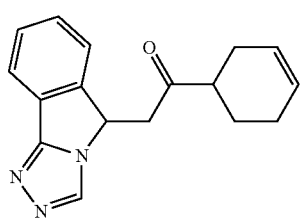 [SMILES: O=C(CC1c2ccccc2-c2nncn21)C1CC=CCC1] | 2-(5H-[1,2,4]triazolo[3,4-a]isoindol-5-yl)-1-(cyclohex-3-en-1-yl)ethan-1-one, |
| 49 | 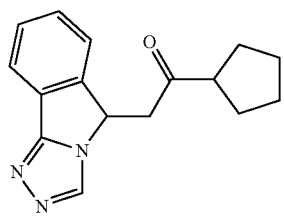 [SMILES: O=C(CC1c2ccccc2-c2nncn21)C1CCCC1] | 2-(5H-[1,2,4]triazolo[3,4-a]isoindol-5-yl)-1-cyclopentylethan-1-one, |
| 50 | 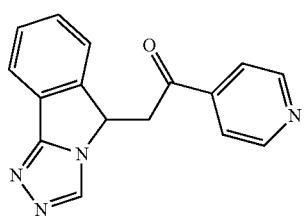 [SMILES: O=C(CC1c2ccccc2-c2nncn21)c1ccncc1] | 2-(5H-[1,2,4]triazolo[3,4-a]isoindol-5-yl)-1-(pyridin-4-yl)ethan-1-one, |

| 51 | 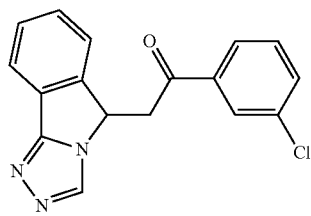 [SMILES: O=C(CC1c2ccccc2-c2nncn21)c1cccc(Cl)c1] | 2-(5H-[1,2,4]triazolo[3,4-a]isoindol-5-yl)-1-(3-chlorophenyl)ethan-1-one, |
| --- | --- | --- |
| 53 | 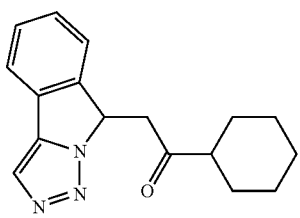 [SMILES: O=C(CC1c2ccccc2-c2cnnn21)C1CCCCC1] | 2-(8H-[1,2,3]triazolo[5,1-a]isoindol-8-yl)-1-cyclohexylethan-1-one, |
| 54 | 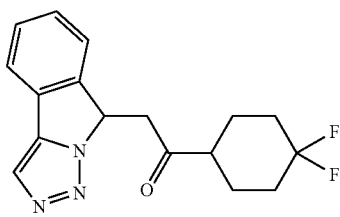 [SMILES: O=C(CC1c2ccccc2-c2cnnn21)C1CCC(F)(F)CC1] | 2-(8H-[1,2,3]triazolo[5,1-a]isoindol-8-yl)-1-(4,4-difluorocyclohexyl)ethan-1-one, |
| 55 | 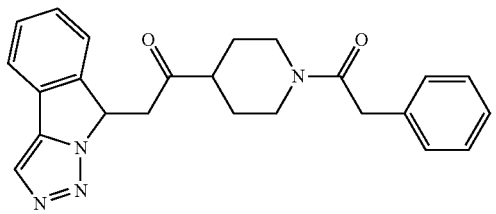 [SMILES: O=C(CC1c2ccccc2-c2cnnn21)C1CCN(C(=O)Cc2ccccc2)CC1] | 1-(4-(2-(8H-[1,2,3]triazolo[5,1-a]isoindol-8-yl)acetyl)piperidin-1-yl)-2-phenylethan-1-one, |
| 56 | 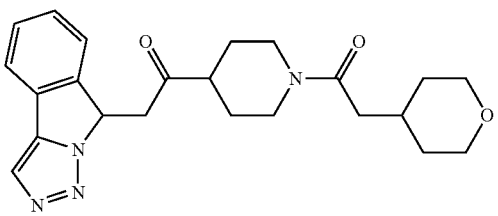 [SMILES: O=C(CC1c2ccccc2-c2cnnn21)C1CCN(C(=O)CC2CCOCC2)CC1] | 1-(4-(2-(8H-[1,2,3]triazolo[5,1-a]isoindol-8-yl)acetyl)piperidin-1-yl)-2-(tetrahydro-2H-pyran-4-yl)ethan-1-one, |
| 57 | 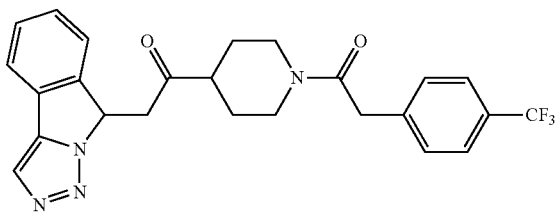 | 1-(4-(2-(8H-[1,2,3]triazolo[5,1-a]isoindol-8-yl)acetyl)piperidin-1-yl)-2-(4-(trifluoromethyl)phenyl)ethan-1-one, |
| 58 | 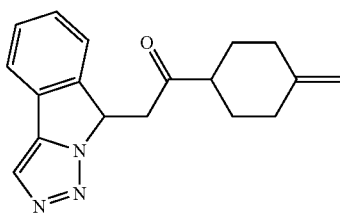 [SMILES: C=C1CCC(C(=O)CC2c3ccccc3-c3cnnn32)CC1] | 2-(8H-[1,2,3]triazolo[5,1-a]isoindol-8-yl)-1-(4-methylenecyclohexyl)ethan-1-one, |

| | | |
|---|---|---|
| 59 | 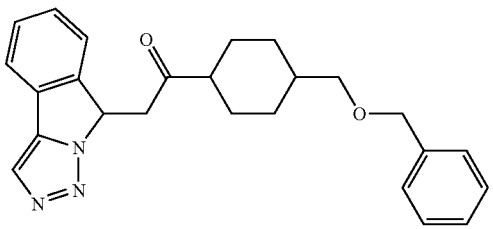 | 2-(8H-[1,2,3]triazolo[5,1-a]isoindol-8-yl)-1-(4-((benzyloxy)methyl)cyclohexyl)ethan-1-one, |
| 60 | 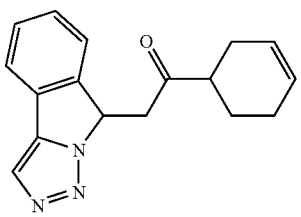 [SMILES: O=C(CC1c2ccccc2-c2cnnn21)C1CC=CCC1] | 2-(8H-[1,2,3]triazolo[5,1-a]isoindol-8-yl)-1-(cyclohex-3-en-1-yl)ethan-1-one, |
| 61 | 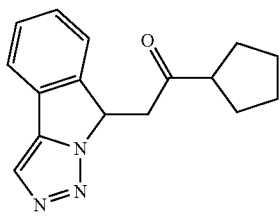 [SMILES: O=C(CC1c2ccccc2-c2cnnn21)C1CCCC1] | 2-(8H-[1,2,3]triazolo[5,1-a]isoindol-8-yl)-1-cyclopentylethan-1-one, |
| 62 | 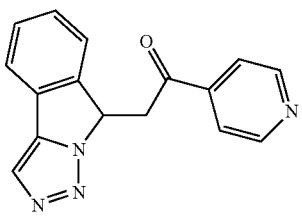 [SMILES: O=C(CC1c2ccccc2-c2cnnn21)c1ccncc1] | 2-(8H-[1,2,3]triazolo[5,1-a]isoindol-8-yl)-1-(pyridin-4-yl)ethan-1-one, |
| 63 | 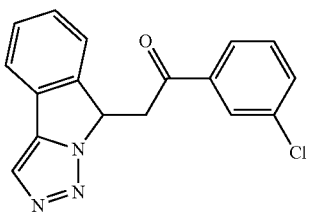 [SMILES: O=C(CC1c2ccccc2-c2cnnn21)c1cccc(Cl)c1] | 2-(8H-[1,2,3]triazolo[5,1-a]isoindol-8-yl)-1-(3-chlorophenyl)ethan-1-one, |
| 64 | 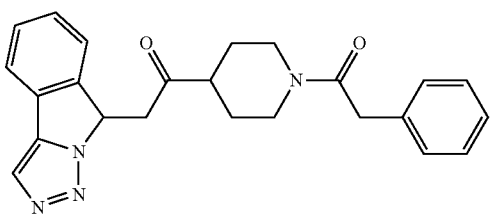 [SMILES: O=C(CC1c2ccccc2-c2cnnn21)C1CCN(C(=O)Cc2ccccc2)CC1] | 1-(4-(2-(8H-[1,2,3]triazolo[5,1-a]isoindol-8-yl)acetyl)piperidin-1-yl)-2-phenylethan-1-one, |
| 66 | 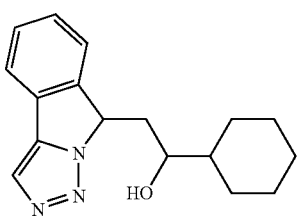 | 2-(8H-[1,2,3]triazolo[5,1-a]isoindol-8-yl)-1-cyclohexylethan-1-ol, |

| # | Name |
|---|---|
| 67 | 4-(2-(8H-[1,2,3]triazolo[5,1-a]isoindol-8-yl)-1-hydroxyethyl)-N-(p-tolyl)piperidine-1-carboxamide, |
| 68 | 2-(8H-[1,2,3]triazolo[5,1-a]isoindol-8-yl)-1-(4,4-difluorocyclohexyl)ethan-1-ol, |
| 69 | 2-(5H-[1,2,4]triazolo[3,4-a]isoindol-5-yl)-1-cyclohexylethan-1-ol, |
| 70 | 1-cyclohexyl-2-(9H-imidazo[1,5-a]indol-9-yl)ethan-1-ol, |
| 71 | 1-(4-(1-hydroxy-2-(9H-imidazo[1,5-a]indol-9-yl)ethyl)piperidin-1-yl)-2-phenylethan-1-one, |
| 72 | 1-(4-(1-hydroxy-2-(9H-imidazo[1,5-a]indol-9-yl)ethyl)piperidin-1-yl)-2-(tetrahydro-2H-pyran-4-yl)ethan-1-one, |
| 73 | 1-(4-(1-hydroxy-2-(9H-imidazo[1,5-a]indol-9-yl)ethyl)piperidin-1-yl)-2-(4-(trifluoromethyl)phenyl)ethan-1-one, |

| | | |
|---|---|---|
| 74 | 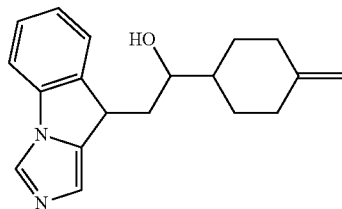 [SMILES: C=C1CCC(C(O)CC2c3ccccc3-n3cncc32)CC1] | 2-(9H-imidazo[1,5-a]indol-9-yl)-1-(4-methylenecyclohexyl)ethan-1-ol, |
| 75 | 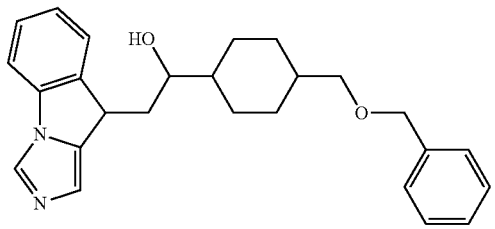 | 1-(4-((benzyloxy)methyl)cyclohexyl)-2-(9H-imidazo[1,5-a]indol-9-yl)ethan-1-ol, |
| 76 | 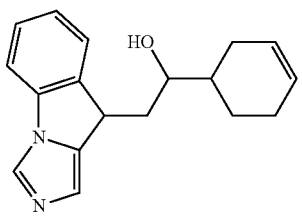 [SMILES: OC(CC1c2ccccc2-n2cncc21)C1CC=CCC1] | 1-(cyclohex-3-en-1-yl)-2-(9H-imidazo[1,5-a]indol-9-yl)ethan-1-ol, |
| 77 | 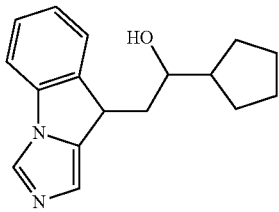 [SMILES: OC(CC1c2ccccc2-n2cncc21)C1CCCC1] | 1-cyclopentyl-2-(9H-imidazo[1,5-a]indol-9-yl)ethan-1-ol, |
| 78 | 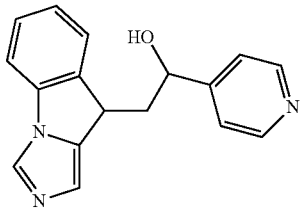 [SMILES: OC(CC1c2ccccc2-n2cncc21)c1ccncc1] | 2-(9H-imidazo[1,5-a]indol-9-yl)-1-(pyridin-4-yl)ethan-1-ol, |
| 79 | 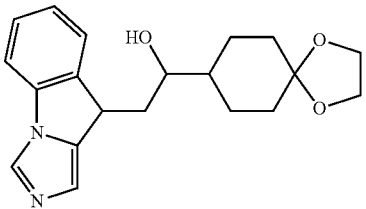 | 2-(9H-imidazo[1,5-a]indol-9-yl)-1-(1,4-dioxaspiro[4.5]decan-8-yl)ethan-1-ol, |
| 80 | 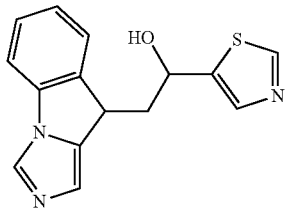 [SMILES: OC(CC1c2ccccc2-n2cncc21)c1cncs1] | 2-(9H-imidazo[1,5-a]indol-9-yl)-1-(thiazol-5-yl)ethan-1-ol, |

| | | |
|---|---|---|
| 81 | 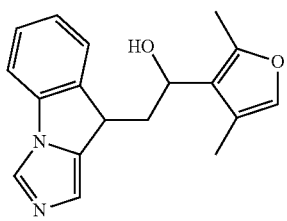 | 1-(2,4-dimethylfuran-3-yl)-2-(9H-imidazo[1,5-a]indol-9-yl)ethan-1-ol, |
| 82 | 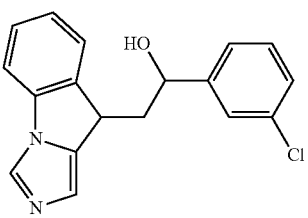 [SMILES: OC(CC1c2ccccc2-n2cncc21)c1cccc(Cl)c1] | 1-(3-chlorophenyl)-2-(9H-imidazo[1,5-a]indol-9-yl)ethan-1-ol, |
| 83 | 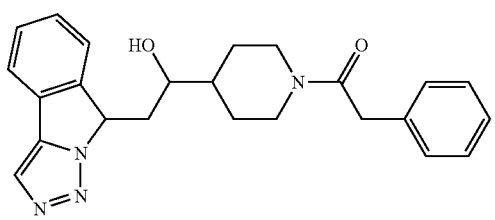 [SMILES: O=C(Cc1ccccc1)N1CCC(C(O)CC2c3ccccc3-c3cnnn32)CC1] | 1-(4-(2-(8H-[1,2,3]triazolo[5,1-a]isoindol-8-yl)-1-hydroxyethyl)piperidin-1-yl)-2-phenylethan-1-one, |
| 84 | 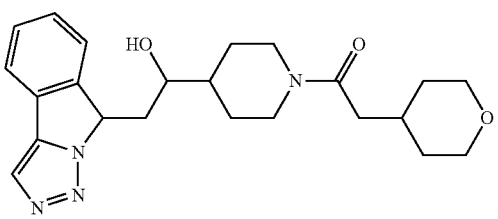 | 1-(4-(2-(8H-[1,2,3]triazolo[5,1-a]isoindol-8-yl)-1-hydroxyethyl)piperidin-1-yl)-2-(tetrahydro-2H-pyran-4-yl)ethan-1-one, |
| 85 | 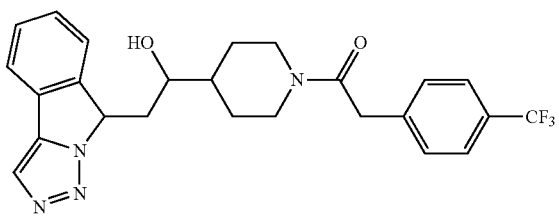 [SMILES: O=C(Cc1ccc(C(F)(F)F)cc1)N1CCC(C(O)CC2c3ccccc3-c3cnnn32)CC1] | 1-(4-(2-(8H-[1,2,3]triazolo[5,1-a]isoindol-8-yl)-1-hydroxyethyl)piperidin-1-yl)-2-(4-(trifluoromethyl)phenyl)ethan-1-one, |
| 86 | 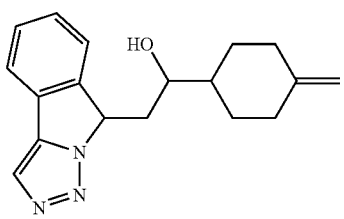 [SMILES: C=C1CCC(C(O)CC2c3ccccc3-c3cnnn32)CC1] | 2-(8H-[1,2,3]triazolo[5,1-a]isoindol-8-yl)-1-(4-methylenecyclohexyl)ethan-1-ol, |
| 87 | 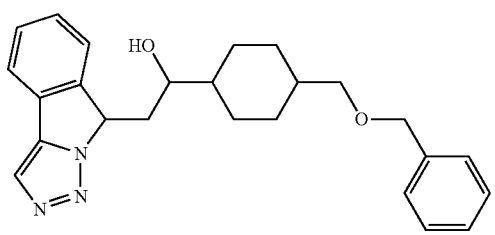 [SMILES: OC(CC1c2ccccc2-c2cnnn21)C1CCC(COCc2ccccc2)CC1] | 2-(8H-[1,2,3]triazolo[5,1-a]isoindol-8-yl)-1-(4-((benzyloxy)methyl)cyclohexyl)ethan-1-ol, |

-continued

| | | |
|---|---|---|
| 88 | 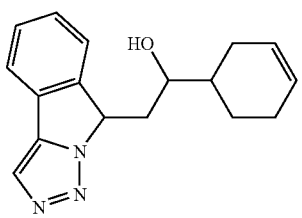 [SMILES: OC(CC1c2ccccc2-c2cnnn21)C1CC=CCC1] | 2-(8H-[1,2,3]triazolo[5,1-a]isoindol-8-yl)-1-(cyclohex-3-en-1-yl)ethan-1-ol, |
| 89 | 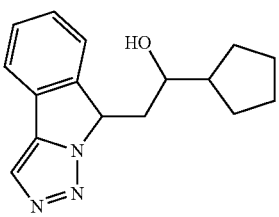 [SMILES: OC(CC1c2ccccc2-c2cnnn21)C1CCCC1] | 2-(8H-[1,2,3]triazolo[5,1-a]isoindol-8-yl)-1-cyclopentylethan-1-ol, |
| 90 | 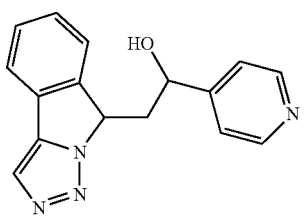 [SMILES: OC(CC1c2ccccc2-c2cnnn21)c1ccncc1] | 2-(8H-[1,2,3]triazolo[5,1-a]isoindol-8-yl)-1-(pyridin-4-yl)ethan-1-ol, |
| 91 | 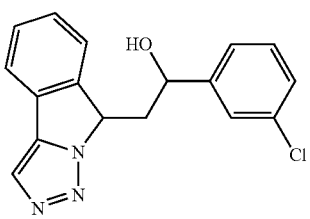 [SMILES: OC(CC1c2ccccc2-c2cnnn21)c1cccc(Cl)c1] | 2-(8H-[1,2,3]triazolo[5,1-a]isoindol-8-yl)-1-(3-chlorophenyl)ethan-1-ol, |
| 92 | 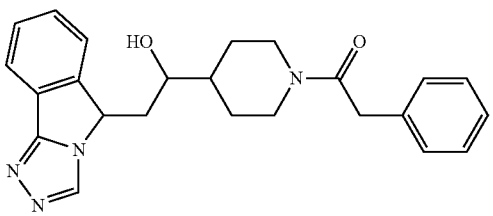 | 1-(4-(2-(8H-[1,2,3]triazolo[5,1-a]isoindol-8-yl)-1-hydroxyethyl)piperidin-1-yl)-2-phenylethan-1-one, |
| 93 | 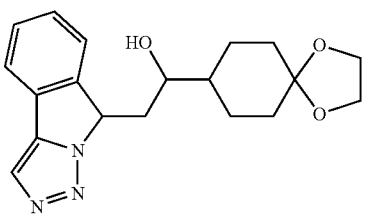 [SMILES: OC(CC1c2ccccc2-c2cnnn21)C1CCC2(CC1)OCCO2] | 1-(4-(2-(5H-[1,2,4]triazolo[3,4-a]isoindol-5-yl)-1-hydroxyethyl)piperidin-1-yl)-2-phenylethan-1-one, |
| 94 | 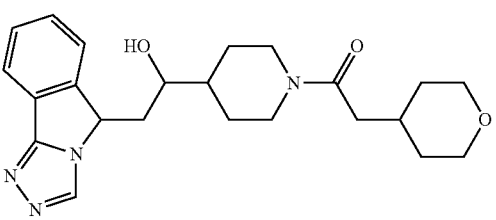 [SMILES: O=C(CC1CCOCC1)N1CCC(C(O)CC2c3ccccc3-c3nncn32)CC1] | 1-(4-(2-(5H-[1,2,4]triazolo[3,4-a]isoindol-5-yl)-1-hydroxyethyl)piperidin-1-yl)-2-(tetrahydro-2H-pyran-4-yl)ethan-1-one, |

| | | |
|---|---|---|
| 95 | 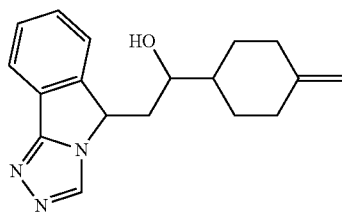 [SMILES: C=C1CCC(C(O)CC2c3ccccc3-c3nncn32)CC1] | 2-(5H-[1,2,4]triazolo[3,4-a]isoindol-5-yl)-1-(4-methylenecyclohexyl)ethan-1-ol, |
| 96 | 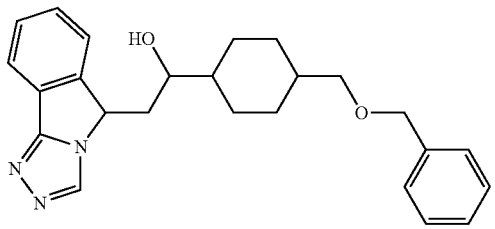 | 2-(5H-[1,2,4]triazolo[3,4-a]isoindol-5-yl)-1-(4-((benzyloxy)methyl)cyclohexyl)ethan-1-ol, |
| 97 | 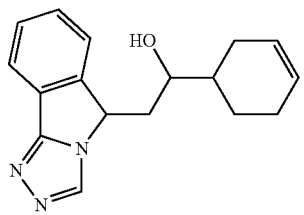 [SMILES: OC(CC1c2ccccc2-c2nncn21)C1CC=CCC1] | 2-(5H-[1,2,4]triazolo[3,4-a]isoindol-5-yl)-1-(cyclohex-3-en-1-yl)ethan-1-ol, |
| 98 | 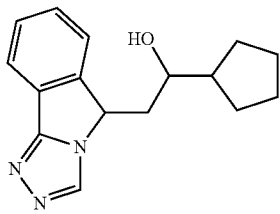 [SMILES: OC(CC1c2ccccc2-c2nncn21)C1CCCC1] | 2-(5H-[1,2,4]triazolo[3,4-a]isoindol-5-yl)-1-cyclopentylethan-1-ol, |
| 99 | 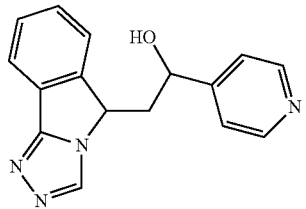 [SMILES: OC(CC1c2ccccc2-c2nncn21)c1ccncc1] | 2-(5H-[1,2,4]triazolo[3,4-a]isoindol-5-yl)-1-(pyridin-4-yl)ethan-1-ol, |
| 100 | 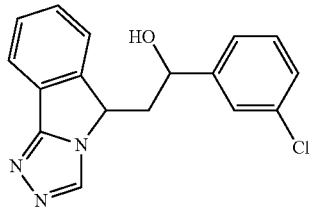 [SMILES: OC(CC1c2ccccc2-c2nncn21)c1cccc(Cl)c1] | 2-(5H-[1,2,4]triazolo[3,4-a]isoindol-5-yl)-1-(3-chlorophenyl)ethan-1-ol, |
| 102 | 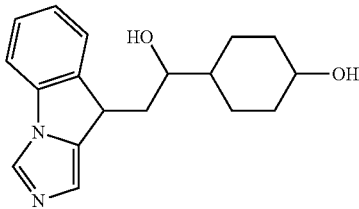 [SMILES: OC1CCC(C(O)CC2c3ccccc3-n3cncc32)CC1] | 4-(1-hydroxy-2-(9H-imidazo[1,5-a]indol-9-yl)ethyl)cyclohexan-1-ol, |

| | | |
|---|---|---|
| 103 | 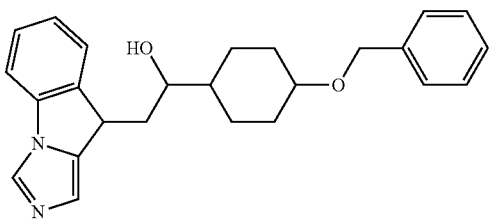 [SMILES: OC(CC1c2ccccc2-n2cncc21)C1CCC(OCc2ccccc2)CC1] | 1-(4-(benzyloxy)cyclohexyl)-2-(9H-imidazo[1,5-a]indol-9-yl)ethan-1-ol, |
| 104 | 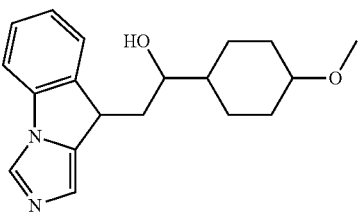 [SMILES: COC1CCC(C(O)CC2c3ccccc3-n3cncc32)CC1] | 2-(9H-imidazo[1,5-a]indol-9-yl)-1-(4-methoxycyclohexyl)ethan-1-ol, |
| 105 | 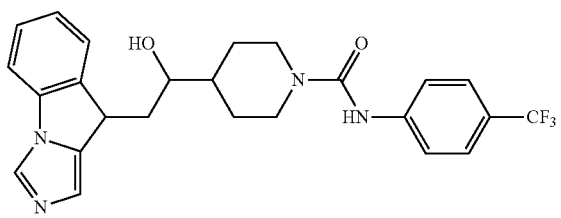 [SMILES: O=C(Nc1ccc(C(F)(F)F)cc1)N1CCC(C(O)CC2c3ccccc3-n3cncc32)CC1] | 4-(1-hydroxy-2-(9H-imidazo[1,5-a]indol-9-yl)ethyl)-N-(4-(trifluoromethyl)phenyl)piperidine-1-carboxamide, |
| 106 | 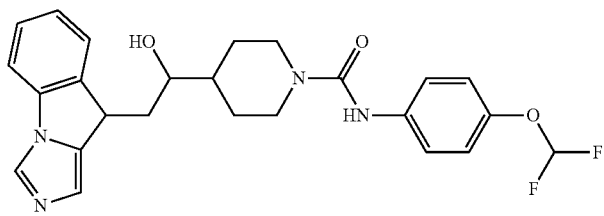 | N-(4-(difluoromethoxy)phenyl)-4-(1-hydroxy-2-(9H-imidazo[1,5-a]indol-9-yl)ethyl)piperidine-1-carboxamide, |
| 107 | 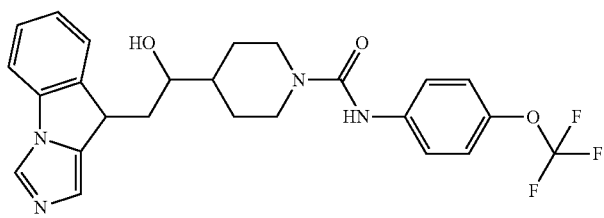 | 4-(1-hydroxy-2-(9H-imidazo[1,5-a]indol-9-yl)ethyl)-N-(4-(trifluoromethoxy)phenyl)piperidine-1-carboxamide, |
| 108 | 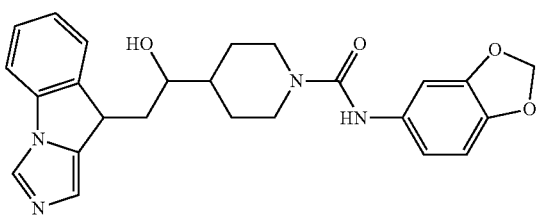 [SMILES: O=C(Nc1ccc2c(c1)OCO2)N1CCC(C(O)CC2c3ccccc3-n3cncc32)CC1] | N-(benzo[d][1,3]dioxol-5-yl)-4-(1-hydroxy-2-(9H-imidazo[1,5-a]indol-9-yl)ethyl)piperidine-1-carboxamide, |
| 109 | 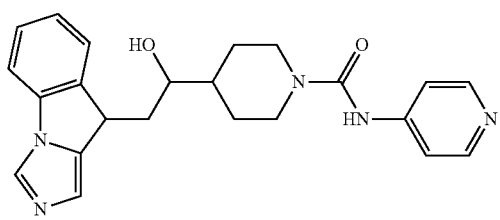 [SMILES: O=C(Nc1ccncc1)N1CCC(C(O)CC2c3ccccc3-n3cncc32)CC1] | 4-(1-hydroxy-2-(9H-imidazo[1,5-a]indol-9-yl)ethyl)-N-(pyridin-4-yl)piperidine-1-carboxamide, |

| | | |
|---|---|---|
| 110 | 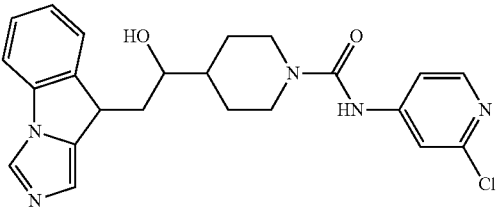 [SMILES: O=C(Nc1ccnc(Cl)c1)N1CCC(C(O)CC2c3ccccc3-n3cncc32)CC1] | N-(2-chloropyridin-4-yl)-4-(1-hydroxy-2-(9H-imidazo[1,5-a]indol-9-yl)ethyl)piperidine-1-carboxamide, |
| 111 | 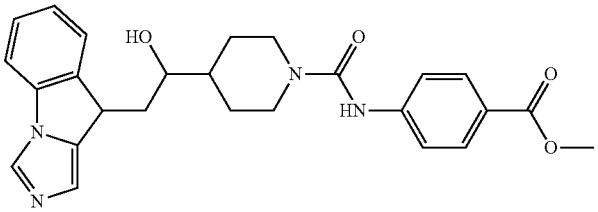 [SMILES: COC(=O)c1ccc(NC(=O)N2CCC(C(O)CC3c4ccccc4-n4cncc43)CC2)cc1] | methyl 4-(4-(1-hydroxy-2-(9H-imidazo[1,5-a]indol-9-yl)ethyl)piperidine-1-carboxamido)benzoate, |
| 112 | 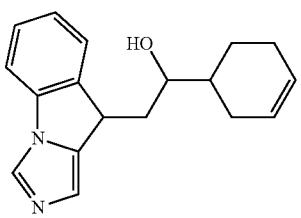 [SMILES: OC(CC1c2ccccc2-n2cncc21)C1CC=CCC1] | 1-(cyclohex-3-en-1-yl)-2-(9H-imidazo[1,5-a]indol-9-yl)ethan-1-ol, |
| 113 | 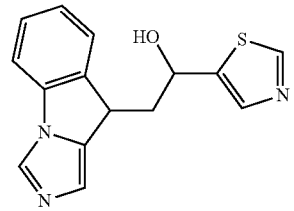 [SMILES: OC(CC1c2ccccc2-n2cncc21)c1cncs1] | 2-(9H-imidazo[1,5-a]indol-9-yl)-1-(thiazol-5-yl)ethan-1-ol, |
| 114 | 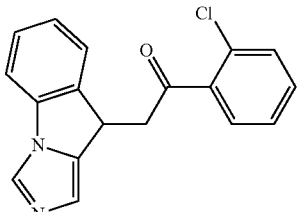 | 1-(2-chlorophenyl)-2-(9H-imidazo[1,5-a]indol-9-yl)ethan-1-one, |
| 115 | 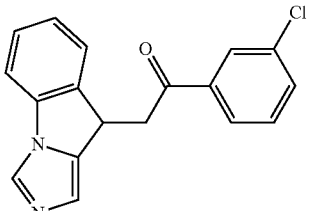 | 1-(3-chlorophenyl)-2-(9H-imidazo[1,5-a]indol-9-yl)ethan-1-one, |
| 116 | 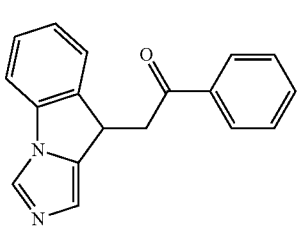 [SMILES: O=C(CC1c2ccccc2-n2cncc21)c1ccccc1] | 2-(9H-imidazo[1,5-a]indol-9-yl)-1-phenylethan-1-one, |

| | | |
|---|---|---|
| 117 | 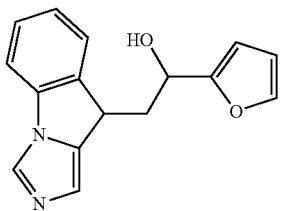 [SMILES: OC(CC1c2ccccc2-n2cncc21)c1ccco1] | 1-(furan-2-yl)-2-(9H-imidazo[1,5-a]indol-9-yl)ethan-1-ol, |
| 118 | 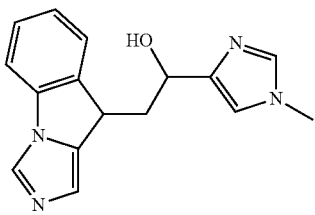 [SMILES: Cn1cnc(C(O)CC2c3ccccc3-n3cncc32)c1] | 2-(9H-imidazo[1,5-a]indol-9-yl)-1-(1-methyl-1H-imidazol-4-yl)ethan-1-ol, |
| 119 | 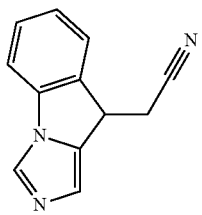 [SMILES: N#CCC1c2ccccc2-n2cncc21] | 2-(9H-imidazo[1,5-a]indol-9-yl)acetonitrile, or |
| 120 | 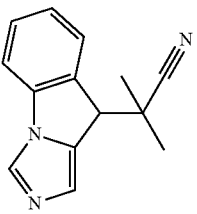 [SMILES: CC(C)(C#N)C1c2ccccc2-n2cncc21] | 2-(9H-imidazo[1,5-a]indol-9-yl)-2-methylpropanenitrile. |

36. The composition according to claim 35 further comprising a pharmaceutically acceptable diluent, excipient, or carrier.

37. A method for treating cancer in a subject in need thereof, comprising administering an effective amount of the composition according to claim 36 to the subject.

38. The method of claim 37, wherein the subject is also in need of treatment for immunosuppression associated with cancer or treatment of the cancer.

* * * * *